United States Patent
Bray et al.

(10) Patent No.: US 12,115,216 B2
(45) Date of Patent: Oct. 15, 2024

(54) ANTI-HUMAN PAPILLOMAVIRUS (HPV) ANTIGEN-BINDING PROTEINS AND METHODS OF USE THEREOF

(71) Applicant: Regeneron Pharmaceuticals, Inc., Tarrytown, NY (US)

(72) Inventors: Kevin A. Bray, Garnerville, NY (US); Frank Delfino, Poughquag, NY (US); Matthew C. Franklin, Great Neck, NY (US); Elena S. Garnova, White Plains, NY (US); Jessica Kirshner, New York, NY (US); Douglas MacDonald, New York, NY (US); William Olson, Yorktown Heights, NY (US); Gavin Thurston, Millerton, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 18/081,782

(22) Filed: Dec. 15, 2022

(65) Prior Publication Data

US 2023/0270837 A1 Aug. 31, 2023

Related U.S. Application Data

(60) Continuation of application No. 16/992,188, filed on Aug. 13, 2020, now Pat. No. 11,559,576, which is a division of application No. 16/019,703, filed on Jun. 27, 2018, now Pat. No. 10,806,780.

(60) Provisional application No. 62/525,937, filed on Jun. 28, 2017.

(51) Int. Cl.
| | | |
|---|---|---|
| *A61K 39/12* | (2006.01) | |
| *A61K 39/00* | (2006.01) | |
| *A61P 31/20* | (2006.01) | |
| *A61P 35/00* | (2006.01) | |
| *C07K 16/08* | (2006.01) | |
| *C07K 16/28* | (2006.01) | |

(52) U.S. Cl.
CPC .......... *A61K 39/12* (2013.01); *A61K 39/0008* (2013.01); *A61K 39/0011* (2013.01); *A61P 31/20* (2018.01); *A61P 35/00* (2018.01); *C07K 16/084* (2013.01); *C07K 16/2809* (2013.01); *C07K 16/2833* (2013.01); *C07K 16/2875* (2013.01); *A61K 2039/545* (2013.01); *A61K 2039/572* (2013.01); *C07K 2317/32* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,401,627 A | 3/1995 | Dillner et al. | |
| 9,453,075 B2 | 9/2016 | Cheung et al. | |
| 10,806,780 B2* | 10/2020 | Bray | A61K 39/12 |
| 11,559,576 B2 | 1/2023 | Bray et al. | |
| 2015/0023979 A1 | 1/2015 | Kuhne | |
| 2016/0152681 A1 | 6/2016 | Hinrichs et al. | |
| 2016/0175358 A1 | 6/2016 | Jakobovits et al. | |
| 2016/0311861 A1 | 10/2016 | Grabowska et al. | |
| 2021/0317183 A1* | 10/2021 | Zhao | C07K 14/70596 |

FOREIGN PATENT DOCUMENTS

| | | |
|---|---|---|
| CN | 105131113 A | 12/2015 |
| EP | 0451550 A2 | 10/1991 |
| EP | 31215885 A1 | 6/2015 |
| WO | WO-1992/005248 A1 | 4/1992 |
| WO | WO-2002/077012 A2 | 10/2002 |
| WO | WO-2007/129218 A2 | 11/2007 |
| WO | WO-2010/027973 A1 | 3/2010 |
| WO | WO-2015/184228 A1 | 12/2015 |
| WO | WO-2016/182957 A1 | 11/2016 |
| WO | WO-2018/067618 A1 | 4/2018 |

OTHER PUBLICATIONS

International Search Report and Written Opinion from PCT/US2018/039654 mailed on Nov. 7, 2018.
Riemer et al., "A conserved E7-derived cytotoxic T lymphocyte epitope expressed on human papillomavirus 16-transformed HLA-A2+ epithelial cancers", The Journal of Biological Chemistry, vol. 285(38), pp. 29608-29622, (2010).
Xu et al., "Ii-Key/HPV16 E7 hybrid peptide immunotherapy for HPV16+ cancers", Vaccine, vol. 27(34), pp. 4641-4647, (2009).
Bodmer et al., "Anti-HLA-A2 antibody-enhancement of peptide association with HLA-A2 as detected by cytotoxic T lymphocytes", Nature. Nov. 23, 1989;342(6248):443-6.
Youde et al., "Use of Fluorogenic Histocompatibility Leukocyte Antigen-A*0201/HPV 16 E7 Peptide Complexes to Isolate Rare Human Cytotoxic T-Lymphocyte—recognizing Endogenous Human Papillomavirus Antigens", Cancer Res. Jan. 15, 2000;60(2):365-71.
Albers et al., "Antitumor Activity of Human Papillomavirus Type 16 E7-Specific T Cells against Virally Infected Squamous Cell Carcinoma of the Head and Neck", Cancer Res. Dec. 1, 2005;65(23):11146-55.
Lybarger et al., "Enhanced Immune Presentation of a Single-chain Major Histocompatibility Complex Class I Molecule Engineered to Optimize Linkage of a C-terminally Extended Peptide", J Biol Chem. Jul. 18, 2003;278(29):27105-11.
Lybarger et al., "Single-Chain MHC Class I Molecules are Potent Stimulators of Specific CD8+ T Cells and Antibodies, and Can Avoid Virus-Mediated Downregulation", FASEB 2002; 22 (1) Supplement; 240.2.
Hansen et al., "Translational and basic applications of peptide-MHCI Single chain trimers", Trends Immunol. Oct. 2010;31(10): 363-369.

(Continued)

*Primary Examiner* — Agnieszka Boesen
(74) *Attorney, Agent, or Firm* — McCarter & English, LLP; Marcie B. Clarke; Deborah L. Nagle

(57) ABSTRACT

The present invention provides antigen-binding proteins that specifically bind to an HLA-displayed human papillomavirus (HPV) peptide, and therapeutic and diagnostic methods of using those binding proteins.

19 Claims, No Drawings

Specification includes a Sequence Listing.

(56) References Cited

OTHER PUBLICATIONS

Truscott et al., "Disulfide Bond Engineering to Trap Peptides in the MHC Class I Binding Groove", J Immunol. May 15, 2007;178(10):6280-9.
Truscott et al., "Human Major Histocompatibility Complex (MHC) Class I Molecules with Disulfide Traps Secure Disease-related Antigenic Peptides and Exclude Competitor Peptides", J Biol Chem. Mar. 21, 2008;283(12):7480-90.
Yu et al., "Cutting Edge: Single-Chain Trimers of MHC Class I Molecules Form Stable Structures That Potently Stimulate Antigen-Specific T Cells and B Cells", J Immunol. Apr. 1, 2002;168(7):3145-9.
Rosales et al., "Antibodies against human papillomavirus (HPV) type 16 and 18 E2, E6 and E7 proteins in sera: Correlation with presence of papillomavirus DNA", J. Med. Virol. 65:736-744, 2001.
Nilges, et al. "Human Papillomavirus Type 16 E7 Peptide-Directed CD8+ T Cells from Patients with Cervical Cancer Are Cross-Reactive with the Coronavirus NS2 Protein," Journal of Virology. 2003.77:5464-5474.

\* cited by examiner

ANTI-HUMAN PAPILLOMAVIRUS (HPV) ANTIGEN-BINDING PROTEINS AND METHODS OF USE THEREOF

RELATED APPLICATIONS

This application is a continuation of U.S. patent application Ser. No. 16/992,188, filed on Aug. 13, 2020, which is a divisional of U.S. patent application Ser. No. 16/019,703, filed on Jun. 27, 2018, now U.S. Pat. No. 10,806,780, issued on Oct. 20, 2020, which claims priority to U.S. Provisional Application No. 62/525,937, filed on Jun. 28, 2017. The entire contents of each of the foregoing application are expressly incorporated by reference herein.

SEQUENCE LISTING

The instant application contains a Sequence Listing which has been submitted electronically in XML file format and is hereby incorporated by reference in its entirety. Said XML copy, created on Jan. 5, 2023, is named 118003-28904_SL.xml and is 606,446 bytes in size.

FIELD OF THE INVENTION

The present invention is related to antigen-binding proteins that specifically bind to an HLA-displayed human papillomavirus (HPV) peptide, and therapeutic and diagnostic methods of using those binding proteins.

BACKGROUND OF THE INVENTION

Human papillomavirus (HPV) is a group of small, non-enveloped DNA viruses that are extremely common worldwide. HPV is mainly transmitted through sexual contact and most people are infected with HPV shortly after the onset of sexual activity.

There are more than 170 types of HPV, some of which can cause warts or benign papillomas, and others, at least 13 of which, cause cancer (also known as high risk type HPVs), including cervical cancer, anogenital cancers (cancers of the anus, penis, vagina and vulva), head/neck cancers, and oropharynx cancers, including the back of the throat, the base of the tongue, and tonsils. Indeed, HPV is present in 20-40% of all head and neck squamous cell carcinomas (HNSCC) and in 100% of cervical cancers.

Cervical cancer is the second most common cancer in women living in less developed regions with an estimated 445,000 new cases in 2012 (84% of the new cases worldwide). In 2012, approximately 270,000 women died from cervical cancer; more than 85% of these deaths occurring in low- and middle-income countries.

Two HPV types (16 and 18) cause approximately 70% of all cervical cancers and precancerous cervical lesions. Cancer development upon persistent infection with a high risk HPV subtype, such as HPV 16 or 18, is mainly attributable to the expression of two viral oncoproteins, E6 and E7, which are continuously expressed in lesions and presented on the cell surface by MHC class I, but are not expressed in normal cells. E6 and E7 promote genomic instability and cellular transformation by degrading the tumor suppressors p53 and Rb in a proteasome-dependent manner. Tumors arise several years after the initial cellular immortalizing events and the continuous expression of E6 and E7 is required for maintenance of the transformed phenotype, and prevention of cell growth arrest and/or apoptosis (McLaughlin-Drubin M. E. & Miinger K., *Virology* (2009) 384:335-344).

Although vaccines targeting the HPV L1 and L2 major capsid proteins of HPV-6, -11, -16 and -18 subtypes have been developed to prevent infection, such vaccines cannot treat subjects having established lesions. Thus, the treatment of subjects having cervical cancer remains the use of traditional approaches which are highly invasive and morbid, such as surgery, radiotherapy, and chemotherapy. Furthermore, although such treatments may provide benefit for subjects having early stage cervical cancer, they are of limited value to patients with advanced or recurrent cervical cancer.

Accordingly, there is an unmet need in the art for new therapeutic strategies to target HPV with high specificity and to treat cervical cancer and other cancers caused by HPV.

BRIEF SUMMARY OF THE INVENTION

The present invention provides antigen-binding proteins that specifically bind to a conformational epitope of an HLA-displayed human papillomavirus (HPV) 16 E7 peptide (HLA-A2:HPV16E7). The antigen-binding proteins of the present invention bind with a high degree of specificity to HLA-displayed HPV16E7 and do not bind to HLA-displayed peptides that differ by 1, 2, 3, 4, 5 or more amino acids. The antigen-binding proteins of the invention allow for specific targeting of HPV16E7 peptide-presenting cells (i.e., cells presenting on their surface an HPV16E7 peptide bound to an MHC molecule, e.g., HLA-A2), such as cancer cells expressing HPV16E7 and, in some embodiments, stimulating T cell activation, e.g., to stimulate T cell-mediated killing of such cells. Furthermore, when fused to a detectable moiety, the antigen-binding proteins of the present invention allow for diagnosis and prognosis of HPV16E7-positive diseases or disorders with high sensitivity to changes in the number and distribution of HPV16E7 peptide-presenting cells, a more relevant measure of disease progression than circulating HPV16E7 levels.

The antigen-binding proteins of the invention may be antibodies, such as full-length (for example, an IgG1 or IgG4 antibody) antibodies, or may comprise only an antigen-binding portion of an antibody (for example, a Fab, F(ab')2 or scFv fragment), and may be modified to affect functionality, e.g., to eliminate residual effector functions (Reddy et al., 2000, J. Immunol. 164:1925-1933). In some embodiments, the antigen-binding proteins of the invention may be antibodies, or antigen-binding fragments thereof. In certain embodiments, the antigen-binding proteins may be bispecific.

In a first aspect, the present invention provides isolated recombinant antigen-binding proteins that bind specifically to a conformational epitope of an HLA-displayed human papillomavirus (HPV) 16 E7 peptide, such as a HLA-displayed peptide comprising amino acid residues 11-19 or 82-90 of HPV16E7. In certain embodiments, the antigen-binding proteins are antibodies. In some embodiments, the antibodies are fully human.

Exemplary anti-HLA-A2:HPV16E7 antigen-binding proteins of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-HLA-A2:

HPV16E7 antibodies. Table 2 sets forth the nucleic acid sequence identifiers of the HCVRs, LCVRs, HCDR1, HCDR2 HCDR3, LCDR1, LCDR2 and LCDR3 of the exemplary anti-HLA-A2:HPV16E7 antibodies.

The present invention provides antigen-binding proteins comprising an HCVR comprising an amino acid sequence selected from any of the HCVR amino acid sequences listed in Table 1, or a substantially similar sequence thereof having at least 90%, at least 95%, at least 96%, at least 97%, at least 98% or at least 99% sequence identity thereto.

The present invention also provides antigen-binding proteins comprising an LCVR comprising an amino acid sequence selected from any of the LCVR amino acid sequences listed in Table 1, or a substantially similar sequence thereof having at least 90%, at least 95%, at least 96%, at least 97%, at least 98% or at least 99% sequence identity thereto.

The present invention also provides antigen-binding proteins comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antigen-binding proteins comprising an HCVR/LCVR amino acid sequence pair contained within any of the exemplary anti-HLA-A2:HPV16E7 antigen-binding proteins listed in Table 1. In certain embodiments, the HCVR/LCVR amino acid sequence pair is selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530. In certain embodiments, the HCVR/LCVR amino acid sequence pair is selected from one of SEQ ID NOs: 2/10 (e.g., H4sH17364N), 34/42 (e.g., H4sH17670P), 82/90 (e.g., H4sH17675P), 194/202 (e.g., H4sH17930N2), 282/290 (e.g., H4sH21064P), and 506/514 (e.g., H4sH17363N).

In certain embodiments, the present invention provides anti-HLA-A2:HPV16E7 antigen-binding proteins comprising a HCVR and a LCVR, said HCVR comprising an amino acid sequence listed in Table 1 having no more than five amino acid substitutions, and said LCVR comprising an amino acid sequence listed in Table 1 having no more than five amino acid substitutions. For example, the present invention provides anti-HLA-A2:HPV16E7 antigen-binding proteins comprising a HCVR and a LCVR, said HCVR comprising an amino acid sequence of SEQ ID NO: 194 having no more than five amino acid substitutions, and said LCVR comprising an amino acid sequence of SEQ ID NO: 202 having no more than five amino acid substitutions. In another exemplary embodiment, the present invention provides anti-HLA-A2:HPV16E7 antigen-binding proteins comprising a HCVR and a LCVR, said HCVR comprising an amino acid sequence of SEQ ID NO: 194 having at least one amino acid substitution, and said LCVR comprising an amino acid sequence of SEQ ID NO: 202 having at least one amino acid substitution.

The present invention also provides antigen-binding proteins comprising a heavy chain CDR1 (HCDR1) comprising an amino acid sequence selected from any of the HCDR1 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a heavy chain CDR2 (HCDR2) comprising an amino acid sequence selected from any of the HCDR2 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a heavy chain CDR3 (HCDR3) comprising an amino acid sequence selected from any of the HCDR3 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a light chain CDR1 (LCDR1) comprising an amino acid sequence selected from any of the LCDR1 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a light chain CDR2 (LCDR2) comprising an amino acid sequence selected from any of the LCDR2 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a light chain CDR3 (LCDR3) comprising an amino acid sequence selected from any of the LCDR3 amino acid sequences listed in Table 1 or a substantially similar sequence thereof having at least 90%, at least 95%, at least 96%, at least 97%, at least 98% or at least 99% sequence identity.

The present invention also provides antigen-binding proteins comprising a HCDR3 and a LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antigen-binding proteins, comprising an HCDR3/LCDR3 amino acid sequence pair contained within any of the exemplary anti-HLA-A2:HPV16E7 antigen-binding proteins listed in Table 1. In certain embodiments, the HCDR3/LCDR3 amino acid sequence pair is selected from the group consisting of SEQ ID NOs: 8/16 (e.g., H4sH17364N), 40/48 (e.g., H4sH17670P), 88/96 (e.g., H4sH17675P), 200/208 (e.g., H4sH17930N2), 288/296 (e.g., H4sH21064P), and 512/520 (e.g., H4sH17363N).

The present invention also provides antigen-binding proteins comprising a HCVR and a LCVR, said HCVR comprising HCDR1 comprising an amino acid sequence differing from an amino acid sequence listed in Table 1 by 1 amino acid, HCDR2 comprising an amino acid sequence differing from an amino acid sequence listed in Table 1 by 1 amino acid, and HCDR3 comprising an amino acid sequence differing from an amino acid sequence listed in Table 1 by 1 amino acid. In certain embodiments, the present invention provides antigen-binding proteins comprising a HCVR and a LCVR, said LCVR comprising LCDR1 comprising an amino acid sequence differing from an amino acid sequence listed in Table 1 by 1 amino acid, LCDR2 comprising an amino acid sequence differing from an amino acid sequence listed in Table 1 by 1 amino acid, and LCDR3 comprising an amino acid sequence differing from an amino acid sequence listed in Table 1 by 1 amino acid. For example, the present invention provides anti-HLA-A2: HPV16E7 antigen-binding proteins comprising a HCVR and a LCVR, said HCVR comprising HCDR1 comprising an amino acid sequence of SEQ ID NO: 196 or an amino acid sequence differing from SEQ ID NO: 196 by 1 amino acid, HCDR2 comprising an amino acid sequence of SEQ ID NO: 198 or an amino acid sequence differing from SEQ ID NO: 198 by 1 amino acid, and HCDR3 comprising an amino acid sequence of SEQ ID NO: 200 or an amino acid sequence differing from SEQ ID NO: 200 by 1 amino acid. In another exemplary embodiment, the present invention provides antigen-binding proteins comprising a HCVR and a LCVR, said LCVR comprising LCDR1 comprising an amino acid sequence of SEQ ID NO: 204 or an amino acid sequence differing from SEQ ID NO: 204 by 1 amino acid, LCDR2 comprising an amino acid sequence of SEQ ID NO: 206 or an amino acid sequence differing from SEQ ID NO: 206 by 1 amino acid, and LCDR3 comprising an amino acid sequence of SEQ ID NO: 208 or an amino acid sequence differing from SEQ ID NO: 208 by 1 amino acid.

The present invention also provides antigen-binding proteins comprising a set of six CDRs (i.e., HCDR1-HCDR2-HCDR3-LCDR1-LCDR2-LCDR3) contained within any of the exemplary antigen-binding proteins listed in Table 1. In certain embodiments, the HCDR1-HCDR2-HCDR3-LCDR1-LCDR2-LCDR3 amino acid sequence set is selected from the group consisting of SEQ ID NOs: 4-6-8-12-14-16 (e.g., H4sH17364N), 36-38-40-44-46-48 (e.g., H4sH17670P), 84-86-88-92-94-96 (e.g., H4sH17675P), 196-198-200-204-206-208 (e.g., H4sH17930N2), 284-286-288-292-294-296 (e.g., H4sH21064P), and 508-510-512-516-518-520 (e.g., H4sH17363N).

In a related embodiment, the present invention provides antigen-binding proteins comprising a set of six CDRs (i.e., HCDR1-HCDR2-HCDR3-LCDR1-LCDR2-LCDR3) contained within an HCVR/LCVR amino acid sequence pair as defined by any of the exemplary antigen-binding proteins listed in Table 1. For example, the present invention includes antigen-binding proteins comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., H4sH17364N), 34/42 (e.g., H4sH17670P), 82/90 (e.g., H4sH17675P), 194/202 (e.g., H4sH17930N2), 282/290 (e.g., H4sH21064P), and 506/514 (e.g., H4sH17363N).

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antigen-binding protein.

The present invention includes anti-HLA-A2:HPV16E7 antigen-binding proteins having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) *JBC* 277:26733). In other applications, modification of galactosylation can be made in order to modify complement dependent cytotoxicity (CDC).

In certain embodiments, the antigen-binding proteins of the invention are monoclonal antibodies comprising a HCVR and a LCVR amino acid sequence pair (HCVR/LCVR) comprising any of the HCVR amino acid sequences listed in Table 1 paired with any of the LCVR amino acid sequences listed in Table 1. In certain embodiments, the monoclonal antibodies comprise a Fc domain of an isotype selected from the group consisting of IgA, IgD, IgE, IgG, IgG1, IgG2, IgG3, IgG4, IgM and a variant thereof.

The present invention provides antigen-binding proteins, or antigen-binding fragments thereof, comprising a heavy chain comprising an amino acid sequence selected from any of the HC amino acid sequences listed in Table 3, or a substantially similar sequence thereof having at least 90%, at least 95%, at least 98% or at least 99% sequence identity thereto.

The present invention also provides antigen-binding proteins, or antigen-binding fragments thereof, comprising a light chain comprising an amino acid sequence selected from any of the LC amino acid sequences listed in Table 3, or a substantially similar sequence thereof having at least 90%, at least 95%, at least 98% or at least 99% sequence identity thereto.

The present invention also provides antigen-binding proteins, or antigen-binding fragments thereof, comprising a HC and a LC amino acid sequence pair (HC/LC) comprising any of the HC amino acid sequences listed in Table 3 paired with any of the LC amino acid sequences listed in Table 3. According to certain embodiments, the present invention provides antibodies, or antigen-binding fragments thereof, comprising an HC/LC amino acid sequence pair contained within any of the exemplary anti-PD-1 antibodies listed in Table 3. In certain embodiments, the HC/LC amino acid sequence pair is selected from the group consisting of SEQ ID NOs: 578/579, 580/581, 582/583, 584/585, 586/587, 588/589, 590/591, and 592/593.

In one aspect, the present invention provides antigen-binding proteins or antigen-binding fragments thereof that bind to a HLA-peptide complex wherein the antigen-binding protein or antigen-binding fragment thereof contacts at least 60%, at least 70%, at least 80% or at least 90% of the amino acid residues of the peptide that is comprised in the HLA-peptide complex. In certain embodiments, the antigen-binding protein or antigen-binding fragment thereof "covers" or contacts all of the amino acid residues of the peptide comprised in the HLA-peptide complex. In certain embodiments, the antigen-binding protein or antigen-binding fragment thereof binds to a HLA-peptide complex with high affinity and specificity, wherein the antigen-binding protein or antigen-binding fragment thereof contacts the entire length of the displayed peptide. "Contact", as used herein includes direct or water-mediated hydrogen bonds, charge-charge interactions, or hydrophobic/van der Waals interactions. In one embodiment, the antigen-binding protein or antigen-binding fragment thereof binds to HLA-A2-HPV16E7 11-19 peptide complex wherein the antigen-binding protein binds to at least 6 of 10 amino acid residues of peptide 11-19 (SEQ ID NO: 538) and to HLA-A2 such that it covers the HLA-A2-peptide complex completely. In certain embodiments, the antigen-binding protein or antigen-binding fragment thereof comprises the CDRs of a HCVR and the CDRs of a LCVR, wherein the HCVR and LCVR each has an amino acid sequence selected from the HCVR and LCVR sequences listed in Table 1. In one embodiment, the antigen-binding protein is fully human. In certain embodiments, the fully human antigen-binding proteins are not obtained using phage display methods and technologies. In one embodiment, the antigen-binding proteins comprise a light chain variable region of the IGKV1-39 sub-type.

In certain embodiments, the present invention provides antigen-binding proteins or antigen-binding fragments thereof that bind to HLA-A2:HPV16E7 11-19 peptide, wherein the antigen-binding protein binds to one or more amino acids of SEQ ID NO: 538. In one embodiment, the antigen-binding protein binds to at least 6 amino acids of SEQ ID NO: 538. In one embodiment, the antigen-binding protein binds to one or more amino acids selected from the group consisting of Y11, D14, L15, P 17 and E18 of SEQ ID NO: 538.

In certain embodiments, the present invention provides antigen-binding protein that binds specifically to a conformational epitope of an HLA-A2 presented human papillomavirus (HPV) 16 E7 peptide (HPV16E7 peptide), wherein the conformational epitope comprises one or more amino acids of SEQ ID NO: 538. In the certain embodiments, the conformational epitope comprises one or more amino acids selected from the group consisting of Y11, D14, L15, P 17 and E18 of SEQ ID NO: 538.

The present invention also provides for antigen-binding proteins that compete for specific binding to HLA-A2:HPV16E7 with an antigen-binding protein comprising the CDRs of a HCVR and the CDRs of a LCVR, wherein the HCVR and LCVR each has an amino acid sequence selected from the HCVR and LCVR sequences listed in Table 1.

The present invention also provides antigen-binding proteins that cross-compete for binding to HLA-A2:HPV16E7 with a reference antigen-binding protein comprising the CDRs of a HCVR and the CDRs of a LCVR, wherein the HCVR and LCVR each has an amino acid sequence selected from the HCVR and LCVR sequences listed in Table 1.

The present invention also provides antigen-binding proteins that bind to the same epitope as a reference antigen-binding protein comprising the CDRs of a HCVR and the CDRs of a LCVR, wherein the HCVR and LCVR each has an amino acid sequence selected from the HCVR and LCVR sequences listed in Table 1. In certain embodiments, the present invention provides antigen-binding proteins that bind to the same epitope as a reference antigen-binding protein comprising the CDRs of a HCVR and the CDRs of a LCVR, wherein the HCVR is selected from the group consisting of SEQ ID NOs: 2, 34, 82, 194, 282 and 504, and the LCVR is selected from the group consisting of SEQ ID Nos: 10, 42, 90, 202, 290 and 514.

In one embodiment, the invention provides a recombinant isolated antigen-binding protein that binds specifically to a conformational epitope of an HLA-A2 presented human papillomavirus (HPV) 16 E7 peptide (HPV16E7 peptide), wherein the antigen-binding protein has a property selected from the group consisting of: (a) binds monomeric HLA-A2:HPV16E7 11-19 peptide with a binding dissociation equilibrium constant ($K_D$) of less than about 20 nM as measured in a surface plasmon resonance assay at 25° C.; (b) binds monomeric HLA-A2:HPV16E7 82-90 peptide with a binding dissociation equilibrium constant ($K_D$) of less than about 25 nM as measured in a surface plasmon resonance assay at 25° C.; (c) binds to HLA-A2:HPV16E7 11-19 peptide expressing cells with an $EC_{50}$ less than about 6 nM and does not bind to cells expressing predicted off-target peptides as determined by luminescence assay; (d) binds to HLA-A2:HPV16E7 82-90 peptide expressing cells with an $EC_{50}$ less than about 1 nM and do not substantially bind to cells expressing predicted off-target peptides as determined by luminescence assay; (e) binds to HLA-A2:HPV16E7 11-19 peptide expressing cells with an $EC_{50}$ less than about 30 nM as determined by flow cytometry assay; (f) binds to HLA-A2:HPV16E7 82-90 peptide expressing cells with an $EC_{50}$ less than about 75 nM as determined by flow cytometry assay; and (g) the conformational epitope comprises one or more amino acids of SEQ ID NO: 538. As disclosed elsewhere herein, an "off-target peptide" refers to a peptide that differs by 1, 2, 3, 4, 5 or more amino acids from a target peptide (e.g., HPV16 E7 11-19 peptide).

In a second aspect, the present invention provides nucleic acid molecules encoding anti-HLA-A2:HPV16E7 antigen-binding proteins. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 96%, at least 97%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-HLA-A2:HPV16E7 antigen-binding proteins listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-HLA-A2:HPV16E7 antigen-binding proteins listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 96%, at least 97%, at least 98% or at least 99% sequence identity thereto. In certain embodiments according to this aspect of the invention, the nucleic acid molecule encodes an HCVR and LCVR, wherein the HCVR and LCVR are both derived from the same anti-HLA-A2: HPV16E7 antigen-binding protein listed in Table 1.

The present invention provides nucleic acid molecules encoding any of the heavy chain amino acid sequences listed in Table 3. The present invention also provides nucleic acid molecules encoding any of the light chain amino acid sequences listed in Table 3.

The present invention also provides nucleic acid molecules encoding both heavy chain (HC) and a light chain (LC), wherein the HC comprises an amino acid sequence of any of the HC amino acid sequences listed in Table 3, and wherein the LC comprises an amino acid sequence of any of the LC amino acid sequences listed in Table 3.

In a related aspect, the present invention provides recombinant expression vectors capable of expressing a polypeptide comprising a heavy and/or or light chain variable region of an anti-HLA-A2:HPV16E7 antigen-binding protein. For example, the present invention includes recombinant expression vectors comprising any of the nucleic acid molecules mentioned above, i.e., nucleic acid molecules encoding any of the HCVR, LCVR, and/or CDR sequences as set forth in Table 1. The present invention also provides recombinant expression vectors capable of expressing a polypeptide comprising a heavy and/or light chain of an anti-HLA-A2: HPV16E7 antigen-binding protein. For example, the present invention includes recombinant expression vectors comprising any of the nucleic acid molecules mentioned above, i.e., nucleic acid molecules encoding any of the heavy chain or light chain sequences as set forth in Table 2. Also included within the scope of the present invention are host cells into which such vectors have been introduced, as well as methods of producing the antigen-binding proteins by culturing the host cells under conditions permitting production of the antigen-binding proteins, and recovering the antigen-binding proteins so produced.

In a third aspect, the present invention provides a pharmaceutical composition comprising a therapeutically effective amount of a recombinant isolated antigen-binding protein that binds specifically to a conformational epitope of an HLA-A2 presented HPV16E7 peptide (e.g., a peptide comprising amino acid residues 11-19 or 82-90 of HPV16E7), and a pharmaceutically acceptable carrier. In a related aspect, the invention features a composition which is a combination of an anti-HLA-A2:HPV16E7 antigen-binding protein and a second therapeutic agent. In one embodiment, the second therapeutic agent is any agent that is advantageously combined with an anti-HLA-A2:HPV16E7 antigen-binding protein. Exemplary agents that may be advantageously combined with an anti-HLA-A2:HPV16E7 antigen-binding protein include, without limitation, other agents that bind and/or modulate HPV replication or infection (including other antibodies or antigen-binding fragments thereof, etc.) and/or agents which modulate immune cell activation. Additional therapies that can be used in combination with the anti-HLA-A2:HPV16E7 antigen-binding proteins of the present invention are disclosed elsewhere herein.

In a fourth aspect, the invention provides methods to treat a subject having an HPV-associated disease or disorder, such as an HPV16E7-positive cancer. The methods include administering a therapeutically effective amount of an anti-HLA-A2:HPV16E7 antigen-binding protein of the invention or a pharmaceutical composition of the invention to the subject in need thereof. The disorder treated is any disease or condition which is improved, ameliorated, inhibited or prevented by the antigen-binding proteins and compositions provided herein. In certain embodiments, the antigen-binding protein (or pharmaceutical composition) of the invention is administered in combination with a second therapeutic agent to the subject in need thereof. The second therapeutic agent may be selected from the group consisting of an antibody to a T cell co-inhibitor, an antibody to a tumor cell antigen, an antibody to a T cell receptor, an antibody to an epitope on a virally infected cell, a cytotoxic agent, an anti-cancer drug, an anti-viral drug, an anti-inflammatory drug (e.g., corticosteroids), chemotherapeutic agent, surgery, radiation therapy, an immunosuppressant and any other drug or therapy known in the art. In certain embodiments, the second therapeutic agent may be an agent that helps to counteract or reduce any possible side effect(s) associated with antigen-binding protein of the invention, if such side effect(s) should occur.

In certain embodiments, the present invention provides methods for suppressing growth of a HPV-associated cancer. For example, the present invention provides methods to suppress tumor growth due to a primary tumor or a metastatic tumor in a subject. In certain embodiments, the present invention provides methods to enhance survival (e.g., progression-free survival or overall survival) of a subject with a HPV-associated cancer. Examples of cancer include, but are not limited to, squamous cell carcinomas, such as squamous cell carcinoma of head and neck, cervical cancer, anogenital cancer, oropharyngeal cancer.

In certain embodiments, the present invention provides methods for inhibiting or suppressing growth of established tumors. The methods comprise administering to a subject in need thereof a pharmaceutical composition comprising a therapeutically effective amount of an antigen-binding protein of the present invention. In certain embodiments, the antigen-binding protein is administered in combination with a second therapeutic agent.

The antigen-binding protein, e.g., antibody, or antigen-binding fragment thereof, may be administered subcutaneously, intravenously, intradermally, intraperitoneally, orally, intramuscularly, or intracranially. The antigen-binding protein, e.g., antibody or antigen-binding fragment thereof, may be administered at a dose of about 0.1 mg/kg of body weight to about 100 mg/kg of body weight of the subject.

In a fifth aspect, the present invention provides an isolated nucleic acid molecule encoding a chimeric antigen receptor (CAR). The CAR may include an extracellular binding domain that specifically binds to a conformational epitope of an HLA-A2 presented human papillomavirus (HPV) 16 E7 peptide (HPV16E7 peptide), e.g., amino acid residues 11-19 or 82-90 of HPV16E7, a transmembrane domain, and an intracellular signaling domain. In one embodiment, the extracellular binding domain is an anti-HLA-A2:HPV16E7 antigen-binding protein or an antigen-binding fragment thereof. Exemplary anti-HLA-A2:HPV16E7 antigen-binding proteins of the present invention are any of the antigen-binding proteins described herein.

For example, in certain embodiments, the antigen-binding protein suitable for use in the CARs of the invention comprises three heavy chain complementarity determining regions (CDRs) (HCDR1, HCDR2 and HCDR3) contained within any one of the heavy chain variable region (HCVR) sequences listed in Table 1; and three light chain CDRs (LCDR1, LCDR2 and LCDR3) contained within any one of the light chain variable region (LCVR) sequences listed in Table 1.

In other embodiments, the antigen-binding protein suitable for use in the CARs of the invention comprises a HCVR having an amino acid sequence selected from the group consisting of HCVR sequences listed in Table 1; and/or a LCVR having an amino acid sequence selected from the group consisting of LCVR sequences listed in Table 1.

In some embodiments, the antigen-binding protein suitable for use in the CARs of the invention comprises (a) a HCVR having an amino acid sequence selected from the group consisting of HCVR sequences listed in Table 1; and (b) a LCVR having an amino acid sequence selected from the group consisting of LCVR sequences listed in Table 1.

In one embodiments, the antigen-binding protein suitable for use in the CARs of the invention comprises (a) a HCDR1 domain having an amino acid sequence selected from the group consisting of SEQ ID NOs: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524; (b) a HCDR2 domain having an amino acid sequence selected from the group consisting of SEQ ID NOs: 6, 22, 38, 54, 70, 86, 102, 118, 134, 150, 166, 182, 198, 214, 222, 238, 254, 270, 286, 302, 318, 334, 350, 366, 382, 398, 414, 430, 446, 462, 478, 494, 510, and 526; (c) a HCDR3 domain having an amino acid sequence selected from the group consisting of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528; (d) a LCDR1 domain having an amino acid sequence selected from the group consisting of SEQ ID NOs: 12, 28, 44, 60, 76, 92, 108, 124, 140, 156, 172, 188, 204, 228, 244, 260, 276, 292, 308, 324, 340, 356, 372, 388, 404, 420, 436, 452, 468, 484, 500, 516, and 532; (e) a LCDR2 domain having an amino acid sequence selected from the group consisting of SEQ ID NOs: 14, 30, 46, 62, 78, 94, 110, 126, 142, 158, 174, 190, 206, 230, 246, 262, 278, 294, 310, 326, 342, 358, 374, 390, 406, 422, 438, 454, 470, 486, 502, 518, and 534; and (f) a LCDR3 domain having an amino acid sequence selected from the group consisting of SEQ ID NOs: 16. 32, 48, 64, 80, 96, 112, 128, 144, 160, 176, 192, 208, 232, 248, 264, 280, 296, 312, 328, 344, 360, 376, 392, 408, 424, 440, 456, 472, 488, 504, 520, and 536.

In further embodiment, the antigen-binding protein suitable for use in the CARs of the invention comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530, such as an HCVR/LCVR amino acid sequence pair selected from the group consisting of SEQ ID NOs: 2/10, 34/42, 82/90, 194/202, 282/290, and 506/514.

In some embodiments the isolated antigen-binding protein for use in the CARs of the present invention is an scFv.

In other aspects, the present invention provides vectors comprising the isolated CAR nucleic acid molecules; and immune effector cells comprising such vectors.

In yet other aspects of the present invention, methods for treating a subject having a HPV-associated disease or disorder, such as an HPV16E7-positive cancer, e.g., squamous cell carcinoma, e.g., cervical cancer, head and neck small cell carcinoma, anogenital cancer, and oropharyngeal cancer are provided. The methods include administering to the subject a population of immune effector cells comprising a CAR of the invention.

In some aspects, the present invention provides methods for detecting HPV16E7-positive cells, e.g., in a subject or in a sample obtained from a subject. The methods include contacting a cell, such as a cell sample obtained from a subject, or administering to a subject, an antigen-binding protein of the invention comprising a detectable moiety, and detecting the presence of the detectable moiety.

Other embodiments will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

The term "human papilloma virus" ("HPV") refers to a small, non-enveloped deoxyribonucleic acid (DNA) virus that infects skin or mucosal cells. The circular, double-stranded viral genome is approximately 8-kb in length. The genome encodes for 6 early proteins responsible for virus replication and 2 late proteins, L1 and L2, which are the viral structural proteins. There are over 170 types of HPV that have been identified, and they are designated by numbers. Some HPV types, such as HPV-5, may establish infections that persist for the lifetime of the individual without ever manifesting any clinical symptoms. HPV types 1 and 2 can cause common warts in some infected individuals. HPV types 6 and 11 can cause genital warts and respiratory papillomatosis. HPV types 16, 18, 31, 33, 35, 39, 45, 51, 52, 56, 58, 59, 68, 73, and 82 are considered carcinogenic.

The term "HPV16E7" refers to the HPV type 16 early gene, designated E7, and the protein translated from the gene.

The amino acid sequence of full-length HPV16E7 is provided in Gen Bank as accession number NP_041326.1 (SEQ ID NO: 537). The term "HPV16E7" includes recombinant HPV16E7 or a fragment thereof. The term also encompasses HPV16E7 or a fragment thereof coupled to, for example, histidine tag, mouse or human Fc, or a signal sequence such as ROR1. In certain embodiments, the term comprises HPV16E7 or a fragment thereof in the context of HLA-A2, linked to HLA-A2 or as displayed by HLA-A2.

The term "HLA" refers to the human leukocyte antigen (HLA) system or complex, which is a gene complex encoding the major histocompatibility complex (MHC) proteins in humans. These cell-surface proteins are responsible for the regulation of the immune system in humans. HLAs corresponding to MHC class I (A, B, and C) present peptides from inside the cell.

The term "HLA-A" refers to the group of human leukocyte antigens (HLA) that are coded for by the HLA-A locus. HLA-A is one of three major types of human MHC class I cell surface receptors. The receptor is a heterodimer, and is composed of a heavy α chain and smaller β chain. The α chain is encoded by a variant HLA-A gene, and the β chain (β2-microglobulin) is an invariant β2 microglobulin molecule.

The term "HLA-A2" is one particular class I major histocompatibility complex (MHC) allele group at the HLA-A locus; the α chain is encoded by the HLA-A*02 gene and the R chain is encoded by the β2-microglobulin or B2M locus.

The term "antigen-binding protein," "binding protein" or "binding molecule," as used herein includes molecules that contain at least one antigen-binding site that specifically binds to a molecule of interest, such as a conformational epitope of an HLA-A2 presented human papillomavirus (HPV) 16 E7 peptide (HPV16E7 peptide), e.g., a HLA-A2-displayed peptide comprising amino acid residues 11-19 or 82-90. A binding protein may be an antibody, such as a full-length antibody, or an antigen-binding fragment of an antibody, or a chimeric antigen receptor (CAR), or any other polypeptide, e.g., a receptor-antibody (Rab) protein.

The term "HLA-A2:HPV16E7 antigen-binding protein" or "HLA-A2:HPV16E7 antigen-binding protein," or the like, refers to the an antigen-binding protein, such as an antibody, or antigen-binding portion thereof, that specifically binds to a conformational epitope by the presentation of a peptide fragment of HPV16E7, e.g., amino acid residues 11-19 or amino acid residues 82-90), by HLA-A2. In certain embodiments, the conformational epitope is created on the surface of a cell by the HLA-A2-presented HPV16E7 peptide.

The term "epitope" refers to an antigenic determinant that interacts with a specific antigen-binding site in the variable region of an antigen-binding protein known as a paratope. A single antigen may have more than one epitope. Thus, different antigen-binding proteins may bind to different areas on an antigen and may have different biological effects. The term "epitope" also refers to a site on an antigen to which B and/or T cells respond. It also refers to a region of an antigen that is bound by an antigen-binding protein. Epitopes may be defined as structural or functional. Functional epitopes are generally a subset of the structural epitopes and have those residues that directly contribute to the affinity of the interaction. Epitopes may also be "conformational," that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

In some embodiments of the invention, a binding protein is an antibody, or an antigen-binding fragment thereof, such as a full-length antibody, or antigen-binding fragment thereof.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen-binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antigen binding proteins, such as antibodies, have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The anti-HLA-A2:HPV16E7 antigen-binding proteins, e.g., fully human anti-HLA-A2:HPV16E7 monoclonal antibodies, or antigen-binding fragments thereof, or CARs, disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antigen-binding proteins, e.g., antibodies, or antigen-binding fragments thereof, or CARs, which are derived from any of the amino acid sequences disclosed herein, wherein one or more amino acids within one or more framework and/or CDR regions are mutated to the corresponding residue(s) of the germline sequence from which the antigen-binding protein was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antigen-binding proteins, e.g., antibodies, or antigen-binding fragments thereof, or CARs, which comprise one or more individual germline mutations or combinations thereof. In certain embodiments, all of the framework and/or CDR residues within the $V_H$ and/or $V_L$ domains are mutated back to the residues found in the original germline sequence from which the antigen-binding protein, e.g., antibody, was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antigen-binding proteins, e.g., antibodies, or antigen-binding fragments thereof, or CARs, of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding proteins, e.g., antibodies and antigen-binding fragments, that contain one or more germline mutations can be easily tested for one or more desired property such as, improved binding specificity, increased binding affinity, improved or enhanced antagonistic or agonistic biological properties (as the case may be), reduced immunogenicity, etc. Antigen binding proteins, e.g., antibodies, or antigen-binding fragments thereof, or CARs, obtained in this general manner are encompassed within the present invention.

The present invention also includes antigen-binding proteins, e.g., fully human anti-HLA-A2:HPV16E7 monoclonal antibodies, or antigen-binding fragments thereof, or CARs, comprising variants of any of the HCVR, LCVR, and/or CDR amino acid sequences disclosed herein having one or more conservative substitutions. For example, the present invention includes anti-HLA-A2:HPV16E7 antigen-binding proteins having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human monoclonal antibodies (mAbs) of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antigen-binding proteins, e.g., antibodies or antigen-binding fragments thereof, of the invention created, expressed, isolated or obtained by technologies or methods known in the art as recombinant DNA technology which include, e.g., DNA splicing and transgenic expression. The term refers to antigen-binding proteins, e.g., antibodies expressed in a non-human mammal (including transgenic non-human mammals, e.g., transgenic mice), or a cell (e.g., CHO cells) expression system or isolated from a recombinant combinatorial human antibody library.

As used herein, the terms "chimeric antigen receptor" or "CAR", used interchangeably herein, refer to a recombinant fused protein comprising an extracellular domain capable of binding to an antigen (e.g., a conformational epitope of an HLA-A2 displayed HPV16E7 peptide, e.g., a peptide comprising amino acid residues 11-19 or 82-90 of HPV16E7), a transmembrane domain, and at least one intracellular signaling domain.

An "immune effector cell," as used herein, refers to any cell of the immune system that has one or more effector functions (e.g., cytotoxic cell killing activity, secretion of cytokines, induction of ADCC and/or CDC). In one embodiment, the immune effector cells used with the CARs as described herein are T lymphocytes, in particular cytotoxic T cells (CTLs; CD8+ T cells) and helper T cells (HTLs; CD4+ T cells). Other populations of T cells are also useful herein, for example naïve T cells and memory T cells. As would be understood by the skilled person, other cells may also be used as immune effector cells with the CARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in this regard, immune effector cell includes progenitors of immune effectors cells such as hematopoietic stem cells (HSCs) contained within the CD34+ population of cells derived from cord blood, bone marrow or mobilized peripheral blood which upon administration in a subject differentiate into mature immune effector cells, or which can be induced in vitro to differentiate into mature immune effector cells.

As disclosed herein, the term "off-target peptide" refers to a peptide that differs by 1, 2, 3, 4, 5 or more amino acids from a target peptide (e.g., HPV16 E7 11-19 peptide). In certain embodiments, the term includes a peptide that differs by less than or equal to 3 amino acids than the target peptide. For example, for a 9-mer peptide, if 1, 2, or 3 amino acids are not identical to the target peptide, it is considered an "off-target" peptide. In certain embodiments, amino acid identity is expressed in terms of 'degree of similarity' (DoS). If 6 or more amino acids within a 9-mer peptide are identical, the DoS is 6. In certain embodiments, a peptide with DoS 6 is considered an "off-target" peptide. The term "off-target" peptide also refers to a peptide that is similar to the target peptide based on sequence homology, is predicted to bind to HLA-A2 and is comprised in a protein that is expressed in essential, normal tissues.

The term "specifically binds," or "binds specifically to", or the like, means that an antigen-binding protein, e.g., antibody, or antigen-binding fragments thereof, or CAR, forms a complex with an antigen that is relatively stable under physiologic conditions. Specific binding can be characterized by an equilibrium dissociation constant of at least about $1 \times 10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antigen-binding proteins, e.g., antibodies, have been identified by surface plasmon resonance, e.g., BIACORE™, which bind specifically to a conformational epitope of an HLA-A2 presented human papillomavirus (HPV) 16 E7 peptide (HPV16E7 peptide), e.g., a peptide comprising amino acid residues 11-19 or 82-90 of HPV16E7.

The term "high affinity" antigen-binding protein, e.g., antibody, refers to those antigen-binding proteins, e.g., mAbs, having a binding affinity to conformational epitope of an HLA-A2 presented HPV16E7 peptide, e.g., a peptide comprising amino acid residues 11-19 or 82-90 of HPV16E7, expressed as $K_D$, of at least $10^{-8}$ M; preferably $10^{-9}$M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antigen-binding protein that dissociates from HLA-A2:HPV16E7, with a rate constant of $1 \times 10^{-3}$ s$^{-1}$ or less, preferably $1 \times 10^{4}$ s$^{-1}$ or less, as determined by surface plasmon resonance, e.g., BIACORE™.

The terms "antigen-binding portion" of an antigen-binding protein (e.g., antibody), "antigen-binding fragment" of an antigen-binding protein (e.g., antibody), and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to conformational epitope of an HLA-A2 presented HPV16E7 peptide, e.g., a peptide comprising amino acid residues 11-19 or 82-90 of HPV16E7 coupled to HLA-A2.

In specific embodiments, antigen-binding proteins, e.g., antibody or antibody fragments, or CARs, of the invention may be conjugated to a moiety such as a ligand, a detectable moiety, or a therapeutic moiety ("immunoconjugate"), such as a cytotoxin, a second anti-HLA-A2:HPV16E7 antigen-binding protein, an antibody to a tumor-specific antigen, an anti-cancer drug, or any other therapeutic moiety useful for treating a disease or condition including HPV-associated disease or disorder, such as an HPV16E7-positive cancer or HPV infection including chronic HPV infection.

An "isolated antigen-binding protein", e.g., an isolated antibody, as used herein, is intended to refer to an antigen-binding protein, e.g., antibody, that is substantially free of other antigen-binding proteins, e.g., antibodies (Abs), having different antigenic specificities (e.g., an isolated antibody that specifically binds HLA-A2:HPV16E7, or a fragment thereof, is substantially free of antigen-binding proteins, e.g., antibodies, that specifically bind antigens other than a conformational epitope of an HLA-A2 presented HPV16E7 peptide.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antigen-binding protein-antigen interaction.

The term "cross-competes", as used herein, means an antigen-binding protein, e.g., antibody or antigen-binding fragment thereof, binds to an antigen and inhibits or blocks the binding of another antigen-binding protein, e.g., antibody or antigen-binding fragment thereof. The term also includes competition between two antigen-binding proteins, e.g., antibodies, in both orientations, i.e., a first antigen-binding protein, e.g., antibody, that binds and blocks binding of second antigen-binding protein, e.g., antibody, and vice-versa. In certain embodiments, the first antigen-binding protein, e.g., antibody, and second antigen-binding protein, e.g., antibody, may bind to the same epitope. Alternatively, the first and second antigen-binding proteins, e.g., antibodies, may bind to different, but overlapping epitopes such that binding of one inhibits or blocks the binding of the second, e.g., via steric hindrance. Cross-competition between antigen-binding proteins, e.g., antibodies, may be measured by methods known in the art, for example, by a real-time, label-free bio-layer interferometry assay. Cross-competition between two antigen-binding proteins, e.g., antibodies, may be expressed as the binding of the second antigen-binding protein, e.g., antibody, that is less than the background signal due to self-self binding (wherein first and second antigen-binding proteins, e.g., antibodies, is the same antigen-binding protein, e.g., antibody). Cross-competition between 2 antigen-binding proteins, e.g., antibodies, may be expressed, for example, as % binding of the second antigen-binding protein, e.g., antibody, that is less than the baseline self-self background binding (wherein first and second antigen-binding proteins, e.g., antibodies is the same antigen-binding protein, e.g., antibody).

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

Sequence identity can be calculated using an algorithm, for example, the Needleman Wunsch algorithm (Needleman and Wunsch 1970, *J. Mol. Biol.* 48: 443-453) for global alignment, or the Smith Waterman algorithm (Smith and Waterman 1981, *J. Mol. Biol.* 147: 195-197) for local alignment. Another preferred algorithm is described by Dufresne et al in Nature Biotechnology in 2002 (vol. 20, pp. 1269-71) and is used in the software GenePAST (GQ Life Sciences, Inc. Boston, MA).

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 96%, 97%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) *Methods Mol. Biol.* 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra).

Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215: 403-410 and (1997) *Nucleic Acids Res.* 25:3389-3402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) *The Art, Science and Technology of Pharmaceutical Compounding*).

As used herein, the term "subject" refers to an animal, preferably a mammal, in need of amelioration, prevention and/or treatment of a disease or disorder such as HPV infection, or a HPV-associated disease or disorder, such as a HPV-associated cancer (e.g., an HPV16E7-positive cancer). The term includes human subjects who have or are at risk of having HPV-associated disease or disorder, such as an HPV-associated cancer, metastatic HPV-associated cancer or HPV infection.

As used herein, "anti-cancer drug" means any agent useful to treat or ameliorate or inhibit cancer including, but not limited to, cytotoxins and agents such as antimetabolites, alkylating agents, anthracyclines, antibiotics, antimitotic agents, procarbazine, hydroxyurea, asparaginase, corticosteroids, cyclophosphamide, mytotane (O,P'-(DDD)), biologics (e.g., antibodies and interferons) and radioactive agents. As used herein, "a cytotoxin or cytotoxic agent", also refers to a chemotherapeutic agent and means any agent that is detrimental to cells. Examples include Taxol® (paclitaxel), temozolamide, cytochalasin B, gramicidin D, ethidium bromide, emetine, cisplatin, mitomycin, etoposide, tenoposide, vincristine, vinbiastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

As used herein, the term "anti-viral drug" refers to any drug or therapy used to treat, prevent, or ameliorate a viral infection in a host subject. The term "anti-viral drug" includes, but is not limited to zidovudine, lamivudine, abacavir, ribavirin, lopinavir, efavirenz, cobicistat, tenofovir, rilpivirine, analgesics and corticosteroids.

An immunogen comprising any one of the following can be used to generate antigen-binding proteins, e.g., antibodies, to a conformational epitope of an HLA-A2 presented HPV16E7 peptide, e.g., a peptide comprising amino acid residues 11-19 or residues 82-90 of HPV16E7 linked to HLA-A2. In certain embodiments, the antigen-binding proteins, e.g., antibodies, of the invention are obtained from mice immunized with a full length native HPV16E7 protein (See NCBI accession number NP_041326.1) (SEQ ID NO: 537) or with a recombinant HPV16E7 peptide, such as a peptide comprising either amino acids residues 11-19 (YMLDLQPET; SEQ ID NO: 538) of GenBank Accession NP_041326.1 (SEQ ID NO: 537) or amino acid residues 82-90 (LLMGTLGIV; SEQ ID NO: 539) of GenBank Accession NP_041326.1 (SEQ ID NO: 537), linked to HLA-A2.

Alternatively, HPV16E7 or a fragment thereof may be produced using standard biochemical techniques and modified in the context of HLA-A2 and used as immunogen.

In some embodiments, the immunogen may be a recombinant HPV16E7 peptide expressed in *E. coli* or in any other eukaryotic or mammalian cells such as Chinese hamster ovary (CHO) cells.

In certain embodiments, antigen-binding proteins that bind specifically a conformational epitope of an HLA-A2 presented HPV16E7 peptide may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of HLA-A2:HPV16E7 specific antigen-binding proteins, e.g., antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

Non-limiting, exemplary in vitro assays for measuring binding activity are illustrated in Examples herein. In Example 4, the binding affinities and kinetic constants of human anti-HLA-A2:HPV16E7 specific antigen-binding proteins, e.g., antibodies were determined by surface plasmon resonance and the measurements were conducted on a Biacore 4000 or T200 instrument. Examples 6 and 7 describe the binding of the antibodies to cells overexpressing fragments of HPV16E7.

The antigen-binding proteins, e.g., antibodies, specific for HLA-A2:HPV16E7 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antigen-binding proteins may be used in diagnostic assays including imaging assays.

Antigen Binding Proteins

The present invention provides antigen-binding proteins that include antibodies, or antigen-binding fragments thereof, and CARs (e.g., nucleic acid molecules encoding a CAR of the invention) (described below). Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to a conformational epitope of an HLA-A2 presented HPV16E7 peptide. An antigen-binding protein, such as an antibody fragment, may include a Fab fragment, a F(ab')$_2$ fragment, a Fv fragment, a dAb fragment, a fragment containing a CDR, or an isolated CDR. Antigen binding proteins, such as antigen-binding fragments of an antibody, may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments of an antibody, include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antigen-binding protein (e.g., antibody), will typically comprise at least one variable domain. The variable domain may be of any size or amino acid composition and will generally comprise at least one CDR, which is adjacent to or in frame with one or more framework sequences. In antigen-binding proteins having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody, may contain a monomeric $V_H$ or $V_L$ domain.

In certain embodiments, an antigen-binding fragment of an antibody, may contain at least one variable domain covalently linked to at least one constant domain. Non-limiting, exemplary configurations of variable and constant domains that may be found within an antigen-binding fragment of an antigen-binding protein of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; $V_H$-$C_H2$-$C_H3$; (Vii) $V_H$-$C_L$; $V_L$-$C_H1$; (ix) $V_L$-$C_H2$; (X) $V_L$-$C_H3$; (xi) $V_L$-$C_H1$-$C_H2$; (XII) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody, of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding proteins, e.g., antigen-binding fragments of an antibody, may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Antigen-Binding Proteins

Methods for generating antigen-binding proteins, such as human antibodies, in transgenic mice are known in the art. Any such known methods can be used in the context of the present invention to make human antibodies that specifically bind to a conformational epitope of an HLA-A2 presented human papillomavirus (HPV) 16 E7 peptide (HPV16E7 peptide).

Using VELOCIMMUNE® technology (see, for example, U.S. Pat. No. 6,596,541, Regeneron Pharmaceuticals, VELOCIMMUNE®) or any other known method for generating antigen-binding proteins, e.g., monoclonal antibodies, high affinity antigen-binding proteins, e.g., chimeric antibodies, to conformational epitope of an HLA-A2 presented HPV16E7 peptide, are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antigen-binding protein, e.g., antibody, comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antigen-binding proteins, e.g., antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antigen-binding protein may be produced in a cell, such as a CHO cell. Alternatively, DNA encoding the antigen-specific antigen-binding proteins, e.g., chimeric antibodies, or the variable domains of the light and heavy chains may be isolated directly from antigen-specific lymphocytes.

Initially, high affinity antigen-binding proteins, e.g., chimeric antibodies, are isolated having a human variable region and a mouse constant region. As in the experimental section below, the antigen-binding proteins are characterized and selected for desirable characteristics, including affinity, selectivity, epitope, etc. The mouse constant regions are replaced with a desired human constant region to generate the antigen-binding proteins, e.g., fully human antibodies, of the invention, for example wild-type or modified IgG1 or IgG4. While the constant region selected may vary according to specific use, high affinity antigen-binding and target specificity characteristics reside in the variable region.

Bioequivalents

The anti-HLA-A2:HPV16E7 antigen-binding proteins of the present invention encompass proteins having amino acid sequences that vary from those of the described antigen-binding proteins, e.g., antibodies, but that retain the ability to bind a conformational epitope of an HLA-A2 presented HPV16E7 peptide. Such variant antigen-binding proteins comprise one or more additions, deletions, or substitutions of amino acids when compared to parent sequence, but exhibit biological activity that is essentially equivalent to that of the described antigen-binding proteins. Likewise, the antigen-binding protein-encoding DNA sequences of the present invention encompass sequences that comprise one or more additions, deletions, or substitutions of nucleotides when compared to the disclosed sequence, but that encode an antigen-binding protein that is essentially bioequivalent to an antigen-binding protein of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antigen-binding proteins or antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins (or antibodies) are bioequivalent if there are no clinically meaningful differences in their safety, purity, or potency.

In one embodiment, two antigen-binding proteins (or antibodies) are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins (or antibodies) are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antigen-binding protein or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antigen-binding protein (or its target) is measured as a function of time; and (d) in a well-controlled clinical trial that establishes safety, efficacy, or bioavailability or bioequivalence of an antigen-binding protein.

Bioequivalent variants of the antigen-binding proteins (or antibodies) of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include antigen-binding protein variants comprising amino acid changes, which modify the glycosylation characteristics of the antigen-binding proteins, e.g., mutations that eliminate or remove glycosylation.

Anti-HLA-A2:HPV16E7 Antigen Binding-Proteins Comprising Fc Variants

According to certain embodiments of the present invention, anti-HLA-A2:HPV16E7 antigen-binding proteins, e.g., antibodies, are provided comprising an Fc domain comprising one or more mutations which enhance or diminish antigen-binding protein binding to the FcRn receptor, e.g., at acidic pH as compared to neutral pH. For example, the present invention includes anti-HLA-A2:HPV16E7 antigen-binding proteins comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antigen-binding protein when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-HLA-A2:HPV16E7 antigen-binding proteins comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and O311I); 257I and 434H (e.g., P257I and N434H); 376V and 434H (e.g., D376V and N434H); 307A, 380A and 434A (e.g., 1307A, E380A and N434A); and 433K and 434F (e.g., H433K and N434F). In one embodiment, the present invention includes anti-HLA-A2:HPV16E7 antigen-binding proteins comprising an Fc domain comprising a S108P mutation in the hinge region of IgG4 to promote dimer stabilization. All possible combinations of the foregoing Fc domain mutations, and other mutations within the antigen-binding protein variable domains disclosed herein, are contemplated within the scope of the present invention.

The present invention also includes anti-HLA-A2:HPV16E7 antigen-binding proteins comprising a chimeric heavy chain constant ($C_H$) region, wherein the chimeric $C_H$ region comprises segments derived from the $C_H$ regions of more than one immunoglobulin isotype. For example, the antigen-binding proteins of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antigen-binding proteins of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antigen-binding protein comprising a chimeric $C_H$ region as described herein may, in certain embodiments, exhibit modified Fc effector functions without adversely affecting the therapeutic or pharmacokinetic properties of the antigen-binding protein. (See, e.g., U.S. Patent Publication No. 20140243504, the disclosure of which is hereby incorporated by reference in its entirety).

Biological Characteristics of the Antigen-Binding Proteins

In general, the antigen-binding proteins of the present invention function by binding to a conformational epitope of an HLA-A2 presented human papillomavirus (HPV) 16 E7 peptide (HPV16E7) peptide.

The present invention includes anti-HLA-A2:HPV16E7 antigen-binding proteins that bind HPV16E7 peptide in the context of HLA-A2 with high specificity. The anti-HLA-A2:HPV16E7 antigen-binding proteins do not bind to the HPV16E7 peptide in the absence of HLA-A2. Further, the anti-HLA-A2:HPV16E7 antigen-binding proteins do not bind to an off-target peptide in the context of HLA-A2.

The present invention includes anti-HLA-A2:HPV16E7 antigen-binding proteins that bind monomeric HLA-A2:HPV16E7 11-19 peptide with high affinity. For example, the present invention includes antigen-binding proteins that bind monomeric HLA-A2:HPV16E7 11-19 peptide (e.g., at 25° C. or at 37° C.) with a $K_D$ of less than about 20 nM as measured by surface plasmon resonance, e.g., using the assay format as defined in Example 4 herein. In certain embodiments, the antigen-binding proteins bind monomeric HLA-A2:HPV16E7 11-19 peptide with a $K_D$ of less than about 15 nM, less than about 12 nM, less than about 10 nM, less than about 5 nM, less than about 2 nM, less than about 1 nM, less than about 0.5 nM less than about 0.1 nM, less than about 0.05 nM or less than about 0.04 nM, as measured by surface plasmon resonance, e.g., using the assay format as defined in Example 4 herein, or a substantially similar assay.

The present invention includes antigen-binding proteins that bind monomeric HLA-A2:HPV16E7 82-90 peptide (e.g., at 25° C. or at 37° C.) with a $K_D$ of less than about 25 nM as measured by surface plasmon resonance, e.g., using the assay format as defined in Example 4 herein, or a substantially similar assay. In certain embodiments, the antigen-binding proteins bind monomeric HLA-A2:HPV16E7 82-90 peptide with a $K_D$ of less than about 20 nM, less than about 15 nM, less than about 12 nM, less than about 10 nM, less than about 5 nM, less than about 2 nM, less than about 1 nM, less than about 0.5 nM less than about 0.1 nM, less than about 0.05 nM or less than about 0.04 nM, as measured by surface plasmon resonance, e.g., using the assay format as defined in Example 4 herein, or a substantially similar assay.

The present invention also includes antigen-binding proteins that bind to a cell expressing an HLA-A2:HPV16E7 11-19 peptide with an $EC_{50}$ less than about 6 nM and do not bind to cells expressing predicted off-target peptides as determined by luminescence assay, as defined in Example 6 herein, or a substantially similar assay. In certain embodiments, the antigen-binding proteins bind to a cell expressing an HLA-A2:HPV16E7 11-19 peptide with an $EC_{50}$ less than about less than about 6 nM, less than about 5 nM, less than about 2 nM, less than about 1 nM, or less than about 0.5 nM, and do not bind to cells expressing predicted off-target peptides as determined by luminescence assay, as defined in Example 6 herein, or a substantially similar assay. e.g., using the assay format in Example 6 herein, or a substantially similar assay.

The present invention also includes antigen-binding proteins that bind to a cell expressing an HLA-A2:HPV16E7 82-90 peptide with an $EC_{50}$ less than about 1 nM and do not bind to cells expressing predicted off-target peptides as determined by luminescence assay, as defined in Example 6 herein, or a substantially similar assay. In certain embodiments, the antigen-binding proteins bind to a cell expressing an HLA-A2:HPV16E7 82-90 peptide with an $EC_{50}$ less than about less than about 1 nM, less than about 0.5 nM, less than about 0.2 nM, or less than about 0.01 nM and do not bind to cells expressing predicted off-target peptides as determined by luminescence assay, as defined in Example 6 herein, or a substantially similar assay. e.g., using the assay format in Example 6 herein, or a substantially similar assay.

The present invention also includes antigen-binding proteins that bind to a cell expressing an HLA-A2:HPV16E7 11-19 peptide with an $EC_{50}$ less than about 30 nM as measured by a flow cytometry assay as defined in Example 7 herein, or a substantially similar assay. In certain embodiments, the antigen-binding proteins bind to a cell expressing an HLA-A2:HPV16E7 11-19 peptide with an $EC_{50}$ less than about 25 nM, less than about 20 nM, less than about 15 nM, less than about 10 nM, less than about 5 nM, less than about 2 nM, less than about 1 nM, or less than about 0.5 nM, as measured by a flow cytometry assay, e.g., using the assay format in Example 7 herein, or a substantially similar assay.

The present invention also includes antigen-binding proteins that bind to a cell expressing an HLA-A2:HPV16E7 82-90 peptide with an $EC_{50}$ less than about 75 nM as measured by a flow cytometry assay as defined in Example 7 herein, or a substantially similar assay. In certain embodiments, the antigen-binding proteins bind to a cell expressing an HLA-A2:HPV16E7 82-90 peptide with an $EC_{50}$ less than about 75 nM, less than about 70 nM, less than about 65 nM, less than about 60 nM, less than about 55 nM, less than about 50 nM, less than about 45 nM, less than about 40 nM, less than about 35 nM, less than about 30 nM, less than about 25 nM, less than about 20 nM, less than about 15 nM, less than about 10 nM, less than about 5 nM, less than about 2 nM, less than about 1 nM, or less than about 0.5 nM, as measured by a flow cytometry assay, e.g., using the assay format in Example 7 herein, or a substantially similar assay.

In certain embodiments, the antigen-binding proteins of the present invention are useful in inhibiting the growth of a tumor or delaying the progression of cancer when administered prophylactically to a subject in need thereof and may increase survival of the subject. For example, the administration of an antigen-binding protein of the present invention may lead to shrinking of a primary tumor and may prevent metastasis or development of secondary tumors. In certain embodiments, the antigen-binding proteins of the present invention are useful in inhibiting the growth of a tumor when administered therapeutically to a subject in need thereof and may increase survival of the subject. For example, the administration of a therapeutically effective amount of an antigen-binding protein of the invention to a subject may lead to shrinking and disappearance of an established tumor in the subject.

In one embodiment, the invention provides an isolated recombinant antigen-binding protein thereof that binds to a conformational epitope of an HLA-A2 presented HPV16E7 peptide, wherein the antigen-binding protein exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 218, 234, 250, 266, 282, 298, 314, 330, 346, 362, 378, 394, 410, 426, 442, 458, 474, 490, 506, and 522, or a substantially similar sequence thereof having at least 90%, at least 95%, at least 96%, at least 97%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 226, 242, 258, 274, 290, 306, 322, 338, 354, 370, 386, 402, 418, 434, 450, 466, 482, 498, 514, and 530, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528, or a substantially similar sequence thereof having at least 90%, at least 95%, at least 96%, at least 97%, at least 98% or at least 99% sequence identity; and a LCDR3 domain having an amino acid sequence selected from the group consisting of SEQ ID NO: 16, 32, 48, 64, 80, 96, 112, 128, 144,160, 176, 192, 208, 232, 248, 264, 280, 296, 312, 328, 344, 360, 376, 392, 408, 424, 440, 456, 472, 488, 504, 520, and 536, or a substantially similar sequence thereof having at least 90%, at least 95%, at least 96%, at least 97%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 220, 236, 252, 268, 284, 300, 316, 332, 348, 364, 380, 396, 412, 428, 444, 460, 476, 492, 508, and 524, or a substantially similar sequence thereof having at least 90%, at least 95%, at least 96%, at least 97%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 228, 244, 260, 276, 292, 308, 324, 340, 356, 372, 388, 404, 420, 436, 452, 468, 484, 500, 516, and 532, or a substantially similar sequence thereof having at least 90%, at least 95%, at least 96%, at least 97%, at least 98% or at least 99% sequence identity; and a LCDR2 domain having an amino acid sequence selected from the group consisting of SEQ ID NO: 14, 30, 46, 62, 78, 94, 110, 126, 142, 158,174, 190, 206, 230, 246, 262, 278, 294, 310, 326, 342, 358, 374, 390, 406, 422, 438, 454, 470, 486, 502, 518, and 534, or a substantially similar sequence thereof having at least 90%, at least 95%, at least 96%, at least 97%, at least 98% or at least 99% sequence identity; (v) binds monomeric HLA-A2:HPV16E7 11-19 peptide with a binding dissociation equilibrium constant (KD) of less than about 20 nM as measured in a surface plasmon resonance assay at 25° C.; (vi) binds monomeric HLA-A2:HPV16E7 82-90 peptide with a binding dissociation equilibrium constant (KD) of less than about 25 nM as measured in a surface plasmon resonance assay at 25° C.; (vii) binds to HLA-A2:HPV16E7 11-19 peptide expressing cells with an $EC_{50}$ less than about 6 nM and do not bind to cells expressing predicted off-target peptides as determined by luminescence assay; (viii) binds to HLA-A2:HPV16E7 82-90 peptide expressing cells with an $EC_{50}$ less than about 1 nM and do not substantially bind to cells expressing predicted off-target peptides as determined by luminescence assay; (ix) binds to HLA-A2:HPV16E7 11-19 peptide expressing cells with an $EC_{50}$ less than about 30 nM as determined by flow cytometry assay; (x) binds to HLA-A2:HPV16E7 82-90 peptide expressing cells with an $EC_{50}$ less than about 75 nM as determined by flow cytometry assay; (xi) does not bind to a HLA-A2-displayed off-target peptide wherein the peptide differs by 1, 2, 3, 4, 5 or more amino acids from SEQ ID NO: 538; and (xii) does not bind to a HLA-A2-displayed off-target peptide wherein the peptide differs by 1, 2, 3, 4, 5 or more amino acids from SEQ ID NO: 539.

The antigen-binding proteins of the present invention may possess one or more of the aforementioned biological characteristics, or any combinations thereof. Other biological characteristics of the antigen-binding proteins of the present invention will be evident to a person of ordinary skill in the art from a review of the present disclosure including the working Examples herein.

Epitope Mapping and Related Technologies

The present invention includes anti-HLA-A2:HPV16E7 antigen-binding proteins which interact with one or more amino acids found within one or more domains of the HLA-A2 displayed HPV16E7 peptide. The epitope may consist of a plurality of non-contiguous amino acids (or amino acid sequences) located within either or both of the aforementioned domains of the HPV16E7 molecule (e.g. a conformational epitope).

Various techniques known to persons of ordinary skill in the art can be used to determine whether an antigen-binding protein "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, NY). Other methods include alanine scanning mutational analysis, peptide blot analysis (Reineke (2004) Methods Mol. Biol. 248: 443-63), peptide cleavage analysis crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein interacts is hydrogen/deuterium exchange detected by mass spectrometry. In general terms, the hydrogen/deuterium exchange method involves deuterium-labeling the protein of interest, followed by binding the antigen-binding protein to the deuterium-labeled protein. Next, the protein/antigen-binding protein complex is transferred to water and exchangeable protons within amino acids that are protected by the antigen-binding protein complex undergo deuterium-to-hydrogen back-exchange at a slower rate than exchangeable protons within amino acids that are not part of the interface. As a result, amino acids that form part of the protein/antigen-binding protein interface may retain deuterium and therefore exhibit relatively higher mass compared to amino acids not included in the interface. After dissociation of the antigen-binding protein, the target protein is subjected to protease cleavage and mass spectrometry analysis, thereby revealing the deuterium-labeled residues which correspond to the specific amino acids with which the antigen-binding protein interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antigen-binding proteins, e.g., antibodies (mAbs), directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antigen-binding proteins, such that characterization can be focused on genetically distinct antigen-binding proteins. When applied to hybridoma screening, MAP may facilitate identification of rare hybridoma clones that produce antigen-binding proteins having the desired characteristics. MAP may be used to sort the antigen-binding proteins of the invention into groups of antigen-binding proteins binding different epitopes.

The present invention includes anti-HLA-A2:HPV16E7 antigen-binding proteins that bind to the same epitope, or a portion of the epitope, as any of the specific exemplary antigen-binding proteins described herein in Table 1, or an antigen-binding protein having the CDR sequences of any of the exemplary antigen-binding proteins described in Table 1. Likewise, the present invention also includes anti-HLA-A2:HPV16E7 antigen-binding proteins that compete for binding to HLA-A2:HPV16E7 or a fragment thereof with any of the specific exemplary antigen-binding proteins described herein in Table 1, or an antigen-binding protein having the CDR sequences of any of the exemplary antigen-binding proteins described in Table 1.

One can easily determine whether an antigen-binding protein binds to the same epitope as, or competes for binding with, a reference anti-HLA-A2:HPV16E7 antigen-binding protein by using routine methods known in the art. For example, to determine if a test antigen-binding protein binds to the same epitope as a reference anti-HLA-A2:HPV16E7 antigen-binding protein of the invention, the reference antigen-binding protein is allowed to bind to a HLA-A2:HPV16E7 protein or peptide under saturating conditions. Next, the ability of a test antigen-binding protein to bind to the HLA-A2:HPV16E7 molecule is assessed. If the test antigen-binding protein is able to bind to HLA-A2:HPV16E7 following saturation binding with the reference anti-HLA-A2:HPV16E7 antigen-binding protein, it can be concluded that the test antigen-binding protein binds to a different epitope than the reference anti-HLA-A2:HPV16E7 antigen-binding protein. On the other hand, if the test antigen-binding protein is not able to bind to the HLA-A2:HPV16E7 protein following saturation binding with the reference anti-HLA-A2:HPV16E7 antigen-binding protein, then the test antigen-binding protein may bind to the same epitope as the epitope bound by the reference anti-HLA-A2:HPV16E7 antigen-binding protein of the invention.

To determine if an antigen-binding protein competes for binding with a reference anti-HLA-A2:HPV16E7 antigen-binding protein, the above-described binding methodology is performed in two orientations: In a first orientation, the reference antigen-binding protein is allowed to bind to a HLA-A2:HPV16E7 protein under saturating conditions followed by assessment of binding of the test antigen-binding protein to the HLA-A2:HPV16E7 molecule. In a second orientation, the test antigen-binding protein is allowed to bind to a HLA-A2:HPV16E7 molecule under saturating conditions followed by assessment of binding of the reference antigen-binding protein to the HLA-A2:HPV16E7 molecule. If, in both orientations, only the first (saturating) antigen-binding protein is capable of binding to the HLA-A2:HPV16E7 molecule, then it is concluded that the test antigen-binding protein and the reference antigen-binding protein compete for binding to HLA-A2:HPV16E7. As will be appreciated by a person of ordinary skill in the art, an antigen-binding protein that competes for binding with a reference antigen-binding protein may not necessarily bind to the identical epitope as the reference antigen-binding protein, but may sterically block binding of the reference antigen-binding protein by binding an overlapping or adjacent epitope.

Two antigen-binding proteins bind to the same or overlapping epitope if each competitively inhibits (blocks) binding of the other to the antigen. That is, a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990 50:1495-1502). Alternatively, two antigen-binding proteins have the same epitope if essentially all amino acid mutations in the antigen that reduce or eliminate binding of one antigen-binding protein reduce or eliminate binding of the other. Two antigen-binding proteins have overlapping epitopes if some amino acid mutations that reduce or eliminate binding of one antigen-binding protein reduce or eliminate binding of the other.

Additional routine experimentation (e.g., peptide mutation and binding analyses) can then be carried out to confirm whether the observed lack of binding of the test antigen-binding protein is in fact due to binding to the same epitope as the reference antigen-binding protein or if steric blocking (or another phenomenon) is responsible for the lack of observed binding. Experiments of this sort can be performed using ELISA, RIA, surface plasmon resonance, flow cytometry or any other quantitative or qualitative antigen-binding protein-binding assay available in the art.

Immunoconjugates

The invention encompasses anti-HLA-A2:HPV16E7 antigen-binding proteins conjugated to a therapeutic moiety ("immunoconjugate"), such as a cytotoxin or a chemotherapeutic agent to treat cancer. As used herein, the term "immunoconjugate" refers to an antigen-binding protein which is chemically or biologically linked to a cytotoxin, a radioactive agent, a cytokine, an interferon, a target or reporter moiety, such as a detectable moiety, an enzyme, a toxin, a peptide or protein or a therapeutic agent. The antigen-binding protein may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antigen-binding protein-drug conjugates and antigen-binding protein-toxin fusion proteins. In one embodiment, the agent may be a second different antibody to HPV16E7 or HLA-A2:HPV16E7. In certain embodiments, the antigen-binding protein may be conjugated to an agent specific for a tumor cell or a virally infected cell, i.e., an HPV infected cell. The type of therapeutic moiety that may be conjugated to the anti-HLA-A2:HPV16E7 antigen-binding protein and will take into account the condition to be treated and the desired therapeutic effect to be achieved. Examples of suitable agents for forming immunoconjugates are known in the art; see for example, PCT Publication No. WO 05/103081.

Chimeric Antigen Receptors (CAR)

Chimeric antigen receptors (CARs) redirect T cell specificity toward antibody-recognized antigens expressed on the surface of cancer cells, while T cell receptors (TCRs) extend the range of targets to include intracellular tumor antigens. CAR redirected T cells specific for the B cell differentiation antigen CD19 have shown dramatic efficacy in the treatment of B cell malignancies, while TCR-redirected T cells have shown benefits in patients suffering from solid cancer. Stauss et al. describe strategies to modify therapeutic CARs and TCRs, for use in the treatment of cancer, for example, to enhance the antigen-specific effector function and limit toxicity of engineered T cells (*Current Opinion in Pharmacology* 2015, 24:113-118).

One aspect of the invention includes a chimeric antigen receptor (CAR) which is specific for an HPV16E7 peptide displayed on the surface of tumor cells by HLA-A2, such as a peptide comprising amino acid residues 11-19 or 82-90 of HPV16E7. In one embodiment of the present invention, a CAR as described herein comprises an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, CD28, CD137, CD134 or CD278. In one embodiment, the CAR includes a hinge or spacer region between the extracellular binding domain and the transmembrane domain, such as a CD8alpha hinge. In another embodiment of the present invention, a CAR as described herein comprises an extracellular target-specific binding domain, and a T cell receptor constant domain ("T-body construct").

It is to be understood that, for use in any of the CARs described herein, the extracellular target-specific binding domain may comprise a Fab, a Fab', a (Fab')2, an Fv, or a single chain Fv (scFv) of an antigen-binding protein of the invention.

As used herein, the binding domain or the extracellular domain of the CAR, provides the CAR with the ability to bind to the target antigen of interest. A binding domain can be any protein, polypeptide, oligopeptide, or peptide that possesses the ability to specifically recognize and bind to a biological molecule (e.g., a cell surface receptor or tumor protein, or a component thereof). A binding domain includes any naturally occurring, synthetic, semi-synthetic, or recombinantly produced binding partner for a biological molecule of interest. For example, and as further described herein, a binding domain may be antibody light chain and heavy chain variable regions, or the light and heavy chain variable regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE analysis), and are described herein. The target may be any antigen of clinical interest against which it would be desirable to trigger an effector immune response that results in tumor killing. In one embodiment, the target antigen of the binding domain of the chimeric antigen receptor is a conformational epitope of an HLA-A2 presented HPV16E7 peptide on the surface of tumor cells, such as a peptide comprising amino acid residues 11-19 or 82-90 of HPV16E7.

Illustrative binding domains include antigen-binding proteins, such as antigen-binding fragments of an antibody, such as scFv, scTCR, extracellular domains of receptors, ligands for cell surface molecules/receptors, or receptor binding domains thereof, and tumor binding proteins. In certain embodiments, the antigen-binding domains included in a CAR of the invention can be a variable region (Fv), a CDR, a Fab, an scFv, a VH, a VL, a domain antibody variant (dAb), a camelid antibody (VHH), a fibronectin 3 domain variant, an ankyrin repeat variant and other antigen-specific binding domain derived from other protein scaffolds.

In one embodiment, the binding domain of the CAR is an anti-HLA-A2:HPV16E7 single chain antibody (scFv), and may be a murine, human or humanized scFv. Single chain antibodies may be cloned form the V region genes of a hybridoma specific for a desired target. A technique which can be used for cloning the variable region heavy chain (VH) and variable region light chain (VL) has been described, for example, in Orlandi et al., *PNAS,* 1989; 86: 3833-3837. Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen.

In certain embodiments, the CARs of the present invention may comprise a linker between the various domains, added for appropriate spacing and conformation of the molecule. For example, in one embodiment, there may be a linker between the binding domain VH or VL which may be between 1-10 amino acids long. In other embodiments, the linker between any of the domains of the chimeric antigen receptor may be between 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long. Ranges including the numbers described herein are also included herein, e.g., a linker 10-30 amino acids long.

In certain embodiments, linkers suitable for use in the CAR described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers, where n is an integer of at least one, glycine-alanine polymers, alanine-serine polymers, and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains (see Scheraga, *Rev. Computational Chem.* 11173-142 (1992)). The ordinarily skilled artisan will recognize that design of a CAR can include linkers that are all or partially flexible, such that the linker can include a flexible linker as well as one or more portions that confer less flexible structure to provide for a desired CAR structure.

The binding domain of the CAR may be followed by a "spacer," or, "hinge," which refers to the region that moves the antigen-binding domain away from the effector cell surface to enable proper cell/cell contact, antigen-binding and activation (Patel et al., *Gene Therapy,* 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered. In one embodiment, the hinge region comprises a CD8alpha hinge.

The "transmembrane," region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In certain embodiments, the transmembrane domain is synthetic in which case it would comprise predominantly hydrophobic residues such as leucine and valine.

The "intracellular signaling domain," refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen-binding to the extracellular CAR domain. The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRγ chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Primary cytoplasmic signaling sequences regulate primary activation of the T cell receptor complex either an inhibitory way, or in an inhibitory way. Primary cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular used in the invention include those derived from TCRzeta, FcRgamma, FcRbeta, CD3gamma, CD3delta, CD3epsilon, CD5, CD22, CD79a, CD79b and CD66d. In certain particular embodiments, the intracellular signaling domain of the anti-HLA-A2: HPV16E7 CARs described herein are derived from CD3zeta or FcRgamma.

As used herein, the term, "co-stimulatory signaling domain," or "co-stimulatory domain", refers to the portion of the CAR comprising the intracellular domain of a co-stimulatory molecule. Co-stimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1 BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD3zeta and 4-1 BB, other costimulatory domains are contemplated for use with the CARs described herein. The inclusion of one or more co-stimulatory signaling domains may enhance the efficacy and expansion of T cells expressing CAR receptors. The intracellular signaling and co-stimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant co-stimulatory signal. Other CARs containing a binding domain, a hinge, a transmembrane and the signaling domain derived from CD3zeta or FcRgamma together with one or more co-stimulatory signaling domains (e.g., intracellular co-stimulatory domains derived from CD28, CD137, CD134 and CD278) may more effectively direct antitumor activity as well as increased cytokine secretion, lytic activity, survival and proliferation in CAR expressing T cells in vitro, and in animal models and cancer patients (Milone et al., *Molecular Therapy,* 2009; 17: 1453-1464; Zhong et al., *Molecular Therapy,* 2010; 18: 413-420; Carpenito et al., *PNAS,* 2009; 106:3360-3365).

In one embodiment, the HLA-A2:HPV16E7 CARs of the invention comprise (a) an anti-HLA-A2:HPV16E7 scFv as a binding domain (e.g., an scFv having binding regions (e.g., CDRs or variable domains) from any one or more of the HLA-A2:HPV16E7 antibodies described in Table 1) (b) a hinge region derived from human CD8alpha, (c) a human CD8alpha transmembrane domain, and (d) a human T cell receptor CD3 zeta chain (CD3) intracellular signaling domain, and optionally one or more co-stimulatory signaling domains derived from CD28, CD137, CD134, and CD278. In one embodiment, the different protein domains are arranged from amino to carboxyl terminus in the following order: binding domain, hinge region and transmembrane domain. The intracellular signaling domain and optional co-stimulatory signaling domains are linked to the transmembrane carboxy terminus in any order in tandem to form a single chain chimeric polypeptide. In one embodiment, a nucleic acid construct encoding an HLA-A2:HPV16E7 CAR is a chimeric nucleic acid molecule comprising a nucleic acid molecule comprising different coding sequences, for example, (5' to 3') the coding sequences of a human anti-HLA-A2:HPV16E7 scFv, a human CD8alpha-hinge, a human CD8alpha transmembrane domain and a CD3zeta intracellular signaling domain. In another embodiment, a nucleic acid construct encoding an HLA-A2:HPV16E7 CAR is a chimeric nucleic acid molecule comprising a nucleic acid molecule comprising different coding sequences, for example, (5' to 3') the coding sequences of a human anti-HLA-A2:HPV16E7 scFv, a human CD8alpha-hinge, a human CD8alpha transmembrane domain, a CD137 co-stimulatory domain, and a CD3zeta co-stimulatory domain. In certain embodiments, a nucleic acid construct encoding an HLA-A2:HPV16E7 CAR is a chimeric nucleic acid molecule comprising a nucleic acid molecule comprising different coding sequences, for example, (5' to 3') the coding sequences of a human anti-HLA-A2:HPV16E7 scFv, a human CD8alpha-hinge, a human CD8alpha transmembrane domain, a CD137 co-stimulatory domain, and a CD3zeta co-stimulatory domain, wherein the anti-HLA-A2: HPV16E7 scFv comprises a $V_H$ selected from the group consisting of SEQ ID Nos: 2, 34, 82, 194, 282, and 506, and a $V_L$ selected from the group consisting of SEQ ID Nos: 10, 42, 90, 202, 290 and 514. In some embodiments, the present invention includes a nucleic acid molecule that encodes for a HLA-A2:HPV16E7 CAR selected from the group consisting of SEQ ID Nos: 540, 541, 542, 543, 544 and 545.

In certain embodiments, the polynucleotide encoding the CAR described herein is inserted into a vector. The term "vector" as used herein refers to a vehicle into which a polynucleotide encoding a protein may be covalently inserted so as to bring about the expression of that protein and/or the cloning of the polynucleotide. Such vectors may also be referred to as "expression vectors". The isolated polynucleotide may be inserted into a vector using any suitable methods known in the art, for example, without limitation, the vector may be digested using appropriate restriction enzymes and then may be ligated with the isolated polynucleotide having matching restriction ends. Expression vectors have the ability to incorporate and express heterologous or modified nucleic acid sequences coding for at least part of a gene product capable of being transcribed in a cell. In most cases, RNA molecules are then translated into a protein. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra. An expression vector may comprise additional elements, for example, the expression vector may have two replication systems, thus allowing it to be maintained in two organisms, for example in human cells for expression and in a prokaryotic host for cloning and amplification.

The expression vector may have the necessary 5' upstream and 3' downstream regulatory elements such as promoter sequences such as CMV, PGK and EF1alpha. promoters, ribosome recognition and binding TATA box, and 3' UTR AAUAAA transcription termination sequence for the efficient gene transcription and translation in its respective host cell. Other suitable promoters include the constitutive promoter of simian virus 40 (SV40) early promoter, mouse mammary tumor virus (MMTV), HIV LTR promoter, MoMuLV promoter, avian leukemia virus promoter, EBV immediate early promoter, and rous sarcoma virus promoter. Human gene promoters may also be used, including, but not limited to the actin promoter, the myosin promoter, the hemoglobin promoter, and the creatine kinase promoter. In certain embodiments inducible promoters are also contemplated as part of the vectors expressing chimeric antigen receptor. This provides a molecular switch capable of turning on expression of the polynucleotide sequence of interest or turning off expression. Examples of inducible promoters include, but are not limited to a metallothionine promoter, a glucocorticoid promoter, a progesterone promoter, or a tetracycline promoter.

The expression vector may have additional sequence such as 6x-histidine (SEQ ID NO: 594), c-Myc, and FLAG tags which are incorporated into the expressed CARs. Thus, the expression vector may be engineered to contain 5' and 3' untranslated regulatory sequences that sometimes can function as enhancer sequences, promoter regions and/or terminator sequences that can facilitate or enhance efficient transcription of the nucleic acid(s) of interest carried on the expression vector. An expression vector may also be engineered for replication and/or expression functionality (e.g., transcription and translation) in a particular cell type, cell location, or tissue type. Expression vectors may include a selectable marker for maintenance of the vector in the host or recipient cell.

Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are Lenti-X™ Bicistronic Expression System (Neo) vectors (Clontrch), pClneo vectors (Promega) for expression in mammalian cells; pLenti4/V5-DEST™, pLenti6/V5-DEST™, and pLenti6.2N5-GW/lacZ (Invitrogen) for lentivirus-mediated gene transfer and expression in mammalian cells. The coding sequences of the CARs disclosed herein can be ligated into such expression vectors for the expression of the chimeric protein in mammalian cells.

In certain embodiments, the nucleic acids encoding the CAR of the present invention are provided in a viral vectors. A viral vector can be those derived from retrovirus, lentivirus, or foamy virus. As used herein, the term, "viral vector," refers to a nucleic acid vector construct that includes at least one element of viral origin and has the capacity to be packaged into a viral vector particle. The viral vector can contain the coding sequence for a the various chimeric proteins described herein in place of nonessential viral genes. The vector and/or particle can be utilized for the purpose of transferring DNA, RNA or other nucleic acids into cells either in vitro or in vivo. Numerous forms of viral vectors are known in the art.

In certain embodiments, the viral vector containing the coding sequence for a CAR described herein is a retroviral vector or a lentiviral vector. The term "retroviral vector" refers to a vector containing structural and functional genetic elements that are primarily derived from a retrovirus. The term "lentiviral vector" refers to a vector containing structural and functional genetic elements outside the LTRs that are primarily derived from a lentivirus.

The retroviral vectors for use herein can be derived from any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SIV), feline immunodeficiency virus (FIV), equine immunodeficiency virus (EIV), and other classes of retroviruses.

A lentiviral vector for use herein refers to a vector derived from a lentivirus, a group (or genus) of retroviruses that give rise to slowly developing disease. Viruses included within this group include HIV (human immunodeficiency virus; including HIV type 1, and HIV type 2); visna-maedi; a caprine arthritis-encephalitis virus; equine infectious anemia virus; feline immunodeficiency virus (FIV); bovine immune deficiency virus (BIV); and simian immunodeficiency virus (SIV). Preparation of the recombinant lentivirus can be achieved using the methods according to Dull et al. and Zufferey et al. (Dull et al., *J. Virol.*, 1998; 72: 8463-8471 and Zufferey et al., *J. Virol.* 1998; 72:9873-9880).

Retroviral vectors (i.e., both lentiviral and non-lentiviral) for use in the present invention can be formed using standard cloning techniques by combining the desired DNA sequences in the order and orientation described herein (Current Protocols in Molecular Biology, Ausubel, F. M. et al. (eds.) Greene Publishing Associates, (1989), Sections 9.10-9.14 and other standard laboratory manuals; Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Suitable sources for obtaining retroviral (i.e., both lentiviral and non-lentiviral) sequences for use in forming the vectors include, for example, genomic RNA and cDNAs available from commercially available sources, including the Type Culture Collection (ATCC), Rockville, Md. The sequences also can be synthesized chemically.

For expression of a HLA-A2:HPV16E7 CAR, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art, as described above. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vectors provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

The CARs of the present invention are introduced into a host cell using transfection and/or transduction techniques known in the art. As used herein, the terms, "transfection," and, "transduction," refer to the processes by which an exogenous nucleic acid sequence is introduced into a host cell. The nucleic acid may be integrated into the host cell DNA or may be maintained extrachromosomally. The nucleic acid may be maintained transiently or a may be a stable introduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into virions prior to contact with a cell. For example, a nucleic acid encoding an anti-HLA-A2:HPV16E7 CAR carried by a retroviral vector can be transduced into a cell through infection and pro virus integration.

As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

In particular, the CAR of the present invention is introduced and expressed in immune effector cells so as to redirect their specificity to a target antigen of interest, e.g., a conformational epitope of an HLA-A2 displayed HPV16E7 peptide, e.g., amino acid residues 11-19 or 82-90.

The present invention provides methods for making the immune effector cells which express the CAR as described herein. In one embodiment, the method comprises transfecting or transducing immune effector cells isolated from a subject, such as a subject having an HPV16E7-associate disease or disorder, such that the immune effector cells express one or more CAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAR. In this regard, the immune effector cells may be cultured before or after being genetically modified (i.e., transduced or transfected to express a CAR as described herein).

Prior to in vitro manipulation or genetic modification of the immune effector cells described herein, the source of cells may be obtained from a subject. In particular, the immune effector cells for use with the CARs as described herein comprise T cells. Such recombinant T cells are referred to herein as "T-bodies."

In one embodiment of the present invention, a T-body includes a CAR of the invention comprising an extracellular target-specific binding domain, a transmembrane domain, an intracellular signaling domain (such as a signaling domain derived from CD3zeta or FcRgamma), and/or one or more co-stimulatory signaling domains derived from a co-stimulatory molecule, such as, but not limited to, CD28, CD137, CD134 or CD278. In another embodiment of the present invention, a T-body includes a CAR of the invention comprising an extracellular target-specific binding domain, a transmembrane domain, a hinge or spacer region between the extracellular binding domain and the transmembrane domain, an intracellular signaling domain (such as a signaling domain derived from CD3zeta or FcRgamma), and/or one or more co-stimulatory signaling domains derived from a co-stimulatory molecule. In yet another embodiment of the present invention, a T-body includes a T-body construct CAR comprising an extracellular target-specific binding domain, and a T cell receptor constant domain. The extracellular target-specific binding domain suitable for use in a T-body comprising any of the CARs described herein may comprise a Fab, a Fab', a (Fab')2, an Fv, or a single chain Fv (scFv) of an antigen-binding protein of the invention.

T cells can be obtained from a number of sources, including peripheral blood mononuclear cells, bone marrow, lymph nodes tissue, cord blood, thymus issue, tissue from a site of infection, ascites, pleural effusion, spleen tissue, and tumors. In certain embodiments, T cell can be obtained from a unit of blood collected from the subject using any number of techniques known to the skilled person, such as FICOLL separation. In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In one embodiment of the invention, the cells are washed with PBS. In an alternative embodiment, the washed solution lacks calcium and may lack magnesium or may lack many if not all divalent cations. As would be appreciated by those of ordinary skill in the art, a washing step may be accomplished by methods known to those in the art, such as by using a semiautomated flowthrough centrifuge. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention.

PBMC may be used directly for genetic modification with the CARs using methods as described herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells. In embodiments, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, naive CD8+ T lymphocytes are characterized by the expression of phenotypic markers of naive T cells including CD62L, CCR7, CD28, CD3, CD 127, and CD45RA.

In certain embodiments, CD4+ T cells are further sorted into subpopulations. For example, CD4+ T helper cells can be sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+CD4+ T cell. In some embodiments, central memory CD4+ cells are CD62L positive and CD45RO positive. In some embodiments, effector CD4+ cells are CD62L and CD45RO negative.

The immune effector cells, such as T cells, can be genetically modified following isolation using known methods, or the immune effector cells can be activated and expanded (or differentiated in the case of progenitors) in vitro prior to being genetically modified. In another embodiment, the immune effector cells, such as T cells, are genetically modified with the chimeric antigen receptors described herein (e.g., transduced with a viral vector comprising a nucleic acid encoding a CAR) and then are activated and expanded in vitro. Methods for activating and expanding T cells are known in the art and are described, for example, in U.S. Pat. Nos. 6,905,874; 6,867,041; 6,797,514; WO2012079000, US 2016/0175358. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). In other embodiments, the T cells may be activated and stimulated to proliferate with feeder cells and appropriate antibodies and cytokines using methods such as those described in U.S. Pat. Nos. 6,040,177; 5,827,642; and WO2012129514.

The invention provides a population of modified immune effector cells for the treatment of an HPV-associated disease or disorder, e.g., cancer, the modified immune effector cells comprising an HLA-A2:HPV16E7 CAR as disclosed herein.

CAR-expressing immune effector cells prepared as described herein can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, at least 1 CD8+ central memory T cell and at least 1 CD4+ helper T cell subset) or is more typically greater than $10^2$ cells, and up to 106 up to and including $10^8$ or $10^9$ cells and can be more than $10^{10}$ cells. The number of cells will depend upon the ultimate use for which the composition is intended as will the type of cells included therein.

The cells may be autologous or heterologous to the patient undergoing therapy. If desired, the treatment may also include administration of mitogens (e.g., PHA) or lymphokines, cytokines, and/or chemokines (e.g., IFN-γ, IL-2, IL-12, TNF-α, IL-18, and TNF-β, GM-CSF, IL-4, IL-13, Flt3-L, RANTES, MIP1α, etc.) as described herein to enhance induction of the immune response.

The CAR expressing immune effector cell populations of the present invention may be administered either alone, or as a pharmaceutical composition in combination with diluents and/or with other components such as IL-2 or other cytokines or cell populations. Briefly, pharmaceutical compositions of the present invention may comprise a CAR-expressing immune effector cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

The anti-tumor immune response induced in a subject by administering CAR expressing T cells described herein using the methods described herein, or other methods known in the art, may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

Thus, the present invention provides for methods of treating an individual diagnosed with or suspected of having, or at risk of developing, an HPV-associated disease or disorder, e.g., HPV16E7-positive cancer, comprising administering the individual a therapeutically effective amount of the CAR-expressing immune effector cells as described herein.

In one embodiment, the invention provides a method of treating a subject diagnosed with an HPV16E7-positive cancer comprising removing immune effector cells from a subject diagnosed with an HPV16E7-positive cancer, genetically modifying said immune effector cells with a vector comprising a nucleic acid encoding a chimeric antigen receptor of the instant invention, thereby producing a population of modified immune effector cells, and administering the population of modified immune effector cells to the same subject. In one embodiment, the immune effector cells comprise T cells.

The methods for administering the cell compositions described herein includes any method which is effective to result in reintroduction of ex vivo genetically modified immune effector cells that either directly express a CAR of the invention in the subject or on reintroduction of the genetically modified progenitors of immune effector cells that on introduction into a subject differentiate into mature immune effector cells that express the CAR. One method comprises transducing peripheral blood T cells ex vivo with a nucleic acid construct in accordance with the invention and returning the transduced cells into the subject.

Therapeutic Administration and Formulations

The invention provides therapeutic compositions comprising the anti-HLA-A2:HPV16E7 antigen-binding proteins, e.g., antibodies, or antigen-biding fragments thereof, or CARs, of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of the antigen-binding protein, e.g., antibody, or antigen-biding fragments thereof, may vary depending upon the age and the size of a subject to be administered, target disease, conditions, route of administration, and the like. When an antigen-binding protein of the present invention is used for treating a disease or disorder in an adult patient, or for preventing such a disease, it is advantageous to administer the antigen-binding protein, e.g., antibody, or antigen-biding fragments thereof, of the present invention normally at a single dose of about 0.1 to about 60 mg/kg body weight, more preferably about 5 to about 60, about 20 to about 50, about 10 to about 50, about 1 to about 10, or about 0.8 to about 11 mg/kg body weight. Depending on the severity of the condition, the frequency and the duration of the treatment can be adjusted. In certain embodiments, the antigen-binding protein, e.g., antibody, or antigen-biding fragments thereof, of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antigen-binding protein, e.g., antibody, or antigen-biding fragments thereof, in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing mutant viruses, receptor mediated endocytosis (see, e.g., Wu et al. (1987) *J. Biol. Chem.* 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) *Science* 249: 1527-1533).

The use of nanoparticles to deliver the antigen-binding proteins, e.g., antibody, or antigen-biding fragments thereof, of the present invention is also contemplated herein. Antigen binding protein-conjugated nanoparticles may be used both for therapeutic and diagnostic applications. Antigen binding protein-conjugated nanoparticles and methods of preparation and use are described in detail by Arruebo, M., et al. 2009 ("Antibody-conjugated nanoparticles for biomedical applications" in *J. Nanomat.* Volume 2009, Article ID 439389, 24 pages, doi: 10.1155/2009/439389), incorporated herein by reference. Nanoparticles may be developed and conjugated to antigen-binding proteins contained in pharmaceutical compositions to target tumor cells or autoimmune tissue cells or virally infected cells. Nanoparticles for drug delivery have also been described in, for example, U.S. Pat. No. 8,257,740, or U.S. Pat. No. 8,246,995, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous, intracranial, intraperitoneal and intramuscular injections, drip infusions, etc. These injectable preparations may be prepared by methods publicly known. For example, the injectable preparations may be prepared, e.g., by dissolving, suspending or emulsifying the antigen-binding protein or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the antigen-binding protein contained is generally about 5 to about 500 mg per dosage form in a unit dose; especially in the form of injection, it is preferred that the antigen-binding protein is contained in about 5 to about 100 mg and in about 10 to about 250 mg for the other dosage forms.

Therapeutic Uses of the Antigen-Binding Proteins

The antibodies of the invention are useful, inter alia, for the treatment, prevention and/or amelioration of any disease or disorder associated with or mediated by HPV16. For example, the present invention provides methods for treating a HPV-associated disease or disorder, such as an HPV-associated cancer (e.g., a HPV16E7-positive cancer) (tumor growth inhibition) and/or HPV infections by administering an anti-HLA-A2:HPV16E7 antigen-binding protein (or pharmaceutical composition comprising an anti-HLA-A2:HPV16E7 antigen-binding protein) as described herein to a patient in need of such treatment, and anti-HLA-A2:HPV16E7 antigen-binding proteins (or pharmaceutical composition comprising an anti-HLA-A2:HPV16E7 antigen-binding protein) for use in the treatment of a HPV-associated cancer (tumor growth inhibition) and/or HPV infections. The antigen-binding proteins of the present invention are useful for the treatment, prevention, and/or amelioration of disease or disorder or condition such as an HPV-associated cancer or a HPV infection and/or for ameliorating at least one symptom associated with such disease, disorder or condition. In the context of the methods of treatment described herein, the anti-HLA-A2:HPV16E7 antigen-binding protein may be administered as a monotherapy (i.e., as the only therapeutic agent) or in combination with one or more additional therapeutic agents (examples of which are described elsewhere herein).

In some embodiments of the invention, the antibodies described herein are useful for treating subjects suffering from primary or recurrent cancer, including, but not limited to, HPV-associated cancer, e.g., squamous cell carcinomas, such as squamous cell carcinoma of head and neck, cervical cancer, anogenital cancer, oropharyngeal cancer.

The antigen-binding proteins may be used to treat early stage or late-stage symptoms of the HPV-associated cancer. In one embodiment, an antibody or fragment thereof of the invention may be used to treat advanced or metastatic cancer. The antigen-binding proteins are useful in reducing or inhibiting or shrinking tumor growth. In certain embodiments, treatment with an antigen-binding protein of the invention leads to more than 40% regression, more than 50% regression, more than 60% regression, more than 70% regression, more than 80% regression or more than 90% regression of a tumor in a subject. In certain embodiments, the antigen-binding proteins may be used to prevent relapse of a tumor. In certain embodiments, the antigen-binding proteins are useful in extending progression-free survival or overall survival in a subject with HPV-associated cancer. In some embodiments, the antibodies are useful in reducing toxicity due to chemotherapy or radiotherapy while maintaining long-term survival in a patient suffering from HPV-associated cancer.

In certain embodiments, the antigen-binding proteins of the invention are useful to treat subjects suffering from a chronic HPV infection. In some embodiments, the antigen-binding proteins of the invention are useful in decreasing viral titers in the host.

One or more antibodies of the present invention may be administered to relieve or prevent or decrease the severity of one or more of the symptoms or conditions of the disease or disorder.

It is also contemplated herein to use one or more antibodies of the present invention prophylactically to patients at risk for developing a disease or disorder such as HPV-associated disease or disorder, such as an HPV-associated cancer, and HPV infection.

In a further embodiment of the invention, the present antibodies are used for the preparation of a pharmaceutical composition for treating patients suffering from HPV-associated disease or disorder, such as an HPV-associated cancer, or HPV infection. In another embodiment of the invention, the present antibodies are used as adjunct therapy with any other agent or any other therapy known to those skilled in the art useful for treating HPV-associated cancer or HPV infection.

Combination Therapies and Formulations

Combination therapies may include an anti-HLA-A2:HPV16E7 antigen-binding protein of the invention, such as a CAR of the invention (e.g., an immune effector cell comprising a CAR of the invention) or a pharmaceutical composition of the invention, and any additional therapeutic agent that may be advantageously combined with an antigen-binding protein of the invention. The antigen-binding proteins of the present invention may be combined synergistically with one or more anti-cancer drugs or therapy used to treat or inhibit an HPV16E7-associated disease or disorder, such as HPV-positive cancer, e.g., squamous cell carcinoma, cervical cancer, anogenital cancer, head and neck cancer, or oropharyngeal cancer.

It is contemplated herein to use the anti-HLA-A2:HPV16E7 antigen-binding proteins of the invention in combination with immunostimulatory and/or immunosupportive therapies to inhibit tumor growth, and/or enhance survival of cancer patients. The immunostimulatory therapies include direct immunostimulatory therapies to augment immune cell activity by either "releasing the brake" on suppressed immune cells or "stepping on the gas" to activate an immune response. Examples include targeting other checkpoint receptors, vaccination and adjuvants. The immunosupportive modalities may increase antigenicity of the tumor by promoting immunogenic cell death, inflammation or have other indirect effects that promote an anti-tumor immune response. Examples include radiation, chemotherapy, anti-angiogenic agents, and surgery.

In various embodiments, one or more antigen-binding proteins of the present invention may be used in combination with a PD-1 inhibitor (e.g., an anti-PD-1 antibody such as nivolumab, pembrolizumab, pidilizumab, BGB-A317 or REGN2810), a PD-L1 inhibitor (e.g., an anti-PD-L1 antibody such as avelumab, atezolizumab, durvalumab, MDX-1105, or REGN3504), a CTLA-4 inhibitor (e.g., ipilimumab), a TIM3 inhibitor, a BTLA inhibitor, a TIGIT inhibitor, a CD47 inhibitor, a GITR inhibitor, an antagonist of another T cell co-inhibitor or ligand (e.g., an antibody to CD-28, 2B4, LY108, LAIR1, ICOS, CD160 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor beta (TGFβ) inhibitor, an epidermal growth factor receptor (EGFR) inhibitor (e.g., erlotinib, cetuximab), a CD20 inhibitor (e.g., an anti-CD20 antibody such as rituximab), an antibody to a tumor-specific antigen [e.g., CA9, CA125, melanoma-associated antigen 3 (MAGE3), carcinoembryonic antigen (CEA), vimentin, tumor-M2-PK, prostate-specific antigen (PSA), mucin-1, MART-1, and CA19-9], a vaccine (e.g., *Bacillus* Calmette-Guerin, a cancer vaccine), an adjuvant to increase antigen presentation (e.g., granulocyte-macrophage colony-stimulating factor), a bispecific antibody (e.g., CD3×CD20 bispecific antibody, or PSMA×CD3 bispecific antibody), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, surgery, an IL-6R inhibitor (e.g., sarilumab), an IL-4R inhibitor (e.g., dupilumab), an IL-10 inhibitor, a cytokine such as IL-2, IL-7, IL-21, and IL-15, an antibody-drug conjugate (ADC) (e.g., anti-CD19-DM4 ADC, and anti-DS6-DM4 ADC), an anti-inflammatory drug (e.g., corticosteroids, and non-steroidal anti-inflammatory drugs), a dietary supplement such as antioxidants or any other therapy care to treat cancer. In certain embodiments, the anti-HLA-A2:HPV16E7 antigen-binding protein of the present invention may be used in combination with an HPV vaccine. Exemplary HPV vaccines include Gardasil, Gardasil 9, and Cervarix, Lm-LLo-E7 (ADXS11-001; ADXS-HPV; Advaxis, Inc.); GLBL101c (GENOLAC BL Corp); TA-HPV (European Organization for Research and Treatment of Cancer (EORTC)); TG4001 (Transgene/Roche); MVA E2 (Instituto Mexicano del Seguro Social); HPV16-SLP (ISA Pharmaceuticals); GL-0810 (Gliknik Inc.); Pepcan+Candin (University of Arkansas); GTL001 (ProCervix; Genticel); TA-CIN (Xenova Research Limited); TA-CIN+TA-HPV (Celtic Pharma); pNGVL4a-sig/E7(detox)/HSP70+ TA-HPV (Sidney Kimmel Comprehensive Cancer Center); pNGVL4a-CRT/E7(detox) (Sidney Kimmel Comprehensive Cancer Center); GX-188E (Genexine, Inc); VGX-3100 (Inovio Pharmaceuticals); Dendritic Cells pulsed with HPV-16 and HPV-18 E7 and keyhole limpet hemocyanin (National Institutes of Health); DC pulsed with HPV+ tumor lysate (Department of Biotechnology (DBT, Govt. of India)); PDS0101 (PDS Biotechnology Corp); ProCervix (Genticel); GX-188E (Genexine, Inc); pNGVL4a-CRT/E7(detox) (Sidney Kimmel Comprehensive Cancer Center); pNGVL4a-sig/E7(detox)/HSP70+ TA-HPV (Sidney Kimmel Comprehensive Cancer Center); TVGV-1+ GPI-0100 (THEVAX Genetics Vaccine Co.); Pepcan+Candin (University of Arkansas); ISA101 (SLP-HPV-01; HPV16-SLP; ISA Pharmaceuticals); ADXS11-001 (Lm-LLo-E7; Advaxis, Inc.); ISA101 (SLP-HPV-01; HPV16-SLP; ISA Pharmaceuticals); DPX-E7 (Dana-Farber Cancer Institute); ADXS11-001 (Lm-LLo-E7; Advaxis, Inc.); INO-3112 (VGX-3100+INO-9012; Inovio Pharmaceuticals);

ADXS11-001 (Lm-LLo-E7; Advaxis, Inc.); INO-3112 (VGX-3100+INO-9012; Inovio Pharmaceuticals); ISA101 (SLP-HPV-01; HPV16-SLP; ISA Pharmaceuticals); and TA-CIN+GPI-0100 (Sidney Kimmel Comprehensive Cancer Center). In certain embodiments, the anti-HLA-A2: HPV16E7 antigen-binding protein of the present invention may be used in combination with cancer vaccines including dendritic cell vaccines, oncolytic viruses, tumor cell vaccines, etc. to augment the anti-tumor response. Examples of cancer vaccines that can be used in combination with anti-HLA-A2:HPV16E7 antigen-binding proteins of the present invention include MAGE3 vaccine for melanoma and bladder cancer, MUC1 vaccine for breast cancer, EGFRv3 (e.g., Rindopepimut) for brain cancer (including glioblastoma multiforme), or ALVAC-CEA (for CEA+ cancers).

In certain embodiments, the anti-HLA-A2:HPV16E7 antigen-binding proteins of the invention may be administered in combination with radiation therapy in methods to generate long-term durable anti-tumor responses and/or enhance survival of patients with cancer. In some embodiments, the anti-HLA-A2:HPV16E7 antigen-binding proteins of the invention may be administered prior to, concomitantly or after administering radiation therapy to a cancer patient. For example, radiation therapy may be administered in one or more doses to tumor lesions followed by administration of one or more doses of anti-HLA-A2: HPV16E7 antigen-binding proteins of the invention. In some embodiments, radiation therapy may be administered locally to a tumor lesion to enhance the local immunogenicity of a patient's tumor (adjuvinating radiation) and/or to kill tumor cells (ablative radiation) followed by systemic administration of an anti-HLA-A2:HPV16E7 antigen-binding protein of the invention. For example, intracranial radiation may be administered to a patient with brain cancer (e.g., glioblastoma multiforme) in combination with systemic administration of an anti-HLA-A2:HPV16E7 antigen-binding protein of the invention. In certain embodiments, the anti-HLA-A2:HPV16E7 antigen-binding proteins of the invention may be administered in combination with radiation therapy and a chemotherapeutic agent (e.g., temozolomide) or a VEGF antagonist (e.g., aflibercept).

In certain embodiments, the anti-HLA-A2:HPV16E7 antigen-binding proteins of the invention may be administered in combination with one or more anti-viral drugs to treat chronic HPV infection. Examples of anti-viral drugs include, but are not limited to, zidovudine, lamivudine, abacavir, ribavirin, lopinavir, efavirenz, cobicistat, tenofovir, rilpivirine and corticosteroids.

The additional therapeutically active agent(s)/component(s) may be administered prior to, concurrent with, or after the administration of the anti-HLA-A2:HPV16E7 antigen-binding proteins of the present invention. For purposes of the present disclosure, such administration regimens are considered the administration of an anti-HLA-A2: HPV16E7 antigen-binding protein "in combination with" a second therapeutically active component.

The additional therapeutically active component(s) may be administered to a subject prior to administration of an anti-HLA-A2:HPV16E7 antigen-binding protein of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-HLA-A2:HPV16E7 antigen-binding protein of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an anti-HLA-A2:HPV16E7 antigen-binding protein of the present invention. "Concurrent" administration, for purposes of the present invention, includes, e.g., administration of an anti-HLA-A2:HPV16E7 antigen-binding protein and an additional therapeutically active component to a subject in a single dosage form (e.g., co-formulated), or in separate dosage forms administered to the subject within about 30 minutes or less of each other. If administered in separate dosage forms, each dosage form may be administered via the same route (e.g., both the anti-HLA-A2: HPV16E7 antigen-binding protein and the additional therapeutically active component may be administered intravenously, subcutaneously, etc.); alternatively, each dosage form may be administered via a different route (e.g., the anti-HLA-A2:HPV16E7 antigen-binding protein may be administered intravenously, and the additional therapeutically active component may be administered subcutaneously). In any event, administering the components in a single dosage from, in separate dosage forms by the same route, or in separate dosage forms by different routes are all considered "concurrent administration," for purposes of the present disclosure. For purposes of the present disclosure, administration of an anti-HLA-A2:HPV16E7 antigen-binding protein "prior to", "concurrent with," or "after" (as those terms are defined herein above) administration of an additional therapeutically active component is considered administration of an anti-HLA-A2:HPV16E7 antigen-binding protein "in combination with" an additional therapeutically active component).

The present invention includes pharmaceutical compositions in which an anti-HLA-A2:HPV16E7 antigen-binding protein of the present invention is co-formulated with one or more of the additional therapeutically active component(s) as described elsewhere herein using a variety of dosage combinations.

Administrative Regimens

According to certain embodiments of the present invention, multiple doses of an anti-HLA-A2:HPV16E7 antigen-binding protein (or a pharmaceutical composition comprising a combination of an anti-HLA-A2:HPV16E7 antigen-binding protein and any of the additional therapeutically active agents mentioned herein) may be administered to a subject over a defined time course. The methods according to this aspect of the invention comprise sequentially administering to a subject multiple doses of an anti-HLA-A2: HPV16E7 antigen-binding protein of the invention. As used herein, "sequentially administering" means that each dose of anti-HLA-A2:HPV16E7 antigen-binding protein is administered to the subject at a different point in time, e.g., on different days separated by a predetermined interval (e.g., hours, days, weeks or months). The present invention includes methods which comprise sequentially administering to the patient a single initial dose of an anti-HLA-A2:HPV16E7 antigen-binding protein, followed by one or more secondary doses of the anti-HLA-A2:HPV16E7 antigen-binding protein, and optionally followed by one or more tertiary doses of the anti-HLA-A2:HPV16E7 antigen-binding protein. The anti-HLA-A2:HPV16E7 antigen-binding protein may be administered at a dose between 0.1 mg/kg to 100 mg/kg body weight of the subject.

The terms "initial dose," "secondary doses," and "tertiary doses," refer to the temporal sequence of administration of the anti-HLA-A2:HPV16E7 antigen-binding protein of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-HLA-A2:HPV16E7 antigen-binding protein, but generally may differ from one another in terms of frequency of administration. In certain embodiments, however, the amount of anti-HLA-A2:HPV16E7 antigen-binding protein contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain embodiments, the amount of anti-HLA-A2:HPV16E7 antigen-binding protein contained in the initial, secondary and/or tertiary doses may be sub-optimal or sub-therapeutic. As used herein, the terms "sub-therapeutic" or "sub-optimal" refer to an antibody dose administered at too low a level to produce a therapeutic effect or below the level necessary to treat a disease such as cancer.

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-HLA-A2:HPV16E7 antigen-binding protein which is administered to a patient prior to the administration of the very next dose in the sequence with no intervening doses.

The methods according to this aspect of the invention may comprise administering to a patient any number of secondary and/or tertiary doses of an anti-HLA-A2:HPV16E7 antigen-binding protein. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antigen Binding Proteins

The anti-HLA-A2:HPV16E7 antigen-binding proteins of the present invention may be used to detect and/or measure HPV16E7 in a sample, e.g., for diagnostic purposes. Some embodiments contemplate the use of one or more antigen-binding proteins of the present invention in assays to detect a disease or disorder such as HPV-associated disease or disorder, such as an HPV16E7-positive cancer, or HPV infection. Exemplary diagnostic assays for HPV16E7 may comprise, e.g., contacting a sample, obtained from a subject (e.g., a patient), with an anti-HLA-A2:HPV16E7 antigen-binding protein of the invention, wherein the anti-HLA-A2:HPV16E7 antigen-binding protein is labeled with a detectable label or reporter molecule or used as a capture ligand to selectively isolate HPV16E7 from subject samples. Alternatively, an unlabeled anti-HLA-A2:HPV16E7 antigen-binding protein can be used in diagnostic applications in combination with a secondary antigen-binding protein, e.g., antibody, which is itself detectably labeled. The detectable label or reporter molecule can be a radioisotope, such as $^3$H, $^{14}$O, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure HPV16E7 in a sample include enzyme-linked immunosorbent assay (ELISA), radioimmunoassay (RIA), and fluorescence-activated cell sorting (FACS).

Samples that can be used in HPV16E7 diagnostic assays according to the present invention include any tissue or fluid sample obtainable from a subject, which contains detectable quantities of either HPV16E7 protein, or fragments thereof, under normal or pathological conditions. Generally, levels of HPV16E7 in a particular sample obtained from a healthy patient (e.g., a patient not afflicted with a HPV16E7-associated disease or disorder, e.g., HPV16E7-positive cancer) will be measured to initially establish a baseline, or standard, level of HPV16E7. This baseline level of HPV16E7 can then be compared against the levels of HPV16E7 measured in samples obtained from individuals suspected of having a cancer-related condition, or symptoms associated with such condition.

The antigen-binding proteins specific for HPV16E7 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Aspects of the invention relate to use of the disclosed antigen-binding proteins as markers for predicting prognosis of HPV16E7-positive cancer or HPV infection in patients. Antigen binding proteins of the present invention may be used in diagnostic assays to evaluate prognosis of cancer in a patient and to predict survival.

This invention is further illustrated by the following examples which should not be construed as limiting. The entire contents of all references, patents and published patent applications cited throughout this application, as well as the Informal Sequence Listing, are hereby incorporated herein by reference.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies to HLA-A2:HPV16E7

Human antibodies to HLA-A2:HPV16E7 were generated using peptide fragments of HPV16E7 that include either amino acids 11-19 (YMLDLQPET; SEQ ID NO: 538) of GenBank Accession NP_041326.1 (SEQ ID NO: 537) or amino acid residues 82-90 (LLMGTLGIV; SEQ ID NO: 539) of GenBank Accession NP_041326.1 (SEQ ID NO: 537), coupled to HLA-A2. The immunogen was administered directly, with an adjuvant to stimulate the immune response, to a VELOCIMMUNE® mouse (i.e., an engineered mouse comprising DNA encoding human Immunoglobulin heavy and kappa light chain variable regions), e.g., as described in U.S. Pat. No. 8,502,018. The antibody immune response was monitored by an HLA-A2:HPV16E7-specific immunoassay. When a desired immune response was achieved splenocytes were harvested and fused with mouse myeloma cells to preserve their viability and form hybridoma cell lines. The hybridoma cell lines were screened and selected to identify cell lines that produce HLA-A2:HPV16E7-specific antibodies. Using this technique, and the immunogen described above, several anti-HPV16E7 chimeric antibodies (i.e., antibodies possessing human variable domains and mouse constant domains) were obtained. Exemplary antibodies generated in this manner were designated as follows: H4sH17364N; H4sH17368N2; H4sH17930N; H4sH17930N2; H4sH17363N and H4sH17368N3.

Anti-HLA-A2:HPV16E7 antibodies were also isolated directly from antigen-positive B cells (from either of the immunized mice) without fusion to myeloma cells, as described in U.S. Pat. No. 7,582,298, herein specifically incorporated by reference in its entirety. Using this method, several fully human anti-HLA-A2:HPV16E7 antibodies (i.e., antibodies possessing human variable domains and human constant domains) were obtained.

Exemplary antibodies generated according to the foregoing methods were designated as follows: H4sH17670P; H4sH17672P; H4sH17673P; H4sH17675P; H4sH17680P; H4sH17697P; H4sH17707P; H4sH17715P; H4sH17726P; H4sH17730P; H4sH21051P; H4sH21054P; H4sH21055P; H4sH21058P; H4sH21064P; H4sH21073P; H4sH21077P; H4sH21079P; H4sH21080P; H4sH21083P; H4sH21086P; H4sH21090P; H4sH21091P; H4sH21093P; H4sH21099P; H4sH21100P; H4sH21103P; and H4sH21104P.

The biological properties of the exemplary antibodies generated in accordance with the methods of this Example are described in detail in the Examples set forth below.

Example 2: Heavy and Light Chain Variable Region Amino Acid and Nucleotide Sequences Table 1 sets forth the amino acid sequence identifiers of the heavy and light chain variable regions and CDRs of selected anti-HLA-A2:HPV16E7 antibodies of the invention. The corresponding nucleic acid sequence identifiers are set forth in Table 2.

TABLE 1

| Antibody Designation | Amino Acid Sequence Identifiers SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4sH17364N | 2 | 4 | 6 | 8 | 10 | 12 | 14 | 16 |
| H4sH17368N2 | 18 | 20 | 22 | 24 | 26 | 28 | 30 | 32 |
| H4sH17670P | 34 | 36 | 38 | 40 | 42 | 44 | 46 | 48 |
| H4sH17672P | 50 | 52 | 54 | 56 | 58 | 60 | 62 | 64 |
| H4sH17673P | 66 | 68 | 70 | 72 | 74 | 76 | 78 | 80 |
| H4sH17675P | 82 | 84 | 86 | 88 | 90 | 92 | 94 | 96 |
| H4sH17680P | 98 | 100 | 102 | 104 | 106 | 108 | 110 | 112 |
| H4sH17697P | 114 | 116 | 118 | 120 | 122 | 124 | 126 | 128 |
| H4sH17707P | 130 | 132 | 134 | 136 | 138 | 140 | 142 | 144 |
| H4sH17715P | 146 | 148 | 150 | 152 | 154 | 156 | 158 | 160 |
| H4sH17726P | 162 | 164 | 166 | 168 | 170 | 172 | 174 | 176 |
| H4sH17730P | 178 | 180 | 182 | 184 | 186 | 188 | 190 | 192 |
| H4sH17930N | 210 | 212 | 214 | 216 | 202 | 204 | 206 | 208 |
| H4sH17930N2 | 194 | 196 | 198 | 200 | 202 | 204 | 206 | 208 |
| H4sH21051P | 218 | 220 | 222 | 224 | 226 | 228 | 230 | 232 |
| H4sH21054P | 234 | 236 | 238 | 240 | 242 | 244 | 246 | 248 |
| H4sH21055P | 250 | 252 | 254 | 256 | 258 | 260 | 262 | 264 |
| H4sH21058P | 266 | 268 | 270 | 272 | 274 | 276 | 278 | 280 |
| H4sH21064P | 282 | 284 | 286 | 288 | 290 | 292 | 294 | 296 |
| H4sH21073P | 298 | 300 | 302 | 304 | 306 | 308 | 310 | 312 |
| H4sH21077P | 314 | 316 | 318 | 320 | 322 | 324 | 326 | 328 |
| H4sH21079P | 330 | 332 | 334 | 336 | 338 | 340 | 342 | 344 |

TABLE 1-continued

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4sH21080P | 346 | 348 | 350 | 352 | 354 | 356 | 358 | 360 |
| H4sH21083P | 362 | 364 | 366 | 368 | 370 | 372 | 374 | 376 |
| H4sH21086P | 378 | 380 | 382 | 384 | 386 | 388 | 390 | 392 |
| H4sH21090P | 394 | 396 | 398 | 400 | 402 | 404 | 406 | 408 |
| H4sH21091P | 410 | 412 | 414 | 416 | 418 | 420 | 422 | 424 |
| H4sH21093P | 426 | 428 | 430 | 432 | 434 | 436 | 438 | 440 |
| H4sH21099P | 442 | 444 | 446 | 448 | 450 | 452 | 454 | 456 |
| H4sH21100P | 458 | 460 | 462 | 464 | 466 | 468 | 470 | 472 |
| H4sH21103P | 474 | 476 | 478 | 480 | 482 | 484 | 486 | 488 |
| H4sH21104P | 490 | 492 | 494 | 496 | 498 | 500 | 502 | 504 |
| H4sH17363N | 506 | 508 | 510 | 512 | 514 | 516 | 518 | 520 |
| H4sH17368N3 | 522 | 524 | 526 | 528 | 530 | 532 | 534 | 536 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4sH17364N | 1 | 3 | 5 | 7 | 9 | 11 | 13 | 15 |
| H4sH17368N2 | 17 | 19 | 21 | 23 | 25 | 27 | 29 | 31 |
| H4sH17670P | 33 | 35 | 37 | 39 | 41 | 43 | 45 | 47 |
| H4sH17672P | 49 | 51 | 53 | 55 | 57 | 59 | 61 | 63 |
| H4sH17673P | 65 | 67 | 69 | 71 | 73 | 75 | 77 | 79 |
| H4sH17675P | 81 | 83 | 85 | 87 | 89 | 91 | 93 | 95 |
| H4sH17680P | 97 | 99 | 101 | 103 | 105 | 107 | 109 | 111 |
| H4sH17697P | 113 | 115 | 117 | 119 | 121 | 123 | 125 | 127 |
| H4sH17707P | 129 | 131 | 133 | 135 | 137 | 139 | 141 | 143 |
| H4sH17715P | 145 | 147 | 149 | 151 | 153 | 155 | 157 | 159 |
| H4sH17726P | 161 | 163 | 165 | 167 | 169 | 171 | 173 | 175 |
| H4sH17730P | 177 | 179 | 181 | 183 | 185 | 187 | 189 | 191 |
| H4sH17930N | 209 | 211 | 213 | 215 | 201 | 203 | 205 | 207 |
| H4sH17930N2 | 193 | 195 | 197 | 199 | 201 | 203 | 205 | 207 |
| H4sH21051P | 217 | 219 | 221 | 223 | 225 | 227 | 229 | 231 |
| H4sH21054P | 233 | 235 | 237 | 239 | 241 | 243 | 245 | 247 |
| H4sH21055P | 249 | 251 | 253 | 255 | 257 | 259 | 261 | 263 |
| H4sH21058P | 265 | 267 | 269 | 271 | 273 | 275 | 277 | 279 |
| H4sH21064P | 281 | 283 | 285 | 287 | 289 | 291 | 293 | 295 |
| H4sH21073P | 297 | 299 | 301 | 303 | 305 | 307 | 309 | 311 |
| H4sH21077P | 313 | 315 | 317 | 319 | 321 | 323 | 325 | 327 |
| H4sH21079P | 329 | 331 | 333 | 335 | 337 | 339 | 341 | 343 |
| H4sH21080P | 345 | 347 | 349 | 351 | 353 | 355 | 357 | 359 |
| H4sH21083P | 361 | 363 | 365 | 367 | 369 | 371 | 373 | 375 |
| H4sH21086P | 377 | 379 | 381 | 383 | 385 | 387 | 389 | 391 |
| H4sH21090P | 393 | 395 | 397 | 399 | 401 | 403 | 405 | 407 |
| H4sH21091P | 409 | 411 | 413 | 415 | 417 | 419 | 421 | 423 |
| H4sH21093P | 425 | 427 | 429 | 431 | 433 | 435 | 437 | 439 |
| H4sH21099P | 441 | 443 | 445 | 447 | 449 | 451 | 453 | 455 |
| H4sH21100P | 457 | 459 | 461 | 463 | 465 | 467 | 469 | 471 |
| H4sH21103P | 473 | 475 | 477 | 479 | 481 | 483 | 485 | 487 |
| H4sH21104P | 489 | 491 | 493 | 495 | 497 | 499 | 501 | 503 |
| H4sH17363N | 505 | 507 | 509 | 511 | 513 | 515 | 517 | 519 |
| H4sH17368N3 | 521 | 523 | 525 | 527 | 529 | 531 | 533 | 535 |

Antibodies are typically referred to herein according to the following nomenclature: Fc prefix (e.g. "H1 M," "H4sH," "H4H," etc.), followed by a numerical identifier (e.g. "17670," "17930," etc., as shown in Table 1), followed by a "P," "N," or "N2" suffix. Thus, according to this nomenclature, an antibody may be referred to herein as, e.g., "H4sH17670P," "H4sH17930N," "H4sH17368N2," etc. The H4sH and H4H prefixes on the antibody designations used herein indicate the particular Fc region isotype of the antibody. For example, an "H4sH" antibody has a human IgG4 Fc with 2 or more amino acid changes as disclosed in U.S. Patent Publication No. 20140243504 (herein incorporated in its entirety), an "H4H" antibody has a human IgG4 Fc with a serine to proline mutation in the hinge region (S108P), an "H1 M" antibody has a mouse IgG1 Fc, and an "H2M" antibody has a mouse IgG2 Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

In certain embodiments, selected antibodies with a mouse IgG1 Fc were converted to antibodies with human IgG4 Fc. In certain embodiments, the antibody comprises a human IgG4 Fc with 2 or more amino acid changes as disclosed in U.S. Patent Publication No. 20100331527 (herein incorporated in its entirety). In one embodiment, the IgG4 Fc domain comprises a serine to proline mutation in the hinge region (S108P) to promote dimer stabilization.

Table 3 sets forth the amino acid sequence identifiers of heavy chain and light chain sequences of selected antibodies of the invention.

TABLE 3

Heavy chain and light chain sequence identifiers

| Antibody Designation | SEQ ID NOs: | |
|---|---|---|
| | Heavy Chain | Light Chain |
| H4sH17363N | 578 | 579 |
| H4sH17364N | 580 | 581 |
| H4sH17670P | 582 | 583 |
| H4sH17675P | 584 | 585 |
| H4sH17930N2 | 586 | 587 |
| H4sH21058P | 588 | 589 |
| H4sH21064P | 590 | 591 |
| H4sH21104P | 592 | 593 |

Example 3: Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each heavy chain variable region (HCVR) and light chain variable region (LCVR) (Table 4).

TABLE 4

| Antibody Designation | HCVR (HPV) | | | LCVR (HPV) | |
|---|---|---|---|---|---|
| | $V_H$ | $D_H$ | $J_H$ | $V_H$ | $J_H$ |
| H4sH17363N | V3-23 | D6-6 | J6 | V1-39 | J5 |
| H4sH17364N | V3-23 | D6-6 | J6 | V1-39 | J5 |
| H4sH17368N2 | V3-23 | D3-9 | J4 | V1-39 | J5 |
| H4sH17368N3 | V3-23 | D3-9 | J4 | V1-39 | J5 |
| H4sH17670P | V3-64 | D1-26 | J6 | V1-39 | J5 |
| H4sH17672P | V3-64 | D1-26 | J6 | V1-39 | J5 |
| H4sH17673P | V3-23 | D4-11 | J6 | V1-39 | J5 |
| H4sH17675P | V3-64 | D1-26 | J6 | V1-39 | J5 |
| H4sH17680P | V3-23 | D4-23 | J6 | V1-39 | J5 |
| H4sH17697P | V3-11 | D6-13 | J4 | V1-39 | J2 |
| H4sH17707P | V3-23 | D1-20 | J4 | V1-39 | J5 |
| H4sH17715P | V6-1 | D1-7 | J3 | V1-39 | J2 |
| H4sH17726P | V1-18 | D1-7 | J4 | V3-15 | J4 |
| H4sH17730P | V3-11 | D1-7 | J4 | V1-17 | J2 |
| H4sH17930N | V3-64 | D2-2 | J6 | V1-39 | J5 |
| H4sH17930N2 | V3-64 | D2-2 | J6 | V1-39 | J5 |
| H4sH21051P | V3-23 | D7-27 | J4 | V1-39 | J5 |
| H4sH21054P | V3-23 | D1-7 | J4 | V1-39 | J5 |
| H4sH21055P | V3-11 | D7-27 | J2 | V1-39 | J2 |
| H4sH21058P | V3-20 | D2-2 | J5 | V1-39 | J2 |
| H4sH21064P | V3-64 | D6-6 | J6 | V1-39 | J5 |
| H4sH21073P | V3-43 | D6-19 | J3 | V1-39 | J2 |
| H4sH21077P | V3-23 | D6-19 | J3 | V1-39 | J2 |
| H4sH21079P | V3-15 | D1-7 | J4 | V1-39 | J2 |
| H4sH21080P | V3-23 | D1-7 | J6 | V2-28 | J1 |
| H4sH21083P | V3-23 | D1-7 | J2 | V3-15 | J5 |
| H4sH21086P | V3-33 | D2-21 | J6 | V4-1 | J5 |

TABLE 4-continued

| Antibody Designation | HCVR (HPV) | | | LCVR (HPV) | |
|---|---|---|---|---|---|
| | $V_H$ | $D_H$ | $J_H$ | $V_H$ | $J_H$ |
| H4sH21090P | V3-23 | D1-20 | J4 | V3-15 | J4 |
| H4sH21091P | V3-15 | D6-19 | J6 | V1-17 | J4 |
| H4sH21093P | V3-33 | D3-3 | J3 | V1-6 | J2 |
| H4sH21099P | V3-9 | D1-1 | J6 | V1-39 | J5 |
| H4sH21100P | V3-9 | D1-7 | J3 | V1-39 | J5 |
| H4sH21103P | V3-15 | D1-7 | J4 | V1-39 | J5 |
| H4sH21104P | V3-11 | D3-10 | J3 | V1-39 | J5 |

Example 4: Surface Plasmon Resonance Derived Binding Affinities and Kinetic Constants of Human Monoclonal Anti-HLA-A2:HPV16E7 Monospecific Antibodies Binding affinities and kinetic constants of human anti-HLA-A2/HPV16E7 antibodies were determined via real-time surface plasmon resonance (SPR; Biacore 4000 or Biacore T-200, GE Healthcare Life Sciences, Pittsburgh, PA) at 25° C. Antibodies were captured onto a CM5 Biacore sensor surface (GE Healthcare Life Sciences) derivatized via amine coupling with a monoclonal anti-human Fc antibody (GE, #BR-1008-39). Various concentrations of monomeric HLA-A2: HPV16E7 peptide complex containing either the E7:11-19 peptide (SEQ ID NO: 538) or the E7:82-90 peptide (SEQ ID NO: 539) were injected over the anti-HLA-A2: HPV16E7 antibody captured surface at a flow rate of 504/minute (Biacore T-200) or 304/minute (Biacore 4000). Antibody-reagent association was monitored for 4-5 min. and the dissociation was monitored for 10 min. All binding studies were performed in HBS-ET buffer (0.01M HEPES pH 7.4, 0.15M NaCl, 0.05% v/v Surfactant P20).

Kinetic association ($k_a$) and dissociation ($k_d$) rate constants were determined by fitting the real-time sensorgrams to a 1:1 binding model using Scrubber 2.0c curve fitting software. Binding dissociation equilibrium constants ($K_D$) and dissociative half-lives (t½) were calculated from the kinetic rate constants as:

$$K_D(M) = \frac{kd}{ka}, \text{ and } t1/2(\min) = \frac{\ln(2)}{60*kd}.$$

Binding kinetic parameters for the monospecific anti-HLA-A2:HPV16E7 antibodies to monomeric HLA-A2/HPV16E7 peptide complex are shown below in Tables 5 and 6.

TABLE 5

Biacore binding affinities of anti-HLA-A2/HPV16E7 (11-19) antibodies at 25° C.

| | HLA-A2:HPV16E7(11-19) | | | |
|---|---|---|---|---|
| Antibody | ka (1/Ms) | kd (1/s) | KD (M) | t½ (min) |
| H4sH17670P | 8.16E+04 | 1.43E−03 | 1.75E−08 | 8.1 |
| H4sH17672P | 1.29E+05 | 8.19E−04 | 6.37E−09 | 14.1 |
| H4sH17673P | NB | NB | NB | NB |
| H4sH17675P | 5.99E+04 | 1.38E−03 | 2.31E−08 | 8.4 |
| H4sH17680P | NB | NB | NB | NB |
| H4sH17697P | NB | NB | NB | NB |
| H4sH17707P | NB | NB | NB | NB |
| H4sH17715P | NB | NB | NB | NB |
| H4sH17726P | NB | NB | NB | NB |

TABLE 5-continued

Biacore binding affinities of anti-HLA-
A2/HPV16E7 (11-19) antibodies at 25° C.

| Antibody | HLA-A2:HPV16E7(11-19) | | | |
|---|---|---|---|---|
|  | ka (1/Ms) | kd (1/s) | KD (M) | t½ (min) |
| H4sH17730P | NB | NB | NB | NB |
| H4sH17363N | 8.72E+04 | 1.54E-03 | 1.76E-08 | 7.5 |
| H4sH17364N | 8.56E+04 | 1.57E-03 | 1.83E-08 | 7.4 |
| H4sH17368N2 | NB | NB | NB | NB |
| H4sH17368N3 | NB | NB | NB | NB |
| H4sH17930N | 7.84E+04 | 7.96E-04 | 1.02E-08 | 14.5 |
| H4sH17930N2 | 8.28E+04 | 7.92E-04 | 9.57E-09 | 14.6 |
| H4sH21051P | NB | NB | NB | NB |
| H4sH21054P | NB | NB | NB | NB |
| H4sH21055P | NB | NB | NB | NB |
| H4sH21058P | NB | NB | NB | NB |
| H4sH21064P | 5.47E+04 | 7.91E-04 | 1.44E-08 | 14.6 |
| H4sH21073P | NB | NB | NB | NB |
| H4sH21077P | NB | NB | NB | NB |
| H4sH21079P | 3.74E+04 | 1.09E-02 | 2.90E-07 | 1.1 |
| H4sH21080P | 1.79E+05 | 3.90E-02 | 2.18E-07 | 0.3 |
| H4sH21083P | NB | NB | NB | NB |
| H4sH21086P | NB | NB | NB | NB |
| H4sH21090P | NB | NB | NB | NB |
| H4sH21091P | NB | NB | NB | NB |
| H4sH21093P | NB | NB | NB | NB |
| H4sH21099P | NB | NB | NB | NB |
| H4sH21100P | NB | NB | NB | NB |
| H4sH21103P | NB | NB | NB | NB |
| H4sH21104P | NB | NB | NB | NB |

*NB indicates that under experimental conditions, HLA-A2:HPV16E7(11-19) peptide reagent did not bind to the captured anti-HLA-A2:HPV16E7 monoclonal antibody

TABLE 6

Biacore binding affinities of anti-HLA-
A2/HPV16E7 (82-90) antibodies at 25° C.

| Antibody | HLA-A2:HPV16E7(82-90) | | | |
|---|---|---|---|---|
|  | ka (1/Ms) | kd (1/s) | KD (M) | t½ (min) |
| H4sH17670P | NB | NB | NB | NB |
| H4sH17672P | NB | NB | NB | NB |
| H4sH17673P | NB | NB | NB | NB |
| H4sH17675P | NB | NB | NB | NB |
| H4sH17680P | NB | NB | NB | NB |
| H4sH17697P | NB | NB | NB | NB |
| H4sH17707P | 7.15E+04 | 3.61E-04 | 5.05E-09 | 32.0 |
| H4sH17715P | 4.58E+04 | 5.68E-04 | 1.24E-08 | 20.3 |
| H4sH17726P | 5.17E+04 | 4.19E-04 | 8.10E-09 | 27.6 |
| H4sH17730P | NB | NB | NB | NB |
| H4sH17363N | NB | NB | NB | NB |
| H4sH17364N | NB | NB | NB | NB |
| H4sH17368N2 | 8.31E+05 | 1.92E-03 | 2.30E-09 | 6.0 |
| H4sH17368N3 | 7.12E+05 | 1.22E-03 | 1.71E-09 | 9.5 |
| H4sH17930N | NB | NB | NB | NB |
| H4sH17930N2 | NB | NB | NB | NB |
| H4sH21051P | 1.37E+04 | 3.31E-04 | 2.41E-08 | 34.9 |
| H4sH21054P | 1.98E+05 | 7.65E-04 | 3.86E-09 | 15.1 |
| H4sH21055P | 1.56E+05 | 1.21E-03 | 7.76E-09 | 9.6 |
| H4sH21058P | 2.46E+05 | 2.60E-04 | 1.06E-09 | 44.5 |
| H4sH21064P | NB | NB | NB | NB |
| H4sH21073P | 5.77E+05 | 1.15E-04 | 2.00E-10 | 100.3 |
| H4sH21077P | NB | NB | NB | NB |
| H4sH21079P | NB | NB | NB | NB |
| H4sH21080P | NB | NB | NB | NB |
| H4sH21083P | 5.38E+04 | 2.12E-04 | 3.94E-09 | 54.5 |
| H4sH21086P | 6.97E+04 | 1.14E-03 | 1.63E-08 | 10.2 |
| H4sH21090P | 8.11E+04 | 1.91E-04 | 2.35E-09 | 60.6 |
| H4sH21091P | 1.74E+05 | 1.46E-04 | 8.42E-10 | 79.1 |
| H4sH21093P | 1.18E+05 | 1.92E-03 | 1.63E-08 | 6.0 |
| H4sH21099P | 1.24E+05 | 9.79E-05 | 7.88E-10 | 118.0 |
| H4sH21100P | 2.90E+05 | 1.82E-04 | 6.26E-10 | 63.5 |
| H4sH21103P | 8.35E+05 | 3.22E-03 | 3.86E-09 | 3.6 |
| H4sH21104P | 4.36E+04 | 2.15E-04 | 4.94E-09 | 53.7 |

*NB indicates that under experimental conditions, HLA-A2:HPV16E7(82-90) peptide reagent did not bind to the captured anti-HLA-A2:HPV16E7 monoclonal antibody The data demonstrate that a majority of the anti-HLA-A2/HPV16E7 antibodies of this invention selectively bound to soluble HLA-A2/HPV16E7 peptide complex, some displaying sub-nanomolar affinity. Some antibodies, however, displayed no binding to the HLA-A2/HPV16E7 complex.

Example 5: Prediction of Potential Off-Target Peptides

Given a target 9-mer peptide-HLA-A2 complex, an associated potential off-target peptide is defined based on three criteria: A) the peptide is a 9-mer and is predicted to bind HLA-A2, B) the peptide is similar to the target peptide based on sequence homology, and C) the peptide is derived from a gene that is expressed in essential, normal tissues. Therefore, to predict potential off-target peptides associated with YMLDLQPET (HPV16 E711-19; SEQ ID NO: 538) and LLMGTLGIV (HPV16 E782-90; SEQ ID NO:539) the following methodology was used (generally see, Dhanik, Ankur, et al. (2016) BMC Bioinformatics 17(1):286).

As a first step, canonical human protein sequences were downloaded from the UniprotKB database (version September 2014) (Magrane, Michele, and UniProt Consortium. Database 2011 (2011): bar009) and all 9-mers were extracted. This resulted in 11,118,076 peptides from 20,014 protein sequences.

Next, the binding affinities of the peptides with HLA-A2 were computed using NetMHCstab webserver (version 1.0) (Jørgensen, Kasper W., et al. (2014) Immunology 141(1): 18-26). Peptides with affinity value <500 nM were predicted to bind HLA-A2, and the rest were discarded resulting in the remaining 338,452 peptides.

The peptide sequences were then evaluated for sequence homology with the target peptide. For each peptide, its Degree of Similarity (DoS) was calculated to the target peptide. The DoS value represents the number of identical amino acids at identical positions between the two peptides. Peptides with DoS value <6 were rejected resulting in the remaining 21 peptides in the case of HLA-A2/HPV16E7: 11-19 and 78 peptides in the case of HLA-A2/HPV16E7: 82-90.

The genes corresponding to the 21 peptides were checked for their expression in the essential, normal tissues. The evaluation for the expression was done using the gene expression data derived from the GTEx (Gene Tissue Expression) and TCGA (The Cancer Genome Atlas) databases as provided by OmicSoft (Hu, Jun, et al. Bioinformatics (2012) 28(14):1933-1934). The data was available in RPKM (Reads Per Kilobase Per Million) values from 497 TCGA adjacent normal samples (across 15 essential tissue types), and 2,928 GTEx normal samples (across 22 essential tissue types). Tissues other than the breast, cervix, fallopian tube, testis, uterus, and vagina, were considered essential. A gene was considered to be expressed in the essential, normal tissues if the maximum of the 95 percentile expression in each essential, normal tissue type in the GTEx and TOGA databases is >=0.5 RPKM. For HLA-A2/HPV16E7:11-19 (YMLDLQPET) (SEQ ID NO:538), out of the 21 peptides, 10 peptides were derived from genes that are expressed in the essential, normal tissues. For HLA-A2/HPV16E7:82-90 (LLMGTLGIV) (SEQ ID NO: 539), out of the 78 peptides, 49 peptides were derived from genes that are expressed in the essential, normal tissues.

The 10 peptides constitute the predicted off-targets associated with the target YMLDLQPET (SEQ ID NO:538)-HLA-A2 complex (Table 7). Out of the 49 potential peptides predicted to constitute likely off-targets associated with the LLMGTLGIV (SEQ ID NO: 539)-HLA-A2 complex, 13 were picked at random for experimental validation and are listed in Table 8.

TABLE 7

Predicted off-target peptides similar to HLA-A2/HPV16E7:11-19 (YMLDLQPET; SEQ ID NO: 538)

| No. | Peptide Sequence | Peptide Name | Gene | Predicted IC50 (nM) |
|---|---|---|---|---|
| 1 | YMLDLQKQL (SEQ ID NO: 546) | SH3GLB1:244-252 | SH3GLB1 | 9.2 |
| 2 | KMLDKNPET (SEQ ID NO: 547) | CAMKK1:388-396 | CAMKK1 | 107.9 |
| 3 | YMFDLLLET (SEQ ID NO: 548) | USP47:691-699 | USP47 | 3.5 |
| 4 | YTLDLQLEA (SEQ ID NO: 549) | CHPF:463:471 | CHPF | 132.8 |
| 5 | MMLILQAET (SEQ ID NO: 550) | PKD1:2694-2702 | PKD1 | 244.3 |
| 6 | LMLPLQPCT (SEQ ID NO: 551) | NBR1:357-365 | NBR1 | 487.8 |
| 7 | YILDLLPDT (SEQ ID NO: 552) | CBL:83-91 | CBL | 145.9 |
| 8 | YMEDLQELT (SEQ ID NO: 553) | PPP4R4:20-28 | PPP4R4 | 482.1 |
| 9 | GLLDLDPET (SEQ ID NO: 554) | SBK3:285-293 | SBK3 | 91.6 |
| 10 | VMKDLLPET (SEQ ID NO: 555) | FNDC3B:921-929 | FNDC3B | 379.9 |

TABLE 8

Predicted off-target peptides similar to HLA-A2/HPV16E7:82-90 (LLMGTLGIV; SEQ ID NO: 539)

| No. | Peptide Sequence | Peptide Name | Gene | Predicted IC50 (nM) |
|---|---|---|---|---|
| 1 | LLMGTFLSV (SEQ ID NO: 556) | VPREB3:9-17 | VPREB3 | 5.9 |
| 2 | LLGGTLERV (SEQ ID NO: 557) | B4GALT2:4-12 | B4GALT2 | 93.6 |
| 3 | LLMGSNTIV (SEQ ID NO: 558) | GCAT:312-320 | GCAT | 13.2 |
| 4 | LLQATLDIV (SEQ ID NO: 559) | CYP39A1:246-254 | CYP39A1 | 88.7 |
| 5 | LLLTFLGIV (SEQ ID NO: 560) | ALDH3A2:467-475 | ALDH3A2 | 85.4 |
| 6 | LLAGTLAGV (SEQ ID NO: 561) | CLCN4:79-87 | CLCN4 | 11.0 |
| 7 | LLQDTLGHV (SEQ ID NO: 562) | ZHX2:234-242 | ZHX2 | 50.5 |
| 8 | LLLAVLGIV (SEQ ID NO: 563) | GRM6:590-598 | GRM6 | 64.4 |
| 9 | LVMETLCIV (SEQ ID NO: 564) | IPO9:582-590 | IPO9 | 18.8 |
| 10 | LLNETLGEV (SEQ ID NO: 565) | IPO4:163-171 | IPO4 | 25.8 |
| 11 | KLMGHLGVV (SEQ ID NO: 566) | SF3B1:969-977 | SF3B1 | 11.2 |
| 12 | LLMCYLYIV (SEQ ID NO: 567) | DOCK11:1282-1290 | DOCK11 | 2.7 |
| 13 | LLNKVLGIV (SEQ ID NO: 568) | Human CNOT1:1962-1970 | CNOT1 | 247.8 |

Example 6: T2 Peptide Pulsing to Determine HLA-A2/HPV16E7 M Specificity

To determine anti-HLA-A2/HPV16E7 monoclonal antibody specificity, peptide-pulsed T2 cells loaded with target or off-target peptides (identified in the previous Example) were used. Experiments were carried out as follows: For the exogenous loading of HPV16E7 target or off-target peptides, T2 cells were rinsed in AIM V® Medium and counted with a Cellometer™ Auto T4 cell counter (Nexcelom Bioscience). Approximately 6 million T2 cells per T-75 flask were cultured for 24 hours at 26° C. in 9 mL of AIM V® Medium containing 10 µg of human b2m and 100 µg of HPV16E7 peptide or off-target peptide (Tables 6 and 7). Peptide-loaded T2 cells were washed once with PBS without Ca2+/Mg2+ and counted. Approximately 10,000 cells per well of the peptide-loaded T2 or untreated T2 in cell washing buffer were seeded into the 96-well carbon electrode plates (MULTI-ARRAY high bind plate, MSD) and incubated for 1 hour at 37° C. to allow cells to adhere to the plate. Nonspecific binding sites were blocked using 2% BSA (w/v) in PBS for 1 hour at room temperature. To the plate-bound cells, solutions of anti-HLA-A2/HPV16E7:11-19, anti-HLA-A2/HPV16E7:82-90 or control antibody in serial dilutions ranging from 1.7 pM to 100 nM, as well as solutions without antibody were added. Plates were incubated for 1 hour at room temperature, then washed to remove the unbound antibody using an AquaMax2000 plate washer (MDS Analytical Technologies). Plate-bound antibodies were detected with SULFO-TAG™-conjugated goat polyclonal anti-human IgG antibody specific for the Fc gamma fragment (Jackson Immunoresearch, Meso Scale Discovery) for 1 hour at room temperature. After washes, the plates were developed with the Read Buffer (MSD) according to manufacturer's recommended procedure, and the luminescent signals were recorded with a SECTOR Imager 600 (Meso Scale Discovery) instrument. The luminescence intensity, measured in relative light units (RLU), was recorded to indicate the binding intensity of each antibody at the range of concentrations. The ratio of cell binding signal for each anti-HLA-A2/HPV16E7 antibody compared to isotype control at 11 nM, is reported in Tables 8 and 9 and is an indication of specificity. At 11 nM concentration most antibodies displayed minimal binding to T2 untreated cells. Not all antibodies were tested with all corresponding related off-target peptides. Those not tested are marked as NT for "Not Tested". Antibodies with a binding ratio of greater than 15 are marked (+++), with a ratio equal to or less than 15 but greater than or equal to 10 are marked (++), with a ratio less than 10 but greater than or equal to 3 are marked (+) and antibodies with a binding ratio less than 3 were classified as non-binders and denoted as (−). In addition, direct binding signals (in RLU) were analyzed as a function of the antibody concentration and data fitted to a sigmoidal (four-parameter logistic) dose-response model using Graph Pad Prism™. The $EC_{50}$ values, defined as the concentration of antibody at which 50% of the maximal binding signal on cells is detected, were determined, where possible, to indicate potency of each antibody. $EC_{50}$ values for binding to cell-surface HLA-A2/HPV16E7:11-19 or HLA-A2/HPV16E7:82-90 only, are also reported in Tables 9 and 10.

Ten of 13 anti-HLA-A2/HPV16E7:11-19 antibodies of the invention bind to T2 cell-surface HLA-A2/peptide complex. Seven of these 10 antibodies (H4sH17670P; H4sH17675P; H4sH17363N; H4sH17364N; H4sH17930N; H4sH17930N2; and H4sH21064P are specific for the HLA-A2/HPV16E7:11-19 complex. Three antibodies (H4sH17672P, H4sH21079P, H4sH21080P) showed displayed higher potency with $EC_{50}$ values below 1.1 nM. Three antibodies (H4sH17673P, H4sH17680P, H4sH17697P) did not bind to T2 peptide loaded cells and are denoted with a (−) in the first column of Table 9.

The cell binding results on T2 cells loaded with HPV16E7:82-90 target and predicted off-target peptides are summarized in Table 9. Sixteen of 21 anti-HLA-A2/HPV16E7:82-90 mAbs of the invention bound T2 cell-surface HLA-A2/peptide complex. Only 2 mAbs from this group (H4sH17368N2, H4sH21086P) showed specificity to the HLA-A2/HPV16E7 82-90 complex. Five antibodies (H4sH17730P, H4sH21051P, H4sH21054P, H4sH21055P, H4sH21077P) did not bind to T2 peptide loaded cells and are denoted with a (−) in the Table 10.

TABLE 9

Binding Specificity of Anti-HLA-A2/HPV16E7:11-19 Monoclonal Antibodies

| AbPID | Cell Binding EC50 (M) T2 + HPV16E7 11-19 | T2 + peptide cell binding specificity compared to irrelevant hIgG4s isotype control at 11 nM | | | | | | | | | | |
|---|---|---|---|---|---|---|---|---|---|---|---|---|
| | | HPV16E7 11-19 | SH3GLB1 244-252 | CAMKK1 388-396 | USP47 691-699 | CHPF 463-471 | PKD1 2694-2702 | NBR1 357-365 | CBL 83-91 | PPP4R4 20-28 | SBK3 285-293 | T2 untreated |
| H4sH17670P | 1.3E−09 | ++ | − | − | − | − | − | − | − | − | − | − |
| H4sH17672P | 4.5E−10 | ++ | − | − | + | − | − | − | − | − | − | − |
| H4sH17673P | − | − | − | − | − | − | − | − | − | − | − | − |
| H4sH17675P | 1.1E−09 | + | − | − | − | − | − | − | − | − | − | − |
| H4sH17680P | − | − | − | − | − | − | − | − | − | − | − | − |
| H4sH17697P | − | − | − | − | − | − | − | − | − | − | − | − |
| H4sH17363N | 2.1E−09 | ++ | − | − | − | − | − | − | − | − | − | − |
| H4sH17364N | 2.0E−09 | ++ | − | − | − | − | − | − | − | − | − | − |
| H4sH17930N | 3.1E−09 | ++ | − | − | − | − | − | − | − | − | − | − |
| H4sH17930N2 | 5.8E−09 | ++ | − | − | − | − | − | − | − | − | − | − |
| H4sH21064P | 2.2E−09 | +++ | NT | NT | NT | − | NT | − | − | NT | NT | − |
| H4sH21079P | 1.1E−09 | +++ | NT | NT | NT | + | NT | − | + | NT | NT | − |
| H4sH21080P | 2.2E−10 | ++ | NT | NT | NT | + | NT | − | + | NT | NT | − |
| | | Cell binding signal at 11 nM, RLU | | | | | | | | | | |
| Isotype Ctrl. | − | 1029 | 976 | 772 | 1102 | 1077 | 1123 | 820 | 1104 | 1038 | 945 | 847 |

TABLE 10

Binding Specificity of Anti-HLA-A2/HPV16E7:82-90 Monoclonal Antibodies

| AbPID | Cell Binding EC50 (M) T2 + HPV16E7 82-90 | T2 + peptide cell binding specificity compared to irrelevant hIgG4s isotype control at 11 nM | | | | | | | |
|---|---|---|---|---|---|---|---|---|---|
| | | HPV16E7 82-90 | VPREB3 9-17 | B4GALT2 4-12 | GCAT 312-320 | CYP39A1 246-254 | ALDH3A2 467-475 | CLCN4 79-87 | ZHX2 234-242 |
| H4sH17707P | 2.3E−08 | + | − | − | − | − | − | − | + |
| H4sH17715P | 2.9E−10 | ++ | − | − | − | − | + | − | − |
| H4sH17726P | 4.1E−10 | ++ | +++ | ++ | − | ++ | + | ++ | + |
| H4sH17730P | − | − | − | − | − | − | − | − | − |
| H4sH17368N2 | 7.5E−10 | ++ | − | − | − | − | − | − | − |
| H4sH17368N3 | 1.8E−10 | ++ | − | − | − | − | − | + | − |
| H4sH21051P | − | − | − | − | NT | NT | NT | NT | − |
| H4sH21054P | − | − | − | − | NT | NT | NT | NT | − |
| H4sH21055P | − | − | − | − | NT | NT | NT | NT | − |
| H4sH21077P | − | − | − | − | NT | NT | NT | NT | − |
| H4sH21086P | 5.0E−10 | +++ | − | − | NT | NT | NT | NT | − |
| H4sH21090P | 5.6E−10 | +++ | − | − | NT | NT | NT | NT | +++ |
| H4sH21091P | 1.7E−10 | +++ | − | − | NT | NT | NT | NT | +++ |
| H4sH21093P | 3.0E−10 | ++ | − | − | NT | NT | NT | NT | + |
| H4sH21058P | 1.9E−10 | ++ | − | − | − | − | − | − | − |
| H4sH21073P | 9.0E−11 | ++ | − | − | − | − | − | − | − |
| H4sH21083P | 3.3E−10 | ++ | − | − | − | − | + | − | − |
| H4sH21099P | 8.7E−11 | ++ | − | − | − | − | + | − | − |
| H4sH21100P | 9.6E−11 | ++ | − | − | − | − | − | − | − |
| H4sH21103P | 4.5E−11 | ++ | − | − | − | − | + | − | − |
| H4sH21104P | 4.8E−10 | ++ | − | − | − | + | − | − | − |
| | | Cell binding signal at 11 nM, RLU | | | | | | | |
| Isotype Ctrl. | − | 835 | 871 | 926 | 872 | 562 | 856 | 725 | 797 |

| AbPID | T2 + peptide cell binding specificity compared to irrelevant hIgG4s isotype control at 11 nM | | | | | | |
|---|---|---|---|---|---|---|---|
| | GRM6 590-598 | IPO9 582-590 | IPO4 163-171 | SF3B1 969-977 | DOCK11 1282-1290 | CNOT1 1962-1970 | T2 Non-Pulsed |
| H4sH17707P | − | − | − | − | − | − | − |
| H4sH17715P | ++ | − | − | + | − | + | − |
| H4sH17726P | ++ | + | − | + | + | + | − |
| H4sH17730P | − | − | − | − | − | − | − |
| H4sH17368N2 | − | − | − | − | − | − | − |
| H4sH17368N3 | − | − | − | − | − | − | − |
| H4sH21051P | NT | NT | NT | NT | NT | NT | − |
| H4sH21054P | NT | NT | NT | NT | NT | NT | − |
| H4sH21055P | NT | NT | NT | NT | NT | NT | − |
| H4sH21077P | NT | NT | NT | NT | NT | NT | − |
| H4sH21086P | NT | NT | NT | NT | NT | NT | − |
| H4sH21090P | NT | NT | NT | NT | NT | NT | − |
| H4sH21091P | NT | NT | NT | NT | NT | NT | − |
| H4sH21093P | NT | NT | NT | NT | NT | NT | − |
| H4sH21058P | + | − | − | + | − | − | − |
| H4sH21073P | + | − | − | − | − | − | − |
| H4sH21083P | + | − | − | ++ | − | + | − |
| H4sH21099P | + | − | − | + | − | + | − |
| H4sH21100P | + | − | − | + | − | − | − |
| H4sH21103P | + | ++ | + | +++ | ++ | ++ | − |
| H4sH21104P | − | − | − | + | − | − | − |
| | Cell binding signal at 11 nM, RLU | | | | | | |
| Isotype Ctrl. | 807 | 768 | 1067 | 702 | 776 | 780 | 860 |

As shown in Tables 9 and 10, anti-HLA-A2:HPV16E7 antigen-binding proteins of the invention bound with high specificity only to the specific HPV peptide (SEQ ID No: 538 in Table 9, or to SEQ ID NO: 539 in Table 10) as presented by HLA-A2 and did not bind to any off-target peptides presented by HLA-A2.

Example 7: Binding Specificity Analysis Using Peptide Pulsed T2 Cells & FACS Analysis Relative binding and specificity of HPV16E7 antibodies were accessed by flow cytometry on NIH3T3 cells expressing HLA-A2 complex presenting either HPV 11-19 peptide (3T3/HLA.A2/hB2M/HPV16E7:11-19) or HPV 82-90 peptide (3T3/HLA.A2/hB2M/HPV16E7 (82-90). NIH3T3 cells expressing HLA complex was generated by transfecting human HLA.A2 (accession number P01892), human B2M (accession number NP_004039.1) and an ubiquitin peptide cassette (Levy F., et al. (1996) *Proceedings of the National Academy of Sciences of the United States of America* 93(10): 4907-4912; Valmori D, et al. (1999) *Journal of Experimental Medicine* 189(6):895-906) comprising either amino acids 11-19 of HPV16E7 (SEQ ID NO: 538) or amino acids 82-90 (SEQ ID NO: 539) (accession number AKI85233) using lipofectomine 2000 (Invitrogen, Cat #11668) followed by selection for at least 2 weeks in 1 μg/ml puromycin, 500 μg/ml G418, and 100 μg/ml hygromycin. To stain, cells were harvested using cell dissociation buffer (Millipore, Cat

S-004-C) and counted. Cells were plated in staining buffer (PBS, without Calcium and Magnesium (Irving 9240)+2% FBS (ATCC 30-2020) at a density of 200,000 cells per well in a 96-well V-Bottom plate and stained with three-fold serial dilutions (1.7 pM-100 nM) of primary antibodies for 30 min. at 4° C. Following primary antibody incubation, cells were washed once in staining buffer, and stained with an Alexa-Flour 647 conjugated secondary antibody (Jackson ImmunoResearch, Cat #109-606-170) at 10 µg/ml for 30 mins at 4° C. Cells were then washed and fixed using a 50% solution of BD Cytofix (BD, Cat #554655) diluted in staining buffer. Samples were run and analyzed on an intellicyt iQue flow cytometer to calculate mean fluorescence intensity (MFI). MFI values were plotted in Graphpad Prism using a four-parameter logistic equation over a 12-point response curve to calculate $EC_{50}$ values. The secondary antibody alone (i.e. no primary antibody) for each dose-response curve is also included in the analysis as a continuation of the three-fold serial dilution and is represented as the lowest dose. $EC_{50}$ values (M) and max fold binding (fold changed from highest dose to lowest does) are shown in Table 11. Several antibodies specifically bound to either the 3T3/HLA.A2/hB2M/HPV16E7:11-19 or the 3T3/HLA.A2/hB2M/HPV16E7:82-90 cell line. $EC_{50}$ values ranged from 5-500 nM and fold binding ranged from 1.0× to 43.8×.

The specificity of six HPV16E7:11-19 antibodies was further characterized by assessing binding to T2 (174 CEM.T2) cells pulsed with HPV16E7:11-19, HPV16E7:82-90 or predicted off-target peptides (Table 7). To pulse, T2 (174 CEM.T2) were re-suspended in AIM V medium at a density of 1×106 cells/ml (Gibco. Cat #31035-025). Cells were pulsed by adding 10 µg/ml hB2M (EMD Millipore Cat #475828) and 100 µg/ml of the indicated peptide. T2 cells were then incubated overnight at 26° C., washed in staining buffer and stained with the indicated antibodies at a concentration of 10 µg/ml following the protocol described above. MFI values were calculated and presented as fold change over unstained cells. Relative binding of the six HPV16E7:11-19 antibodies on T2 cells pulsed with HPV16E7:11-19 range from 986-1200 fold above unstained cells. No significant binding above isotype control was observed on T2 cells pulsed with the other peptides (Table 12).

TABLE 11

FACS Binding of HPV16E7 antibodies

| Antibody Designation | 3T3/HLA.A2/hB2M/HPV16E7 (11-19) | | 3T3/HLA.A2/hB2M/HPV16E7 (82-90) | | HEK293 | |
|---|---|---|---|---|---|---|
| | $EC_{50}$ | Max Fold | $EC_{50}$ | Max Fold | $EC_{50}$ | Max Fold |
| *H4sH17363N | 1.40E−08 | 11.4 | ND | 1.7 | ND | 1.3 |
| *H4sH17364N | 2.40E−08 | 11.4 | 2.91E−08 | 2.3 | ND | 1.2 |
| H4sH17368N2 | ND | 1.8 | 1.94E−07 | 9.1 | ND | 1.8 |
| H4sH17368N3 | ND | 1.1 | 3.26E−08 | 6.1 | ND | 1.7 |
| *H4sH17670P | 2.37E−08 | 6.7 | ND | 1.5 | ND | 0.8 |
| H4sH17672P | 3.72E−08 | 10.2 | ND | 1.4 | ND | 1.6 |
| H4sH17673P | ND | 1.8 | ND | 1.3 | ND | 1.6 |
| *H4sH17675P | 1.27E−08 | 5.1 | ND | 1.3 | ND | 0.65 |
| H4sH17680P | ND | 1.5 | ND | 1.1 | ND | 1 |
| H4sH17697P | ND | 1.2 | ND | 1.5 | ND | 1.1 |
| H4sH17707P | ND | 1.5 | ND | 1.8 | ND | 2 |
| H4sH17715P | ND | 1.7 | 6.60E−06 | 6.7 | 3.47E−08 | 3.1 |
| H4sH17726P | 5.20E−08 | 28.11 | 7.19E−08 | 43.8 | ND | 2.0 |
| H4sH17730P | ND | 0.9 | 5.80E−08 | 2.9 | ND | 0.9 |
| H4sH17930N | 1.73E−08 | 13.5 | 6.62E−08 | 10.3 | 1.53E−07 | 4.3 |
| *H4sH17930N2 | 2.78E−08 | 11.4 | 7.48E−08 | 3 | 3.93E−08 | 3 |
| H4sH21051P | ND | 1.2 | ND | 2.0 | ND | 1.2 |
| H4sH21054P | ND | 3.8 | ND | 4.9 | 3.51E−08 | 3.6 |
| H4sH21055P | ND | 1.4 | ND | 1.5 | ND | 1.9 |
| H4sH21058P | ND | 1.3 | 1.01E−08 | 8.6 | ND | 0.9 |
| *H4sH21064P | 2.05E−08 | 12.3 | 6.60E−08 | 2.2 | ND | 0.7 |
| H4sH21073P | ND | 0.9 | 4.09E−08 | 6.5 | ND | 0.9 |
| H4sH21077P | ND | 2.0 | ND | 1.5 | ND | 1.6 |
| H4sH21079P | 4.02−08 | 26.6 | 5.40E−08 | 20.5 | ND | 1.3 |
| H4sH21080P | 3.10E−08 | 11.7 | 2.11E−08 | 7.4 | 5.19E−08 | 4.4 |
| H4sH21083P | ND | 1.5 | 3.31E−09 | 8.5 | ND | 1.4 |
| H4sH21086P | 5.537E−07 | 14.6 | 3.49E−07 | 22 | ND | 1.3 |
| H4sH21090P | ND | 1.6 | 1.85E−09 | 6.25 | ND | 1.1 |
| H4sH21091P | ND | 1.5 | 3.74E−10 | 5.6 | ND | 1.6 |
| H4sH21093P | ND | 1.9 | 2.95E−08 | 3.9 | ND | 1.4 |
| H4sH21099P | ND | 1 | 1.19E−09 | 4.8 | ND | 2 |
| H4sH21100P | 3.55E−08 | 4.4 | 1.19E−08 | 10.3 | ND | 0.7 |
| H4sH21103P | ND | 1.6 | 9.20E−09 | 6.3 | ND | 1.5 |
| H4sH21104P | ND | 1.6 | 5.481E−09 | 8.5 | ND | 1 |
| Isotype Ctrl | ND | 1 | ND | 1 | ND | 1.2 |

Antibodies with (*) were run together in a separate experiment
ND = $EC_{50}$ Not Determined when max fold binding was less than or equal to 2 fold

TABLE 12

| | HPV16E7:11-19 YMLDLQPET | SH3GLB1 244-252 | CAMKK1 388-396 | USP47 691-699 | CHPF 463:471 | PKD1 2694-2702 | NBR1 357-365 | CBL 83-91 | PPP4R4 20-28 | SBK3 285-293 | Unpulsed Cells |
|---|---|---|---|---|---|---|---|---|---|---|---|
| H4sH17363N | 1001.4 | 13.6 | 2.0 | 0.6 | 7.4 | 1.2 | 3.6 | 19.5 | 6.1 | 0.4 | 8.5 |
| H4sH17364N | 986.1 | 15.2 | 1.0 | 1.3 | 10.9 | 1.0 | 3.0 | 23.9 | 9.0 | 0.8 | 11.7 |
| H4sH17670P | 1005.5 | 3.7 | 2.9 | 5.3 | 3.6 | 3.5 | 2.2 | 2.0 | 2.9 | 2.6 | 5.0 |
| H4sH17675P | 1204.2 | 10.5 | 2.4 | 13.3 | 5.0 | 2.9 | 2.2 | 4.9 | 5.5 | 2.9 | 7.2 |
| H4sH17930N2 | 1166.7 | 28.2 | 2.6 | 8.9 | 7.5 | 3.3 | 3.3 | 4.6 | 7.3 | 3.0 | 6.7 |
| H4sH21064P | 1204.2 | 10.5 | 2.4 | 13.3 | 5.0 | 2.9 | 2.2 | 4.9 | 5.5 | 2.9 | 7.2 |
| Isotype Ctrl | 17.1 | 8.5 | 6.3 | 11.5 | 9.9 | 9.8 | 8.7 | 9.0 | 8.0 | 6.8 | 10.2 |
| Secondary Alone | 14.2 | 3.7 | 5.8 | 5.2 | 4.8 | 4.4 | 3.7 | 4.4 | 4.0 | 4.1 | 6.5 |
| Unstained | 1.0 | 1.0 | 1.0 | 1.0 | 1.0 | 1.0 | 1.0 | 1.0 | 1.0 | 1.0 | 1.0 |

FACS Binding of HPV16E7 antibodies to T2 pulsed cells. (Fold change over unstained)

Example 8: Epitope Analysis Using Alanine Scanning Peptides

Alanine scanning was performed to determine which residues in the HPV16E7:11-19 peptide were critical for antibody binding. T2 cells were pulsed with alanine scanning peptides and stained with HPV16E7:11-19 antibodies as described above. The following alanine scanning peptides were used (Table 13).

TABLE 13

Alanine scanning peptides used in the study

| SEQ ID NO: | Peptide | Ala substitution |
|---|---|---|
| 569 | AMLDLQPET | Y11A |
| 570 | YALDLQPET | M12A |
| 571 | YMADLQPET | L13A |
| 572 | YMLALQPET | D14A |
| 573 | YMLDAQPET | L15A |
| 574 | YMLDLAPET | Q16A |
| 575 | YMLDLQAET | P17A |
| 576 | YMLDLQPAT | E18A |
| 577 | YMLDLQPEA | T19A |

Conversion of aspartate 14 to alanine (D14A) and glutamine 16 to alanine (Q16A) drastically reduced antibody binding for all the tested antibodies. Conversion of tyrosine 11 to alanine (Y11A) reduced binding of H4sH17670P, H4sH17675P, H4sH21064P, and H4sH17930N2; but not H4sH17363N or H4sH17364N. Conversion of leucine 13 to alanine (L13A) and proline 17 to alanine (P17A) reduced overall antibody binding (Table 14).

To summarize, D14 and Q16 are critical residues for antibody binding.

TABLE 14

FACS Binding of HPV16E7 antibodies to T2 cells pulsed with alanine scanning peptides

| | AMLDLQPET (SEQ ID NO: 569) (Y11A) | YALDLQPET (SEQ ID NO: 570) (M12A) | YMADLQPET (SEQ ID NO: 571) (L13A) | YMLALQPET (SEQ ID NO: 572) (D14A) | YMLDAQPET (SEQ ID NO: 573) (L15A) |
|---|---|---|---|---|---|
| H4sH17363N | 694.8 | 998.5 | 529.9 | 58.2 | 1019.3 |
| H4sH17364N | 708.3 | 997.9 | 489.9 | 69.7 | 1008.4 |
| H4sH17670P | 8.1 | 670.3 | 374.9 | 10.7 | 1062.8 |
| H4sH17675P | 19.0 | 823.8 | 527.2 | 6.3 | 1153.1 |
| H4sH17930N2 | 39.0 | 972.9 | 665.7 | 5.8 | 1245.9 |
| H4sH21064P | 19.0 | 823.8 | 527.2 | 6.3 | 1153.1 |
| Isotype Ctrl | 14.4 | 10.9 | 8.4 | 9.9 | 8.1 |
| Secondary Alone | 9.7 | 6.9 | 4.9 | 6.4 | 6.3 |
| Unstained | 1.0 | 1.0 | 1.0 | 1.0 | 1.0 |

| | YMLDLAPET (SEQ ID NO: 574) (Q16A) | YMLDLQAET (SEQ ID NO: 575) (P17A) | YMLDLQPAT (SEQ ID NO: 576) (E18A) | YMLDLQPEA (SEQ ID NO: 577) (T19) |
|---|---|---|---|---|
| H4sH17363N | 13.3 | 401.8 | 775.7 | 1034.3 |
| H4sH17364N | 13.2 | 384.8 | 756.2 | 1075.7 |
| H4sH17670P | 6.2 | 168.8 | 614.7 | 1150.1 |
| H4sH17675P | 5.8 | 371.1 | 808.3 | 1165.0 |
| H4sH17930N2 | 6.8 | 531.9 | 1035.4 | 1330.3 |
| H4sH21064P | 5.8 | 371.1 | 808.3 | 1165.0 |
| Isotype Ctrl | 9.0 | 8.2 | 9.1 | 9.6 |
| Secondary Alone | 5.5 | 4.6 | 4.5 | 6.5 |
| Unstained | 1.0 | 1.0 | 1.0 | 1.0 |

Example 9: Reformatting HLA-A2/HPV16E7 Antibodies into ScFv for Use in Chimeric Antigen Receptors Six HLA-A2/HPV16E7:11-19 antibodies (17363N, 17364N, 17670P, 17675P, 17930N2 and 21064P) were reformatted into VL-VH single chain variable fragments (ScFv) and placed into a chimeric antigen receptor (CAR) construct that used a CD8a hinge and transmembrane domain, 4-1 BB costimulatory domain, and a CD3 stimulatory domain (SEQ ID NOs: 540-545). The HLA-A2/HPV16E7:11-19 specific CARs were cloned into a lentiviral expression vector (Lenti-X™ Bicistronic Expression System (Neo), Clontech Cat #632181) and lentiviral particles were generated via the Lenti-X Packaging Single-Shot (VSV-G) system (Clontech Cat #631276) according to manufacturer protocols. Jurkat cells engineered to express an NFAT-luciferase reporter (Jurkat/NFATLuc c1.3C7) were then transduced with the 6 different CAR constructs using RetroNectin® Pre-coated Dishes (Clontech, Cat #T110a) according to manufacturer's protocols. Following selection for at least 2 weeks in 500 µg/ml G418 (Gibco, Cat #11811-098), CAR-T cell lines were generated.

Activity of CAR-T lines was assessed in a CAR-T/Antigen Presenting Cell (APC) bioassay.

To perform the bioassay, 50,000 Jurkat/NFATLuc cl. 3C7 CAR-T cells were added to Thermo-Nunc 96-well white plates (Thermo Scientific, Cat #136101) in 50 µl of assay media (RPMI media with 10% FBS and 1% P/S/G) followed by the addition of a 3-fold serial dilution of APCs (150,000 cells to 200 cells) in 50 µl of assay media. The following APCs were utilized: CASKI (HLA-A2+/HPV16+), CASKI cells overexpressing a single chain version of HLA-A2 presenting the 11-19 or 82-90 peptide, HEK293 (HLA-A2+/HPV16−), or C33a (HLA-A2+/HPV16−). The cell mixture was incubated in a 37° C., 5% $O_2$, humidified incubator for 5 hours. NFAT-Luciferase activity was measured using Promega One-Glo (Cat #E6130) and a Perkin Elmer Envision plate reader. Relative luciferase units (RLU) were generated and plotted in Graphpad Prism using a four-parameter logistic equation over an 8-point response curve to calculate $EC_{50}$ values. The zero APC condition for each dose-response curve is also included in the analysis as a continuation of the three-fold serial dilution and is represented as the lowest dose. Max fold activation was determined by taking the ratio of the highest RLU on the curve to the lowest. All six HLA-A2/HPV16E7:11-19 CAR-T cell lines were activated by CASKI cells that overexpressed the HPV16E7:11-19 peptide with max fold activations between 2.5-32.3 fold. No CAR-T cell lines were activated by the APCs that overexpressed the HPV16E7:82-90 peptide or HEK293 and C33a cells. Interestingly, one CAR-T cell line, that used the ScFv from antibody 17675P was activated by native CASKI cells with a fold activation of 4.1 and an $EC_{50}$ of 68654 cells (Table 15).

TABLE 15

Activation of HPV16E7 (11-19) CAR-T's in a CAR-T/APC Bioassay

| | Jurkat/NFATLuc Chimeric Antigen Receptor Construct | | | | | | | | | | |
|---|---|---|---|---|---|---|---|---|---|---|---|
| | 17363N | | 17364N | | 17670P | | 17675P | | 17930N2 | | 21064P | |
| APC | EC50 (cells) | Fold Activation | EC50 (cells) | Fold Activation | EC50 (cells) | Fold Activation | EC50 (cells) | Fold Activation | EC50 (cells) | Fold Activation | EC50 (cells) | Fold Activation |
| CASKI | ND | 0.9 | ND | 1 | ND | 0.8 | 68654 | 4.1 | ND | 0.9 | ND | 1.2 |
| CASKI 11-19 | 5108 | 2.5 | 6632 | 10.4 | 4145 | 8.5 | 9703 | 32.3 | 7885 | 16.8 | 7220 | 20.7 |
| CASKI 82-90 | ND | 0.9 | ND | 1 | ND | 0.9 | ND | 1.5 | ND | 0.7 | ND | 0.9 |
| HEK293 | ND | 0.8 | ND | 0.9 | ND | 0.8 | ND | 0.7 | ND | 0.7 | ND | 0.8 |
| C33a | ND | 0.7 | ND | 1.2 | ND | 0.8 | ND | 0.6 | ND | 0.6 | ND | 0.4 |

ND = EC50 Not Determined when max fold binding was less than or equal to 2-fold

Increasing the amount of HPV16E7:11-19 presented peptide HLA-A2 should result in an increase in the activation of the HLA-HPV16E7:11-19 CARs. It has been reported that interferon gamma can increase antigen presentation by MHC class 1 molecules though up-regulation of the proteasome (Früh K. and Yang Y. (1999) *Curr Opin Immunol.* 11(1):76-81). Based on this observation, it was determined whether wildtype CASKI cells or HEK293 cells pre-treated with interferon gamma could result in increased activation of the CAR-T cell lines. CASKI cells and HEK293 cells were pretreated with 500 units/ml recombinant human IFN-γ (Peprotech Cat #300-02) for 48 hours and then used in the CAR-T/APC bioassay as described above (Table 16). IFNγ pretreated CASKI cells activate all 6 HPV16E7:11-19 CAR-T cell lines with a fold activation ranging from 2.4-10.6

TABLE 16

Activation of HPV16E7 (11-19) CAR-T's in the presence of IFN-γ

| Jurkat/ NFATLuc CART | CASKI | | CASKI + IFN-g | | HEK293 | | HEK293 + IFN-g | |
|---|---|---|---|---|---|---|---|---|
| | $EC_{50}$ (cells) | Max Fold | $EC_{50}$ (cells) | Max Fold | $EC_{50}$ (cells) | Max Fold | $EC_{50}$ (cells) | Max Fold |
| 17363N | ND | 1.0 | 51837 | 2.4 | ND | 1.0 | ND | 0.81 |
| 17364N | ND | 1.0 | 6440 | 5.6 | ND | 0.86 | ND | 0.75 |
| 17670P | ND | 1.0 | 51360 | 2.7 | ND | 0.77 | ND | 0.78 |
| 17675P | 13844 | 1.77 | 64903 | 10.6 | ND | 0.81 | ND | 0.71 |

TABLE 16-continued

Activation of HPV16E7 (11-19) CAR-T's in the presence of IFN-γ

| Jurkat/ | CASKI | | CASKI + IFN-g | | HEK293 | | HEK293 + IFN-g | |
|---|---|---|---|---|---|---|---|---|
| NFATLuc CART | $EC_{50}$ (cells) | Max Fold | $EC_{50}$ (cells) | Max Fold | $EC_{50}$ (cells) | Max Fold | $EC_{50}$ (cells) | Max Fold |
| 17930N2 | ND | 0.97 | 57186 | 8.1 | ND | 0.75 | ND | 0.71 |
| 21064P | ND | 1.0 | 55863 | 8.97 | ND | 0.8 | ND | 0.7 |

ND = $EC_{50}$ Not Determined when max fold binding was less than or equal to 2-fold To further assess the specificity of the HPV16E7:11-19 CAR-T lines in the luciferase assay, we used T2 cells as the APC and pulsed with predicted off-target peptides (Table 17). Briefly, T2 cells were pulsed with a three-fold serial dilution of the indicated peptides (1.7 pg/ml to 100 ng/ml). Following pulsing, 50,000 CAR-T cells were added to Thermo-Nunc 96 well white plates (Thermo Scientific, Cat #136101) in 50 µL of assay media. Then, 50,000 pulsed T2 cells were added to the plates in 50 µL assay media. The cell mixture was incubated in a 37° C., 5% CO2, humidified incubator for 5 hours. NFAT-Luciferase activity was determined using Promega One-Glo™ (Cat #E6130) and a Perkin Elmer Envision plate reader. RLU were plotted in Graphpad Prism using a four-parameter logistic equation over a 12-point response curve to calculate $EC_{50}$ values. The un-pulsed condition for each dose-response curve is also included in the analysis as a continuation of the three-fold serial dilution and is represented as the lowest dose. Max fold activation was determined as described previously. All CAR-T cell lines were activated by T2 cells pulsed with the HPV16E7:11-19 peptide. The Jurkat/NFATLuc CART line utilizing the ScFv from antibody 17364N was activated non-specifically by T2 cells pulsed with Endophilin-B1 (SH3GLB1:244-252), Chondroitin sulfate synthase 2 (CHPF:463:471) and E3 ubiquitin-protein ligase CBL (CBL:83-91). All other CAR-T cells lines had no significant activation with any off-target peptide.

structures cover the sequence space of the six antibodies presented above (e.g. Table 11 and Table 12). All 9 residues of the HLA-displayed HPV16E7:11-19 peptide are clearly visible in the electron density maps for both 17670P and 17363N structures. Even at 2.9 Å (the resolution of the 17670P structure), the position and identity of the peptide residues is unambiguous, and residue-residue interactions can be determined accurately. The 17363P structure is 2.6 Å, allowing improved accuracy.

The 17670P and 17363N Fabs bind to the top of the HLA-peptide complex, in a manner very similar to the way that TCR binds. The Fabs are positioned and oriented almost identically to each other; both are aligned fairly parallel to the "rails" bordering the peptide binding groove, and both are centered on the bound peptide, with the heavy chain CDRs contacting the N terminal half of the bound peptide, and the light chain CDRs contacting the peptide's C terminal half. Other published antibody complex structures (e.g. PDB codes 1W72 and 4WUU) reveal that the antibody does not have to cover the entire HLA-displayed peptide. However, these antibodies with only partial peptide coverage have poor specificity, tolerating extensive changes in the part of the peptide that is not contacted with little loss in binding affinity.

The structures show that the 17670P and 17363N Fab heavy chains contact residues 11, 14, 15 in the HPV16E7 peptide, while the Fab light chains contact residues 15, 17, 18. No Fab contacts are made with side chains of residues

TABLE 17

Max Fold Activation of HPV16E7 (11-19) CAR-T's against T2 pulsed cells.

| | Jurkat/NFATLuc Chimeric Antigen Receptor Construct | | | | | |
|---|---|---|---|---|---|---|
| Peptide | 17363N | 17364N | 17670P | 17675P | 17930N2 | 21064P |
| | Max Fold Activation | | | | | |
| HPV16E7:11-19 | 6.5 | 10.9 | 1.9 | 10.6 | 7.8 | 12.9 |
| HPV16E7:82-90 | 0.9 | 0.9 | 0.9 | 0.9 | 0.9 | 0.8 |
| SH3GLB1:244-252 | 1.3 | 6.1 | 0.9 | 1.1 | 1.4 | 3.4 |
| CAMKK1:388-396 | 0.9 | 1.0 | 0.9 | 0.9 | 0.9 | 0.8 |
| USP47:691-699 | 1.0 | 0.9 | 0.9 | 1.0 | 0.9 | 1.1 |
| CHPF:463:471 | 1.1 | 5.2 | 0.9 | 1.0 | 0.9 | 1.1 |
| PKD1:2694-2702 | 0.8 | 0.9 | 1.0 | 1.0 | 0.9 | 0.9 |
| NBR1:357-365 | 0.9 | 0.9 | 0.9 | 0.9 | 0.9 | 0.9 |
| CBL:83-91 | 1.3 | 7.2 | 0.9 | 1.1 | 0.9 | 1.5 |
| PPP4R4:20-28 | 0.9 | 0.9 | 1.0 | 1.0 | 0.9 | 0.9 |
| SBK3:285-293 | 1.0 | 0.9 | 1.0 | 1.0 | 0.9 | 0.9 |

Example 10: Structural Analysis of Fab Binding to HLA-A2+HPV16E7:11-19 Peptide

In an effort to better understand the specific interactions between antibody and HLA-peptide complex, X-ray crystal structures of an antibody Fab fragment bound to HLA-A2/b2m displaying the HPV16E7:11-19 peptide were determined. One structure contains the 17670P Fab, and the other structure contains the 17363N Fab; together, these two 12, 13, 16, or 19 as they point toward the HLA molecule. The bound peptide is numbered according to the residue positions in the original HPV16 E7 protein, as follows:

(SEQ ID NO: 538)
Y   M   L   D   Q   P   E   T
11  12  13  14  15  16  17  18  19

The majority of Fab contacts are made with the peptide side chains, not the backbone.

Peptide contacts made by 17670P are concentrated almost exclusively in CDRs LCDR1 and HCDR3, particularly HCDR3. In particular, Fab heavy chain residues 100, 101, 102, 105, 109, 110 of SEQ ID NO: 34 and light chain residues 30, 31, 32, 50 of SEQ ID NO: 42 make contact with the bound peptide, while Fab heavy chain residues 28, 31, 32, 100, 102, 104, 109, 110, 113 of SEQ ID NO: 34 and light chain residues 31, 50, 52, 53, 54, 55, 92 of SEQ ID NO: 42 contact the HLA. "Contact" here can involve direct or water-mediated hydrogen bonds, charge-charge interactions, or hydrophobic/van der Waals interactions. For 17363N, Fab heavy chain residues 102, 103, 108, 111, 112 of SEQ ID NO: 506 and light chain residues 28, 30, 32, 50, 68 of SEQ ID NO: 514 contact the bound peptide, while Fab heavy chain residues 28, 32, 100, 102, 103, 107, 112 of SEQ ID NO: 506 and light chain residues 31, 49, 50, 51, 52, 53, 55, 92 of SEQ ID NO: 514 contact the HLA molecule.

Of the six anti-HLA-A2:HPV16E7:11-19 antibodies, 17675P is the most similar to 17670P in the CDR sequences that determine peptide binding, with 21064P and 17930N2 also sharing a high degree of similarity in the peptide-binding CDR regions. The key contacts between 17670P and the HLA-peptide complex are mostly conserved in 17675P, 21064P, and 17930N2, thus the binding mode of these antibodies is likely to be the same as that of 17670P.

In contrast, CDR H3 of 17363N has a very different sequence compared to CDR H3 from 17670P, and this sequence difference translates into a structural difference of CDR H3, altering contacts with the HLA-peptide complex in this region. For example, heavy chain Tyr 100 in 17670P contacts Tyr 11 of the bound peptide. The equivalent residue in 17363N is Tyr 102 (this antibody's CDR H3 is two residues longer) and this residue does not contact peptide Tyr 11. Instead, Tyr 102 has reoriented to make contacts with the HLA molecule nearby.

The lead antibody 17364N has a very similar sequence to 17363N, and is identical in all residues contacting the HLA-peptide complex. This antibody should have a binding mode very similar to that of 17363N, and thus different from 17670P, 17675P, 17930N2, and 21064P.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

---

SEQUENCE LISTING

```
Sequence total quantity: 594
SEQ ID NO: 1            moltype = DNA  length = 381
FEATURE                 Location/Qualifiers
source                  1..381
                        mol_type = other DNA
                        organism = synthetic construct
                        note = synthetic
SEQUENCE: 1
gaggtgcagt tgttggagtc tgggggaggc ttggtacagc ctgggggtc  cctgagactc   60
tcctgtgcag cctctggatt cacctttagc agttatgcca tgacctgggt ccgccaggct  120
ccagggaagg gactggagtg ggtctcagtt attagtggta gtggtagtga aacatactac  180
gcagactccg tgaagggccg gttcaccatc tccagagaca attccaaaaa cacgctgtat  240
ctgcaaatga acagcctgag agccgaagac acggccgtat attactgtgt gaaagattct  300
tcgtatagga gctcgtcgag ggcctactac tactacggaa tggacgtctg gggcctaggg  360
accacggtca ccgtctcctc a                                            381

SEQ ID NO: 2            moltype = AA  length = 127
FEATURE                 Location/Qualifiers
source                  1..127
                        mol_type = protein
                        organism = synthetic construct
                        note = synthetic
SEQUENCE: 2
EVQLLESGGG LVQPGGSLRL SCAASGFTFS SYAMTWVRQA PGKGLEWVSV ISGSGSETYY   60
ADSVKGRFTI SRDNSKNTLY LQMNSLRAED TAVYYCVKDS SYRSSSRAYY YYGMDVWGLG  120
TTVTVSS                                                            127

SEQ ID NO: 3            moltype = DNA  length = 24
FEATURE                 Location/Qualifiers
source                  1..24
                        mol_type = other DNA
                        organism = synthetic construct
                        note = synthetic
SEQUENCE: 3
ggattcacct ttagcagtta tgcc                                          24

SEQ ID NO: 4            moltype = AA  length = 8
FEATURE                 Location/Qualifiers
source                  1..8
                        mol_type = protein
                        organism = synthetic construct
                        note = synthetic
SEQUENCE: 4
GFTFSSYA                                                            8

SEQ ID NO: 5            moltype = DNA  length = 24
```

```
FEATURE                 Location/Qualifiers
source                  1..24
                        mol_type = other DNA
                        organism = synthetic construct
                        note = synthetic
SEQUENCE: 5
attagtggta gtggtagtga aaca                                          24

SEQ ID NO: 6            moltype = AA  length = 8
FEATURE                 Location/Qualifiers
source                  1..8
                        mol_type = protein
                        organism = synthetic construct
                        note = synthetic
SEQUENCE: 6
ISGSGSET                                                            8

SEQ ID NO: 7            moltype = DNA  length = 60
FEATURE                 Location/Qualifiers
source                  1..60
                        mol_type = other DNA
                        organism = synthetic construct
                        note = synthetic
SEQUENCE: 7
gtgaaagatt cttcgtatag gagctcgtcg agggcctact actactacgg aatggacgtc   60

SEQ ID NO: 8            moltype = AA  length = 20
FEATURE                 Location/Qualifiers
source                  1..20
                        mol_type = protein
                        organism = synthetic construct
                        note = synthetic
SEQUENCE: 8
VKDSSYRSSS RAYYYYGMDV                                               20

SEQ ID NO: 9            moltype = DNA  length = 324
FEATURE                 Location/Qualifiers
source                  1..324
                        mol_type = other DNA
                        organism = synthetic construct
                        note = synthetic
SEQUENCE: 9
gacatccaga tgacccagtc tccatcctcc ctgtctgcat ctgtaggaga cagagtcacc   60
atcacttgcc gggcaagtca gagcattagc agctatttaa attggtatca acagaaacca  120
gggaaagccc ctaagctcct gatctatgct gtttccattt tgcaaagtgg ggtcccatca  180
aggttcagtg gcagtggatc tgggacagat ttcactctca ccatcagctc tctgcaacct  240
gaagattttg caacttactc ctgtcaacag acttacagta cccctccgat caccttcggc  300
caagggacac gactggagat taaa                                         324

SEQ ID NO: 10           moltype = AA  length = 108
FEATURE                 Location/Qualifiers
source                  1..108
                        mol_type = protein
                        organism = synthetic construct
                        note = synthetic
SEQUENCE: 10
DIQMTQSPSS LSASVGDRVT ITCRASQSIS SYLNWYQQKP GKAPKLLIYA VSILQSGVPS   60
RFSGSGSGTD FTLTISSLQP EDFATYSCQQ TYSTPPITFG QGTRLEIK               108

SEQ ID NO: 11           moltype = DNA  length = 18
FEATURE                 Location/Qualifiers
source                  1..18
                        mol_type = other DNA
                        organism = synthetic construct
                        note = synthetic
SEQUENCE: 11
cagagcatta gcagctat                                                 18

SEQ ID NO: 12           moltype = AA  length = 6
FEATURE                 Location/Qualifiers
source                  1..6
                        mol_type = protein
                        organism = synthetic construct
                        note = synthetic
SEQUENCE: 12
QSISSY                                                              6

SEQ ID NO: 13           moltype =   length =
SEQUENCE: 13
```

```
000

SEQ ID NO: 14          moltype =    length =
SEQUENCE: 14
000

SEQ ID NO: 15          moltype = DNA   length = 30
FEATURE                Location/Qualifiers
source                 1..30
                       mol_type = other DNA
                       organism = synthetic construct
                       note = synthetic
SEQUENCE: 15
caacagactt acagtacccc tccgatcacc                                     30

SEQ ID NO: 16          moltype = AA   length = 10
FEATURE                Location/Qualifiers
source                 1..10
                       mol_type = protein
                       organism = synthetic construct
                       note = synthetic
SEQUENCE: 16
QQTYSTPPIT                                                           10

SEQ ID NO: 17          moltype = DNA   length = 381
FEATURE                Location/Qualifiers
source                 1..381
                       mol_type = other DNA
                       organism = synthetic construct
                       note = synthetic
SEQUENCE: 17
gaggtgcagc tattggagtc aggggggaggc ttggtacagc cggggggggtc cctgagactc   60
tcctgtgcag cctctggatt cacctttagt ggctatgccg tgagctgggt ccgccaggct  120
ccagggaagg ggctggagtg ggtctcaact attagtggaa gtggtactat cacacattac  180
gtagactccg tgaagggccg gttcaccatc tcccgagaca attccaagaa cacgctgtat  240
ctgcaaatga gcagcctgag agccgaggac acggccatat attactgtgc gagagacccg  300
tattacgatg ttttgactgg ttattataag gaggactact tgactactgg ggccaggga  360
accctggtca ccgtctcctc a                                            381

SEQ ID NO: 18          moltype = AA   length = 127
FEATURE                Location/Qualifiers
source                 1..127
                       mol_type = protein
                       organism = synthetic construct
                       note = synthetic
SEQUENCE: 18
EVQLLESGGG LVQPGGSLRL SCAASGFTFS GYAVSWVRQA PGKGLEWVST ISGSGTITHY   60
VDSVKGRFTI SRDNSKNTLY LQMSSLRAED TAIYYCARDP YYDVLTGYYK EDYFDYWGQG  120
TLVTVSS                                                            127

SEQ ID NO: 19          moltype = DNA   length = 24
FEATURE                Location/Qualifiers
source                 1..24
                       mol_type = other DNA
                       organism = synthetic construct
                       note = synthetic
SEQUENCE: 19
ggattcacct ttagtggcta tgcc                                           24

SEQ ID NO: 20          moltype = AA   length = 8
FEATURE                Location/Qualifiers
source                 1..8
                       mol_type = protein
                       organism = synthetic construct
                       note = synthetic
SEQUENCE: 20
GFTFSGYA                                                              8

SEQ ID NO: 21          moltype = DNA   length = 24
FEATURE                Location/Qualifiers
source                 1..24
                       mol_type = other DNA
                       organism = synthetic construct
                       note = synthetic
SEQUENCE: 21
attagtggaa gtggtactat caca                                           24

SEQ ID NO: 22          moltype = AA   length = 8
FEATURE                Location/Qualifiers
```

```
source                  1..8
                        mol_type = protein
                        organism = synthetic construct
                        note = synthetic
SEQUENCE: 22
ISGSGTIT                                                                    8

SEQ ID NO: 23           moltype = DNA   length = 60
FEATURE                 Location/Qualifiers
source                  1..60
                        mol_type = other DNA
                        organism = synthetic construct
                        note = synthetic
SEQUENCE: 23
gcgagagacc cgtattacga tgtttttgact ggttattata aggaggacta ctttgactac          60

SEQ ID NO: 24           moltype = AA    length = 20
FEATURE                 Location/Qualifiers
source                  1..20
                        mol_type = protein
                        organism = synthetic construct
                        note = synthetic
SEQUENCE: 24
ARDPYYDVLT GYYKEDYFDY                                                      20

SEQ ID NO: 25           moltype = DNA   length = 324
FEATURE                 Location/Qualifiers
source                  1..324
                        mol_type = other DNA
                        organism = synthetic construct
                        note = synthetic
SEQUENCE: 25
gacatccaga tgacccagtc tccatcctcc ctgtctgcat ctgtaggaga cagagtcacc          60
atcacttgcc gggcaagtca gagcattagc aactatttaa attggtatca gcagaaacca        120
gggaaagccc ctaagctcct gatctatgct gcattcagct tgcaaactgg ggtcccatca        180
aggttcagtg gcagtggatc tgggacagat ttcactctca ccatcagcag tctgcaacct        240
gaagattttg caacttacta ctgtcaacag agttacagta cccctccgat caccttcggc        300
caagggacac gactggagat taaa                                                324

SEQ ID NO: 26           moltype = AA    length = 108
FEATURE                 Location/Qualifiers
source                  1..108
                        mol_type = protein
                        organism = synthetic construct
                        note = synthetic
SEQUENCE: 26
DIQMTQSPSS LSASVGDRVT ITCRASQSIS NYLNWYQQKP GKAPKLLIYA AFSLQTGVPS           60
RFSGSGSGTD FTLTISSLQP EDFATYYCQQ SYSTPPITFG QGTRLEIK                       108

SEQ ID NO: 27           moltype = DNA   length = 18
FEATURE                 Location/Qualifiers
source                  1..18
                        mol_type = other DNA
                        organism = synthetic construct
                        note = synthetic
SEQUENCE: 27
cagagcatta gcaactat                                                        18

SEQ ID NO: 28           moltype = AA    length = 6
FEATURE                 Location/Qualifiers
source                  1..6
                        mol_type = protein
                        organism = synthetic construct
                        note = synthetic
SEQUENCE: 28
QSISNY                                                                      6

SEQ ID NO: 29           moltype =       length =
SEQUENCE: 29
000

SEQ ID NO: 30           moltype =       length =
SEQUENCE: 30
000

SEQ ID NO: 31           moltype = DNA   length = 30
FEATURE                 Location/Qualifiers
source                  1..30
                        mol_type = other DNA
```

```
                                organism = synthetic construct
                                note = synthetic
SEQUENCE: 31
caacagagtt acagtacccc tccgatcacc                                           30

SEQ ID NO: 32           moltype = AA   length = 10
FEATURE                 Location/Qualifiers
source                  1..10
                        mol_type = protein
                        organism = synthetic construct
                        note = synthetic
SEQUENCE: 32
QQSYSTPPIT                                                                 10

SEQ ID NO: 33           moltype = DNA   length = 375
FEATURE                 Location/Qualifiers
source                  1..375
                        mol_type = other DNA
                        organism = synthetic construct
                        note = synthetic
SEQUENCE: 33
gaggtgcagc tggtggagtc tgggggagat ttggtccagc ctgggacgtc cctgagactc          60
tcctgtgaag cctctggatt caccttaagt ttctacgcta tgtactgggt ccgccaggct         120
cctgggaagg aactggaact tgtttcaggt attagtggta tgggggaaag catgttttat         180
ggaaactctg tgaagggcag attctccatc tccagagaca attccaagaa cacgctgtat         240
cttcaaatgg gcagtgtgag agctgaggac atggctgtgt attactgtgc gagagcctac         300
gctagtggaa actcctactt cttttactac ggtatggacg tctggggcca agggaccacg         360
gtcaccgtct cctca                                                         375

SEQ ID NO: 34           moltype = AA   length = 125
FEATURE                 Location/Qualifiers
source                  1..125
                        mol_type = protein
                        organism = synthetic construct
                        note = synthetic
SEQUENCE: 34
EVQLVESGGD LVQPGTSLRL SCEASGFTLS FYAMYWVRQA PGKELELVSG ISGNGESMFY          60
GNSVKGRFSI SRDNSKNTLY LQMGSVRAED MAVYYCARAY ASGNSYFFYY GMDVWGQGTT         120
VTVSS                                                                    125

SEQ ID NO: 35           moltype = DNA   length = 24
FEATURE                 Location/Qualifiers
source                  1..24
                        mol_type = other DNA
                        organism = synthetic construct
                        note = synthetic
SEQUENCE: 35
ggattcacct taagtttcta cgct                                                 24

SEQ ID NO: 36           moltype = AA   length = 8
FEATURE                 Location/Qualifiers
source                  1..8
                        mol_type = protein
                        organism = synthetic construct
                        note = synthetic
SEQUENCE: 36
GFTLSFYA                                                                    8

SEQ ID NO: 37           moltype = DNA   length = 24
FEATURE                 Location/Qualifiers
source                  1..24
                        mol_type = other DNA
                        organism = synthetic construct
                        note = synthetic
SEQUENCE: 37
attagtggta tggggaaag catg                                                  24

SEQ ID NO: 38           moltype = AA   length = 8
FEATURE                 Location/Qualifiers
source                  1..8
                        mol_type = protein
                        organism = synthetic construct
                        note = synthetic
SEQUENCE: 38
ISGNGESM                                                                    8

SEQ ID NO: 39           moltype = DNA   length = 54
FEATURE                 Location/Qualifiers
source                  1..54
```

```
                        mol_type = other DNA
                        organism = synthetic construct
                        note = synthetic
SEQUENCE: 39
gcgagagcct acgctagtgg aaactcctac ttcttttact acggtatgga cgtc         54

SEQ ID NO: 40           moltype = AA  length = 18
FEATURE                 Location/Qualifiers
source                  1..18
                        mol_type = protein
                        organism = synthetic construct
                        note = synthetic
SEQUENCE: 40
ARAYASGNSY FFYYGMDV                                                 18

SEQ ID NO: 41           moltype = DNA  length = 324
FEATURE                 Location/Qualifiers
source                  1..324
                        mol_type = other DNA
                        organism = synthetic construct
                        note = synthetic
SEQUENCE: 41
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccaatt tgcaaagtgg ggtcccatca  180
aggttcagtg gcagtggatc tgggacagat ttcactctca ccatcagcag tctgcaacct  240
gaagattttg caacttacta ctgtcaacag agttacagtg gccccccgat cacccttcggc  300
caagggacac gactggagat taaa                                         324

SEQ ID NO: 42           moltype = AA  length = 108
FEATURE                 Location/Qualifiers
source                  1..108
                        mol_type = protein
                        organism = synthetic construct
                        note = synthetic
SEQUENCE: 42
DIQMTQSPSS LSASVGDRVT ITCRASQSIS SYLNWYQQKP GKAPKLLIYA ASNLQSGVPS   60
RFSGSGSGTD FTLTISSLQP EDFATYYCQQ SYSGPPITFG QGTRLEIK               108

SEQ ID NO: 43           moltype = DNA  length = 18
FEATURE                 Location/Qualifiers
source                  1..18
                        mol_type = other DNA
                        organism = synthetic construct
                        note = synthetic
SEQUENCE: 43
cagagcatta gcagctat                                                 18

SEQ ID NO: 44           moltype = AA  length = 6
FEATURE                 Location/Qualifiers
source                  1..6
                        mol_type = protein
                        organism = synthetic construct
                        note = synthetic
SEQUENCE: 44
QSISSY                                                              6

SEQ ID NO: 45           moltype =  length =
SEQUENCE: 45
000

SEQ ID NO: 46           moltype =  length =
SEQUENCE: 46
000

SEQ ID NO: 47           moltype = DNA  length = 30
FEATURE                 Location/Qualifiers
source                  1..30
                        mol_type = other DNA
                        organism = synthetic construct
                        note = synthetic
SEQUENCE: 47
caacagagtt acagtggccc cccgatcacc                                    30

SEQ ID NO: 48           moltype = AA  length = 10
FEATURE                 Location/Qualifiers
source                  1..10
                        mol_type = protein
                        organism = synthetic construct
```

```
                            note = synthetic
SEQUENCE: 48
QQSYSGPPIT                                                                      10

SEQ ID NO: 49           moltype = DNA  length = 375
FEATURE                 Location/Qualifiers
source                  1..375
                        mol_type = other DNA
                        organism = synthetic construct
                        note = synthetic
SEQUENCE: 49
gaggtgcagc tggtggagtc tgggggaggc ttggtccagc ctggggcgtc cctgagactc              60
tcctgtgaag cctctggatt caccttaagt ttctattcta tgcactgggt ccgccaggct             120
ccagggaggg aattggaata tgtttcaggt attagtggta atggaaataa catatattat             180
agagactctg taaagggcag attcaccatt tctagagaca attccaagaa cacgctgaat             240
cttcaaatgg gcagtgtgag agctgaggat atgggtgttt attactgtgc gagatcctac             300
tctagtggga attcctacaa ctactactac ggaatggacg tctggggcca agggaccacg             360
gtcaccgtct cctca                                                              375

SEQ ID NO: 50           moltype = AA  length = 125
FEATURE                 Location/Qualifiers
source                  1..125
                        mol_type = protein
                        organism = synthetic construct
                        note = synthetic
SEQUENCE: 50
EVQLVESGGG LVQPGASLRL SCEASGFTLS FYSMHWVRQA PGRELEYVSG ISGNGNNIYY              60
RDSVKGRFTI SRDNSKNTLN LQMGSVRAED MGVYYCARSY SSGNSYNYYY GMDVWGQGTT             120
VTVSS                                                                         125

SEQ ID NO: 51           moltype = DNA  length = 24
FEATURE                 Location/Qualifiers
source                  1..24
                        mol_type = other DNA
                        organism = synthetic construct
                        note = synthetic
SEQUENCE: 51
ggattcacct taagtttcta ttct                                                     24

SEQ ID NO: 52           moltype = AA  length = 8
FEATURE                 Location/Qualifiers
source                  1..8
                        mol_type = protein
                        organism = synthetic construct
                        note = synthetic
SEQUENCE: 52
GFTLSFYS                                                                        8

SEQ ID NO: 53           moltype = DNA  length = 24
FEATURE                 Location/Qualifiers
source                  1..24
                        mol_type = other DNA
                        organism = synthetic construct
                        note = synthetic
SEQUENCE: 53
attagtggta atggaaataa cata                                                     24

SEQ ID NO: 54           moltype = AA  length = 8
FEATURE                 Location/Qualifiers
source                  1..8
                        mol_type = protein
                        organism = synthetic construct
                        note = synthetic
SEQUENCE: 54
ISGNGNNI                                                                        8

SEQ ID NO: 55           moltype = DNA  length = 54
FEATURE                 Location/Qualifiers
source                  1..54
                        mol_type = other DNA
                        organism = synthetic construct
                        note = synthetic
SEQUENCE: 55
gcgagatcct actctagtgg gaattcctac aactactact acggaatgga cgtc                    54

SEQ ID NO: 56           moltype = AA  length = 18
FEATURE                 Location/Qualifiers
source                  1..18
                        mol_type = protein
```

```
                        organism = synthetic construct
                        note = synthetic
SEQUENCE: 56
ARSYSSGNSY NYYYGMDV                                                 18

SEQ ID NO: 57           moltype = DNA   length = 324
FEATURE                 Location/Qualifiers
source                  1..324
                        mol_type = other DNA
                        organism = synthetic construct
                        note = synthetic
SEQUENCE: 57
gacatccaga tgacccagtc tccatcctcc ctgtctgcat ctgttggaga cagagtcacc    60
atcacttgcc gggcaagtca gaccattagt agctatttaa attggtatca gcagaaacca   120
gggaaagccc ctaagctcct catctatgct gtatccaatt tacaaagtgg ggtcccatca   180
aggttcagtg gcagtggatc tgggacagat ttcactctca ccatcagcag tctgcaacct   240
gaagattttg caacttacta ctgtcaacag agttacagta ccccctccgat caccttcggc  300
caagggacac gactggagat taaa                                          324

SEQ ID NO: 58           moltype = AA    length = 108
FEATURE                 Location/Qualifiers
source                  1..108
                        mol_type = protein
                        organism = synthetic construct
                        note = synthetic
SEQUENCE: 58
DIQMTQSPSS LSASVGDRVT ITCRASQTIS SYLNWYQQKP GKAPKLLIYA VSNLQSGVPS    60
RFSGSGSGTD FTLTISSLQP EDFATYYCQQ SYSTPPITFG QGTRLEIK               108

SEQ ID NO: 59           moltype = DNA   length = 18
FEATURE                 Location/Qualifiers
source                  1..18
                        mol_type = other DNA
                        organism = synthetic construct
                        note = synthetic
SEQUENCE: 59
cagaccatta gtagctat                                                 18

SEQ ID NO: 60           moltype = AA    length = 6
FEATURE                 Location/Qualifiers
source                  1..6
                        mol_type = protein
                        organism = synthetic construct
                        note = synthetic
SEQUENCE: 60
QTISSY                                                              6

SEQ ID NO: 61           moltype =       length =
SEQUENCE: 61
000

SEQ ID NO: 62           moltype =       length =
SEQUENCE: 62
000

SEQ ID NO: 63           moltype = DNA   length = 30
FEATURE                 Location/Qualifiers
source                  1..30
                        mol_type = other DNA
                        organism = synthetic construct
                        note = synthetic
SEQUENCE: 63
caacagagtt acagtaccccc tccgatcacc                                   30

SEQ ID NO: 64           moltype = AA    length = 10
FEATURE                 Location/Qualifiers
source                  1..10
                        mol_type = protein
                        organism = synthetic construct
                        note = synthetic
SEQUENCE: 64
QQSYSTPPIT                                                          10

SEQ ID NO: 65           moltype = DNA   length = 381
FEATURE                 Location/Qualifiers
source                  1..381
                        mol_type = other DNA
                        organism = synthetic construct
                        note = synthetic
```

```
SEQUENCE: 65
gaggtgcagc tggtggagtc tggggggaggc ttagaacaac cggggggggtc cctgagactc   60
tcctgtgcag cctctggatt cacctttagc agttatgcca tgacctgggt ccgccaggct  120
ccagggaggg ggctggagtg ggtctcagtt attagtggtc gtggtgatac tacatactac  180
gcagactccg tgaagggccg gttcactatc tccagagaca attccaaaaa cacgctatat  240
ctgcaaatga acagcctgag agccgaggac acggccgtat attactgtgc gaaagacagt  300
aattatgtta catctcttgg gaattactac tactacggta tagacgtctg gggccaaggg  360
accacggtca ccgtctcctc a                                             381

SEQ ID NO: 66            moltype = AA   length = 127
FEATURE                  Location/Qualifiers
source                   1..127
                         mol_type = protein
                         organism = synthetic construct
                         note = synthetic
SEQUENCE: 66
EVQLVESGGG LEQPGGSLRL SCAASGFTFS SYAMTWVRQA PGRGLEWVSV ISGRGDTTYY   60
ADSVKGRFTI SRDNSKNTLY LQMNSLRAED TAVYYCAKDS NYVTSLGNYY YYGIDVWGQG  120
TTVTVSS                                                            127

SEQ ID NO: 67            moltype = DNA   length = 24
FEATURE                  Location/Qualifiers
source                   1..24
                         mol_type = other DNA
                         organism = synthetic construct
                         note = synthetic
SEQUENCE: 67
ggattcacct ttagcagtta tgcc                                          24

SEQ ID NO: 68            moltype = AA   length = 8
FEATURE                  Location/Qualifiers
source                   1..8
                         mol_type = protein
                         organism = synthetic construct
                         note = synthetic
SEQUENCE: 68
GFTFSSYA                                                             8

SEQ ID NO: 69            moltype = DNA   length = 24
FEATURE                  Location/Qualifiers
source                   1..24
                         mol_type = other DNA
                         organism = synthetic construct
                         note = synthetic
SEQUENCE: 69
attagtggtc gtggtgatac taca                                          24

SEQ ID NO: 70            moltype = AA   length = 8
FEATURE                  Location/Qualifiers
source                   1..8
                         mol_type = protein
                         organism = synthetic construct
                         note = synthetic
SEQUENCE: 70
ISGRGDTT                                                             8

SEQ ID NO: 71            moltype = DNA   length = 60
FEATURE                  Location/Qualifiers
source                   1..60
                         mol_type = other DNA
                         organism = synthetic construct
                         note = synthetic
SEQUENCE: 71
gcgaaagaca gtaattatgt tacatctctt gggaattact actactacgg tatagacgtc   60

SEQ ID NO: 72            moltype = AA   length = 20
FEATURE                  Location/Qualifiers
source                   1..20
                         mol_type = protein
                         organism = synthetic construct
                         note = synthetic
SEQUENCE: 72
AKDSNYVTSL GNYYYYGIDV                                               20

SEQ ID NO: 73            moltype = DNA   length = 324
FEATURE                  Location/Qualifiers
source                   1..324
                         mol_type = other DNA
                         organism = synthetic construct
```

```
                            note = synthetic
SEQUENCE: 73
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

SEQ ID NO: 74              moltype = AA  length = 108
FEATURE                    Location/Qualifiers
source                     1..108
                           mol_type = protein
                           organism = synthetic construct
                           note = synthetic
SEQUENCE: 74
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK               108

SEQ ID NO: 75              moltype = DNA  length = 18
FEATURE                    Location/Qualifiers
source                     1..18
                           mol_type = other DNA
                           organism = synthetic construct
                           note = synthetic
SEQUENCE: 75
cagagcatta gcagctat                                                  18

SEQ ID NO: 76              moltype = AA  length = 6
FEATURE                    Location/Qualifiers
source                     1..6
                           mol_type = protein
                           organism = synthetic construct
                           note = synthetic
SEQUENCE: 76
QSISSY                                                                6

SEQ ID NO: 77              moltype =   length =
SEQUENCE: 77
000

SEQ ID NO: 78              moltype =   length =
SEQUENCE: 78
000

SEQ ID NO: 79              moltype = DNA  length = 30
FEATURE                    Location/Qualifiers
source                     1..30
                           mol_type = other DNA
                           organism = synthetic construct
                           note = synthetic
SEQUENCE: 79
caacagagtt acagtacccc tccgatcacc                                     30

SEQ ID NO: 80              moltype = AA  length = 10
FEATURE                    Location/Qualifiers
source                     1..10
                           mol_type = protein
                           organism = synthetic construct
                           note = synthetic
SEQUENCE: 80
QQSYSTPPIT                                                           10

SEQ ID NO: 81              moltype = DNA  length = 375
FEATURE                    Location/Qualifiers
source                     1..375
                           mol_type = other DNA
                           organism = synthetic construct
                           note = synthetic
SEQUENCE: 81
gaggtgcagc tggtggagtc tgggggaggc ttggtccagc ctggggcgtc cctgagactc    60
tcctgtgaag cctctggatt caccttaagt ttctatgcta tgcactgggt ccgccaggct   120
ccagggaagg aactggaata tgtttcaggt attagtggta tgggaatagc atatattat   180
agagactctg taaagggcag attcaccatt tctagagaca attccaagaa cacgctgtat   240
cttcaaatgg gcagtgtggg agctgaggat atggctgtgt attactgtgc agatcctac   300
tctagtggga actcctacta ctactactac ggaatggacg tctggggcca agggaccacg   360
gtcaccgtct cctca                                                   375

SEQ ID NO: 82              moltype = AA  length = 125
```

| | |
|---|---|
| FEATURE | Location/Qualifiers |
| source | 1..125 |
| | mol_type = protein |
| | organism = synthetic construct |
| | note = synthetic |

SEQUENCE: 82
```
EVQLVESGGG LVQPGASLRL SCEASGFTLS FYAMHWVRQA PGKELEYVSG ISGNGNSIYY    60
RDSVKGRFTI SRDNSKNTLY LQMGSVGAED MAVYYCARSY SSGNSYYYYY GMDVWGQGTT   120
VTVSS                                                              125
```

| | |
|---|---|
| SEQ ID NO: 83 | moltype = DNA  length = 24 |
| FEATURE | Location/Qualifiers |
| source | 1..24 |
| | mol_type = other DNA |
| | organism = synthetic construct |
| | note = synthetic |

SEQUENCE: 83
```
ggattcacct taagtttcta tgct                                          24
```

| | |
|---|---|
| SEQ ID NO: 84 | moltype = AA  length = 8 |
| FEATURE | Location/Qualifiers |
| source | 1..8 |
| | mol_type = protein |
| | organism = synthetic construct |
| | note = synthetic |

SEQUENCE: 84
```
GFTLSFYA                                                             8
```

| | |
|---|---|
| SEQ ID NO: 85 | moltype = DNA  length = 24 |
| FEATURE | Location/Qualifiers |
| source | 1..24 |
| | mol_type = other DNA |
| | organism = synthetic construct |
| | note = synthetic |

SEQUENCE: 85
```
attagtggta atgggaatag cata                                          24
```

| | |
|---|---|
| SEQ ID NO: 86 | moltype = AA  length = 8 |
| FEATURE | Location/Qualifiers |
| source | 1..8 |
| | mol_type = protein |
| | organism = synthetic construct |
| | note = synthetic |

SEQUENCE: 86
```
ISGNGNSI                                                             8
```

| | |
|---|---|
| SEQ ID NO: 87 | moltype = DNA  length = 54 |
| FEATURE | Location/Qualifiers |
| source | 1..54 |
| | mol_type = other DNA |
| | organism = synthetic construct |
| | note = synthetic |

SEQUENCE: 87
```
gcgagatcct actctagtgg gaactcctac tactactact acggaatgga cgtc          54
```

| | |
|---|---|
| SEQ ID NO: 88 | moltype = AA  length = 18 |
| FEATURE | Location/Qualifiers |
| source | 1..18 |
| | mol_type = protein |
| | organism = synthetic construct |
| | note = synthetic |

SEQUENCE: 88
```
ARSYSSGNSY YYYYGMDV                                                 18
```

| | |
|---|---|
| SEQ ID NO: 89 | moltype = DNA  length = 324 |
| FEATURE | Location/Qualifiers |
| source | 1..324 |
| | mol_type = other DNA |
| | organism = synthetic construct |
| | note = synthetic |

SEQUENCE: 89
```
gacatccaga tgacccagtc tccatcctcc ctgtctgcat ctgtaggaga cagaattacc    60
atcacttgcc gggcaagtca gagcattagc agctatttaa attggtatca gcagaaacca   120
gggaaagccc ctaacctcct gatctatgct gcatccaatt tacaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

| | |
|---|---|
| SEQ ID NO: 90 | moltype = AA  length = 108 |

```
FEATURE              Location/Qualifiers
source               1..108
                     mol_type = protein
                     organism = synthetic construct
                     note = synthetic
SEQUENCE: 90
DIQMTQSPSS LSASVGDRIT ITCRASQSIS SYLNWYQQKP GKAPNLLIYA ASNLQSGVPS    60
RFSGSGSGTD FTLTISSLQP EDFATYYCQQ SYSTPPITFG QGTRLEIK                108

SEQ ID NO: 91        moltype = DNA  length = 18
FEATURE              Location/Qualifiers
source               1..18
                     mol_type = other DNA
                     organism = synthetic construct
                     note = synthetic
SEQUENCE: 91
cagagcatta gcagctat                                                  18

SEQ ID NO: 92        moltype = AA  length = 6
FEATURE              Location/Qualifiers
source               1..6
                     mol_type = protein
                     organism = synthetic construct
                     note = synthetic
SEQUENCE: 92
QSISSY                                                                6

SEQ ID NO: 93        moltype =    length =
SEQUENCE: 93
000

SEQ ID NO: 94        moltype =    length =
SEQUENCE: 94
000

SEQ ID NO: 95        moltype = DNA  length = 30
FEATURE              Location/Qualifiers
source               1..30
                     mol_type = other DNA
                     organism = synthetic construct
                     note = synthetic
SEQUENCE: 95
caacagagtt acagtacccc tccgatcacc                                     30

SEQ ID NO: 96        moltype = AA  length = 10
FEATURE              Location/Qualifiers
source               1..10
                     mol_type = protein
                     organism = synthetic construct
                     note = synthetic
SEQUENCE: 96
QQSYSTPPIT                                                           10

SEQ ID NO: 97        moltype = DNA  length = 378
FEATURE              Location/Qualifiers
source               1..378
                     mol_type = other DNA
                     organism = synthetic construct
                     note = synthetic
SEQUENCE: 97
gaggtgcagc tggtggagtc tgggggaggc ttggtacagc ctgggggtc  cctgagactc    60
tcctgtgcag cctctggatt caccttttagc agctatgcca tgagctgggt ccgccaggct  120
ccagggaggg gactggagtg ggtctcagtt attagtggca gtgatggtaa cacaaactac  180
gcagactccg tgaagggccg gttcaccatc tccagagaca attccaagaa cacactgttt  240
ctgcaaatga acagcctgag agccgaggac acggccgtat attactgtgc aaaagatgcc  300
cgctacggtg gtaactccca ctactactac tacggtatag acgtctgggg ccaagggacc  360
acggtcaccg tctcctca                                                 378

SEQ ID NO: 98        moltype = AA  length = 126
FEATURE              Location/Qualifiers
source               1..126
                     mol_type = protein
                     organism = synthetic construct
                     note = synthetic
SEQUENCE: 98
EVQLVESGGG LVQPGGSLRL SCAASGFTFS SYAMSWVRQA PGRGLEWVSV ISGSDGNTNY    60
ADSVKGRFTI SRDNSKNTLF LQMNSLRAED TAVYYCAKDA RYGGNSHYYY YGIDVWGQGT   120
TVTVSS                                                              126
```

```
SEQ ID NO: 99              moltype = DNA  length = 24
FEATURE                    Location/Qualifiers
source                     1..24
                           mol_type = other DNA
                           organism = synthetic construct
                           note = synthetic
SEQUENCE: 99
ggattcacct ttagcagcta tgcc                                           24

SEQ ID NO: 100             moltype = AA   length = 8
FEATURE                    Location/Qualifiers
source                     1..8
                           mol_type = protein
                           organism = synthetic construct
                           note = synthetic
SEQUENCE: 100
GFTFSSYA                                                              8

SEQ ID NO: 101             moltype = DNA  length = 24
FEATURE                    Location/Qualifiers
source                     1..24
                           mol_type = other DNA
                           organism = synthetic construct
                           note = synthetic
SEQUENCE: 101
attagtggca gtgatggtaa caca                                           24

SEQ ID NO: 102             moltype = AA   length = 8
FEATURE                    Location/Qualifiers
source                     1..8
                           mol_type = protein
                           organism = synthetic construct
                           note = synthetic
SEQUENCE: 102
ISGSDGNT                                                              8

SEQ ID NO: 103             moltype = DNA  length = 57
FEATURE                    Location/Qualifiers
source                     1..57
                           mol_type = other DNA
                           organism = synthetic construct
                           note = synthetic
SEQUENCE: 103
gcgaaagatg cccgctacgg tggtaactcc cactactact actacggtat agacgtc       57

SEQ ID NO: 104             moltype = AA   length = 19
FEATURE                    Location/Qualifiers
source                     1..19
                           mol_type = protein
                           organism = synthetic construct
                           note = synthetic
SEQUENCE: 104
AKDARYGGNS HYYYYGIDV                                                 19

SEQ ID NO: 105             moltype = DNA  length = 324
FEATURE                    Location/Qualifiers
source                     1..324
                           mol_type = other DNA
                           organism = synthetic construct
                           note = synthetic
SEQUENCE: 105
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagcacct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat cacccttcggc  300
caagggacac gactggagat taaa                                          324

SEQ ID NO: 106             moltype = AA   length = 108
FEATURE                    Location/Qualifiers
source                     1..108
                           mol_type = protein
                           organism = synthetic construct
                           note = synthetic
SEQUENCE: 106
DIQMTQSPSS LSASVGDRVT ITCRASQSIS SYLNWYQQKP GKAPKHLIYA ASSLQSGVPS    60
RFSGSGSGTD FTLTISSLQP EDFATYYCQQ SYSTPPITFG QGTRLEIK                108

SEQ ID NO: 107             moltype = DNA  length = 18
```

| FEATURE | Location/Qualifiers |
|---|---|
| source | 1..18<br>mol_type = other DNA<br>organism = synthetic construct<br>note = synthetic |

SEQUENCE: 107
cagagcatta gcagctat                                                        18

| SEQ ID NO: 108 | moltype = AA  length = 6 |
|---|---|
| FEATURE | Location/Qualifiers |
| source | 1..6<br>mol_type = protein<br>organism = synthetic construct<br>note = synthetic |

SEQUENCE: 108
QSISSY                                                                      6

| SEQ ID NO: 109 | moltype =   length = |
|---|---|

SEQUENCE: 109
000

| SEQ ID NO: 110 | moltype =   length = |
|---|---|

SEQUENCE: 110
000

| SEQ ID NO: 111 | moltype = DNA  length = 30 |
|---|---|
| FEATURE | Location/Qualifiers |
| source | 1..30<br>mol_type = other DNA<br>organism = synthetic construct<br>note = synthetic |

SEQUENCE: 111
caacagagtt acagtacccc tccgatcacc                                           30

| SEQ ID NO: 112 | moltype = AA  length = 10 |
|---|---|
| FEATURE | Location/Qualifiers |
| source | 1..10<br>mol_type = protein<br>organism = synthetic construct<br>note = synthetic |

SEQUENCE: 112
QQSYSTPPIT                                                                 10

| SEQ ID NO: 113 | moltype = DNA  length = 360 |
|---|---|
| FEATURE | Location/Qualifiers |
| source | 1..360<br>mol_type = other DNA<br>organism = synthetic construct<br>note = synthetic |

SEQUENCE: 113
caggtgcagc tggtggagtc tgggggaggc ttggtcaagc ctggagggtc cctgagactc      60
tcctgtgcag cctctggatt caccctcagt gactactaca tgagctggat ccgccaggct      120
ccagggaagg ggctggagtg ggtttcatac attagtagta gtggtattac catatactac      180
gcagactctg tgaagggccg attcaccatc tccagggaca cgccaagaa ctcactgtat       240
ctgcaaatga acagcctgag agccgaggac acggccgtgt attactgtgc gagagatagg     300
tatagtagca gctggtactt tgactactgg ggccagggaa ccctggtcac cgtctcctca    360

| SEQ ID NO: 114 | moltype = AA  length = 120 |
|---|---|
| FEATURE | Location/Qualifiers |
| source | 1..120<br>mol_type = protein<br>organism = synthetic construct<br>note = synthetic |

SEQUENCE: 114
QVQLVESGGG LVKPGGSLRL SCAASGFTLS DYYMSWIRQA PGKGLEWVSY ISSSGITIYY      60
ADSVKGRFTI SRDNAKNSLY LQMNSLRAED TAVYYCARDR YSSSWYFDYW GQGTLVTVSS    120

| SEQ ID NO: 115 | moltype = DNA  length = 24 |
|---|---|
| FEATURE | Location/Qualifiers |
| source | 1..24<br>mol_type = other DNA<br>organism = synthetic construct<br>note = synthetic |

SEQUENCE: 115
ggattcaccc tcagtgacta ctac                                                 24

| SEQ ID NO: 116 | moltype = AA  length = 8 |
|---|---|
| FEATURE | Location/Qualifiers |
| source | 1..8 |

-continued

```
                            mol_type = protein
                            organism = synthetic construct
                            note = synthetic
SEQUENCE: 116
GFTLSDYY                                                                  8

SEQ ID NO: 117              moltype = DNA   length = 24
FEATURE                     Location/Qualifiers
source                      1..24
                            mol_type = other DNA
                            organism = synthetic construct
                            note = synthetic
SEQUENCE: 117
attagtagta gtggtattac cata                                               24

SEQ ID NO: 118              moltype = AA   length = 8
FEATURE                     Location/Qualifiers
source                      1..8
                            mol_type = protein
                            organism = synthetic construct
                            note = synthetic
SEQUENCE: 118
ISSSGITI                                                                  8

SEQ ID NO: 119              moltype = DNA   length = 39
FEATURE                     Location/Qualifiers
source                      1..39
                            mol_type = other DNA
                            organism = synthetic construct
                            note = synthetic
SEQUENCE: 119
gcgagagata ggtatagtag cagctggtac tttgactac                               39

SEQ ID NO: 120              moltype = AA   length = 13
FEATURE                     Location/Qualifiers
source                      1..13
                            mol_type = protein
                            organism = synthetic construct
                            note = synthetic
SEQUENCE: 120
ARDRYSSSWY FDY                                                           13

SEQ ID NO: 121              moltype = DNA   length = 321
FEATURE                     Location/Qualifiers
source                      1..321
                            mol_type = other DNA
                            organism = synthetic construct
                            note = synthetic
SEQUENCE: 121
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta ccccgtacac ttttggccag      300
gggaccaagc tggagatcaa a                                                 321

SEQ ID NO: 122              moltype = AA   length = 107
FEATURE                     Location/Qualifiers
source                      1..107
                            mol_type = protein
                            organism = synthetic construct
                            note = synthetic
SEQUENCE: 122
DIQMTQSPSS LSASVGDRVT ITCRASQSIS SYLNWYQQKP GKAPKLLIYA ASSLQSGVPS        60
RFSGSGSGTD FTLTISSLQP EDFATYYCQQ SYSTPYTFGQ GTKLEIK                     107

SEQ ID NO: 123              moltype = DNA   length = 18
FEATURE                     Location/Qualifiers
source                      1..18
                            mol_type = other DNA
                            organism = synthetic construct
                            note = synthetic
SEQUENCE: 123
cagagcatta gcagctat                                                      18

SEQ ID NO: 124              moltype = AA   length = 6
FEATURE                     Location/Qualifiers
source                      1..6
                            mol_type = protein
```

```
                    organism = synthetic construct
                    note = synthetic
SEQUENCE: 124
QSISSY                                                                          6

SEQ ID NO: 125      moltype =   length =
SEQUENCE: 125
000

SEQ ID NO: 126      moltype =   length =
SEQUENCE: 126
000

SEQ ID NO: 127      moltype = DNA   length = 27
FEATURE             Location/Qualifiers
source              1..27
                    mol_type = other DNA
                    organism = synthetic construct
                    note = synthetic
SEQUENCE: 127
caacagagtt acagtacccc gtacact                                                  27

SEQ ID NO: 128      moltype = AA   length = 9
FEATURE             Location/Qualifiers
source              1..9
                    mol_type = protein
                    organism = synthetic construct
                    note = synthetic
SEQUENCE: 128
QQSYSTPYT                                                                       9

SEQ ID NO: 129      moltype = DNA   length = 357
FEATURE             Location/Qualifiers
source              1..357
                    mol_type = other DNA
                    organism = synthetic construct
                    note = synthetic
SEQUENCE: 129
gaggtgcagc tggtggagtc tggggggaggc ttggtacagc cggggggggtc cctgagactc            60
tcctgtgcag cctctggatt cacttttagc agttatggta tgacctgggt ccgccaggct            120
ccagggaagg ggctggagtg ggtctcagct attagtgtta gtggtggtac cacatactac            180
gcagactccg tgaagggccg gttcaccatc tccagagaca attccaagaa aatgctgaat            240
ctgcaaatga acagcctgag agccgaggac acggccatat attactgtgc gaaagatgag            300
ggctggaacg actactttga ctactggggc cagggaaccc tggtcaccgt ctcctca              357

SEQ ID NO: 130      moltype = AA   length = 119
FEATURE             Location/Qualifiers
source              1..119
                    mol_type = protein
                    organism = synthetic construct
                    note = synthetic
SEQUENCE: 130
EVQLVESGGG LVQPGGSLRL SCAASGFTFS SYGMTWVRQA PGKGLEWVSA ISVSGGTTYY             60
ADSVKGRFTI SRDNSKKMLN LQMNSLRAED TAIYYCAKDE GWNDYFDYWG QGTLVTVSS             119

SEQ ID NO: 131      moltype = DNA   length = 24
FEATURE             Location/Qualifiers
source              1..24
                    mol_type = other DNA
                    organism = synthetic construct
                    note = synthetic
SEQUENCE: 131
ggattcactt ttagcagtta tggt                                                     24

SEQ ID NO: 132      moltype = AA   length = 8
FEATURE             Location/Qualifiers
source              1..8
                    mol_type = protein
                    organism = synthetic construct
                    note = synthetic
SEQUENCE: 132
GFTFSSYG                                                                        8

SEQ ID NO: 133      moltype = DNA   length = 24
FEATURE             Location/Qualifiers
source              1..24
                    mol_type = other DNA
                    organism = synthetic construct
                    note = synthetic
```

-continued

```
SEQUENCE: 133
attagtgtta gtggtggtac caca                                          24

SEQ ID NO: 134          moltype = AA  length = 8
FEATURE                 Location/Qualifiers
source                  1..8
                        mol_type = protein
                        organism = synthetic construct
                        note = synthetic
SEQUENCE: 134
ISVSGGTT                                                             8

SEQ ID NO: 135          moltype = DNA  length = 36
FEATURE                 Location/Qualifiers
source                  1..36
                        mol_type = other DNA
                        organism = synthetic construct
                        note = synthetic
SEQUENCE: 135
gcgaaagatg agggctggaa cgactacttt gactac                             36

SEQ ID NO: 136          moltype = AA  length = 12
FEATURE                 Location/Qualifiers
source                  1..12
                        mol_type = protein
                        organism = synthetic construct
                        note = synthetic
SEQUENCE: 136
AKDEGWNDYF DY                                                       12

SEQ ID NO: 137          moltype = DNA  length = 324
FEATURE                 Location/Qualifiers
source                  1..324
                        mol_type = other DNA
                        organism = synthetic construct
                        note = synthetic
SEQUENCE: 137
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 138          moltype = AA  length = 108
FEATURE                 Location/Qualifiers
source                  1..108
                        mol_type = protein
                        organism = synthetic construct
                        note = synthetic
SEQUENCE: 138
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPPITFG QGTRLEIK               108

SEQ ID NO: 139          moltype = DNA  length = 18
FEATURE                 Location/Qualifiers
source                  1..18
                        mol_type = other DNA
                        organism = synthetic construct
                        note = synthetic
SEQUENCE: 139
cagagcatta gcagctat                                                 18

SEQ ID NO: 140          moltype = AA  length = 6
FEATURE                 Location/Qualifiers
source                  1..6
                        mol_type = protein
                        organism = synthetic construct
                        note = synthetic
SEQUENCE: 140
QSISSY                                                               6

SEQ ID NO: 141          moltype =    length =
SEQUENCE: 141
000

SEQ ID NO: 142          moltype =    length =
SEQUENCE: 142
000
```

```
SEQ ID NO: 143          moltype = DNA  length = 30
FEATURE                 Location/Qualifiers
source                  1..30
                        mol_type = other DNA
                        organism = synthetic construct
                        note = synthetic
SEQUENCE: 143
caacagagtt acagtacccc tccgatcacc                                     30

SEQ ID NO: 144          moltype = AA  length = 10
FEATURE                 Location/Qualifiers
source                  1..10
                        mol_type = protein
                        organism = synthetic construct
                        note = synthetic
SEQUENCE: 144
QQSYSTPPIT                                                           10

SEQ ID NO: 145          moltype = DNA  length = 378
FEATURE                 Location/Qualifiers
source                  1..378
                        mol_type = other DNA
                        organism = synthetic construct
                        note = synthetic
SEQUENCE: 145
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacat actacaggtc caagtggtat   180
attgattatg cactatctgt gaaaagtcga ataaccatca acccagacac atccaagaac   240
cagttctccc tgcagctgaa ctctgtgact cccgaggaca cggctgtgta ttactgtgca   300
ggaggtatag agtattactg gaactacctt gatgcttttg atatctgggg ccaagggaca   360
atggtcaccg tctcttca                                                 378

SEQ ID NO: 146          moltype = AA  length = 126
FEATURE                 Location/Qualifiers
source                  1..126
                        mol_type = protein
                        organism = synthetic construct
                        note = synthetic
SEQUENCE: 146
QVQLQQSGPG LVKPSQTLSL TCAISGDSVS SNSAAWNWIR QSPSRGLEWL GRTYYRSKWY    60
IDYALSVKSR ITINPDTSKN QFSLQLNSVT PEDTAVYYCA GGIEYYWNYL DAFDIWGQGT   120
MVTVSS                                                              126

SEQ ID NO: 147          moltype = DNA  length = 30
FEATURE                 Location/Qualifiers
source                  1..30
                        mol_type = other DNA
                        organism = synthetic construct
                        note = synthetic
SEQUENCE: 147
ggggacagtg tctctagcaa cagtgctgct                                     30

SEQ ID NO: 148          moltype = AA  length = 10
FEATURE                 Location/Qualifiers
source                  1..10
                        mol_type = protein
                        organism = synthetic construct
                        note = synthetic
SEQUENCE: 148
GDSVSSNSAA                                                           10

SEQ ID NO: 149          moltype = DNA  length = 27
FEATURE                 Location/Qualifiers
source                  1..27
                        mol_type = other DNA
                        organism = synthetic construct
                        note = synthetic
SEQUENCE: 149
acatactaca ggtccaagtg gtatatt                                        27

SEQ ID NO: 150          moltype = AA  length = 9
FEATURE                 Location/Qualifiers
source                  1..9
                        mol_type = protein
                        organism = synthetic construct
                        note = synthetic
SEQUENCE: 150
```

```
TYYRSKWYI                                                                   9

SEQ ID NO: 151          moltype = DNA  length = 48
FEATURE                 Location/Qualifiers
source                  1..48
                        mol_type = other DNA
                        organism = synthetic construct
                        note = synthetic
SEQUENCE: 151
gcaggaggta tagagtatta ctggaactac cttgatgctt ttgatatc                       48

SEQ ID NO: 152          moltype = AA   length = 16
FEATURE                 Location/Qualifiers
source                  1..16
                        mol_type = protein
                        organism = synthetic construct
                        note = synthetic
SEQUENCE: 152
AGGIEYYWNY LDAFDI                                                          16

SEQ ID NO: 153          moltype = DNA  length = 321
FEATURE                 Location/Qualifiers
source                  1..321
                        mol_type = other DNA
                        organism = synthetic construct
                        note = synthetic
SEQUENCE: 153
gacatccaga tgacccagtc tccatcctcc ctgtctgcat ctgtaggaga cagagtcacc          60
atcacttgcc gggcaagtca gagcattagc agctatttaa attggtatca gcagaaacca        120
gggaaagccc ctaaactcct gatctatgct gcatccagtt tgcaaagtgg ggtcccatca        180
aggttcagtg gcagtggatc tgggacagat ttcactctca ccatcagcag tctgcaacct        240
gaagatttta caatttacta ctgtcaacag agttacagta ccccgatcac cttcggccaa        300
gggaccaagc tggagatcaa a                                                  321

SEQ ID NO: 154          moltype = AA   length = 107
FEATURE                 Location/Qualifiers
source                  1..107
                        mol_type = protein
                        organism = synthetic construct
                        note = synthetic
SEQUENCE: 154
DIQMTQSPSS LSASVGDRVT ITCRASQSIS SYLNWYQQKP GKAPKLLIYA ASSLQSGVPS          60
RFSGSGSGTD FTLTISSLQP EDFTIYYCQQ SYSTPITFGQ GTKLEIK                       107

SEQ ID NO: 155          moltype = DNA  length = 18
FEATURE                 Location/Qualifiers
source                  1..18
                        mol_type = other DNA
                        organism = synthetic construct
                        note = synthetic
SEQUENCE: 155
cagagcatta gcagctat                                                        18

SEQ ID NO: 156          moltype = AA   length = 6
FEATURE                 Location/Qualifiers
source                  1..6
                        mol_type = protein
                        organism = synthetic construct
                        note = synthetic
SEQUENCE: 156
QSISSY                                                                      6

SEQ ID NO: 157          moltype =      length =
SEQUENCE: 157
000

SEQ ID NO: 158          moltype =      length =
SEQUENCE: 158
000

SEQ ID NO: 159          moltype = DNA  length = 27
FEATURE                 Location/Qualifiers
source                  1..27
                        mol_type = other DNA
                        organism = synthetic construct
                        note = synthetic
SEQUENCE: 159
caacagagtt acagtacccc gatcacc                                              27
```

```
SEQ ID NO: 160            moltype = AA   length = 9
FEATURE                   Location/Qualifiers
source                    1..9
                          mol_type = protein
                          organism = synthetic construct
                          note = synthetic
SEQUENCE: 160
QQSYSTPIT                                                                      9

SEQ ID NO: 161            moltype = DNA  length = 348
FEATURE                   Location/Qualifiers
source                    1..348
                          mol_type = other DNA
                          organism = synthetic construct
                          note = synthetic
SEQUENCE: 161
caggtgcagc tggtgcagtc tggagctgag gtgaagaagc ctggggcctc agtgaaggtc    60
tcctgcaaga cttctggtta cacccttaacc agctatggta tcagctgggt gcgacaggcc   120
cctggacaag ggcttgagtg gatgggatgg agcagcggtc acaatggtaa cacaaactat   180
gcacagaagc tccagggcag agtcaccatg accgcagaca catccacgag cacagcctac   240
atggacctga ggagcctgag atctgacgac acggccgtgt attactgtgc gactttaact   300
ggaacctttg actactgggg ccagggaacc ctggtcaccg tctcctca                348

SEQ ID NO: 162            moltype = AA   length = 116
FEATURE                   Location/Qualifiers
source                    1..116
                          mol_type = protein
                          organism = synthetic construct
                          note = synthetic
SEQUENCE: 162
QVQLVQSGAE VKKPGASVKV SCKTSGYTLT SYGISWVRQA PGQGLEWMGW SSGHNGNTNY    60
AQKLQGRVTM TADTSTSTAY MDLRSLRSDD TAVYYCATLT GTFDYWGQGT LVTVSS       116

SEQ ID NO: 163            moltype = DNA  length = 24
FEATURE                   Location/Qualifiers
source                    1..24
                          mol_type = other DNA
                          organism = synthetic construct
                          note = synthetic
SEQUENCE: 163
ggttacacct taaccagcta tggt                                            24

SEQ ID NO: 164            moltype = AA   length = 8
FEATURE                   Location/Qualifiers
source                    1..8
                          mol_type = protein
                          organism = synthetic construct
                          note = synthetic
SEQUENCE: 164
GYTLTSYG                                                               8

SEQ ID NO: 165            moltype = DNA  length = 24
FEATURE                   Location/Qualifiers
source                    1..24
                          mol_type = other DNA
                          organism = synthetic construct
                          note = synthetic
SEQUENCE: 165
agcagcggtc acaatggtaa caca                                            24

SEQ ID NO: 166            moltype = AA   length = 8
FEATURE                   Location/Qualifiers
source                    1..8
                          mol_type = protein
                          organism = synthetic construct
                          note = synthetic
SEQUENCE: 166
SSGHNGNT                                                               8

SEQ ID NO: 167            moltype = DNA  length = 27
FEATURE                   Location/Qualifiers
source                    1..27
                          mol_type = other DNA
                          organism = synthetic construct
                          note = synthetic
SEQUENCE: 167
gcgactttaa ctggaaccctt tgactac                                        27

SEQ ID NO: 168            moltype = AA   length = 9
```

```
FEATURE                 Location/Qualifiers
source                  1..9
                        mol_type = protein
                        organism = synthetic construct
                        note = synthetic
SEQUENCE: 168
ATLTGTFDY                                                                    9

SEQ ID NO: 169          moltype = DNA  length = 324
FEATURE                 Location/Qualifiers
source                  1..324
                        mol_type = other DNA
                        organism = synthetic construct
                        note = synthetic
SEQUENCE: 169
gaaatagtga tgacgcagtc tccagccacc ctgtctgtgt ctccagggga aagagccacc    60
ctctcctgca gggccagtca gagtgttagc atcaacctag cctggtacca gcagcaccct   120
ggccaggctc ccaggctcct catctatggt gcaaccacca gggccactgg tatcccagcc   180
aggttcagtg gcagtgggtc tgggacagag ttcactctca ccatcagcag cctgcagtct   240
gaagattttg cagtttatta ctgtcaacag tataataact ggcctgcgct cactttcggc   300
ggagggacca aggtggagat caaa                                          324

SEQ ID NO: 170          moltype = AA  length = 108
FEATURE                 Location/Qualifiers
source                  1..108
                        mol_type = protein
                        organism = synthetic construct
                        note = synthetic
SEQUENCE: 170
EIVMTQSPAT LSVSPGERAT LSCRASQSVS INLAWYQQHP GQAPRLLIYG ATTRATGIPA    60
RFSGSGSGTE FTLTISSLQS EDFAVYYCQQ YNNWPALTFG GGTKVEIK                108

SEQ ID NO: 171          moltype = DNA  length = 18
FEATURE                 Location/Qualifiers
source                  1..18
                        mol_type = other DNA
                        organism = synthetic construct
                        note = synthetic
SEQUENCE: 171
cagagtgtta gcatcaac                                                  18

SEQ ID NO: 172          moltype = AA  length = 6
FEATURE                 Location/Qualifiers
source                  1..6
                        mol_type = protein
                        organism = synthetic construct
                        note = synthetic
SEQUENCE: 172
QSVSIN                                                                6

SEQ ID NO: 173          moltype =    length =
SEQUENCE: 173
000

SEQ ID NO: 174          moltype =    length =
SEQUENCE: 174
000

SEQ ID NO: 175          moltype = DNA  length = 30
FEATURE                 Location/Qualifiers
source                  1..30
                        mol_type = other DNA
                        organism = synthetic construct
                        note = synthetic
SEQUENCE: 175
caacagtata ataactggcc tgcgctcact                                     30

SEQ ID NO: 176          moltype = AA  length = 10
FEATURE                 Location/Qualifiers
source                  1..10
                        mol_type = protein
                        organism = synthetic construct
                        note = synthetic
SEQUENCE: 176
QQYNNWPALT                                                           10

SEQ ID NO: 177          moltype = DNA  length = 357
FEATURE                 Location/Qualifiers
source                  1..357
```

```
                            mol_type = other DNA
                            organism = synthetic construct
                            note = synthetic
SEQUENCE: 177
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac atttggagta ctggtactac catatactac   180
gcagactctg tgaagggccg attcaccatc tccagggaca cgccaagca ctcactttat    240
ctgcaaatga acagcctgag agccgaggac acggccgtgt attactgtgc gagagagggg   300
ataactggaa ctctctttga ctactggggc cagggaaccc tggtcaccgt ctcctca      357

SEQ ID NO: 178              moltype = AA  length = 119
FEATURE                     Location/Qualifiers
source                      1..119
                            mol_type = protein
                            organism = synthetic construct
                            note = synthetic
SEQUENCE: 178
QVQLVESGGG LVKPGGSLRL SCAASGFTFS DYYMSWIRQA PGKGLEWVSY IWSTGTTIYY    60
ADSVKGRFTI SRDNAKHSLY LQMNSLRAED TAVYYCAREG ITGTLFDYWG QGTLVTVSS    119

SEQ ID NO: 179              moltype = DNA  length = 24
FEATURE                     Location/Qualifiers
source                      1..24
                            mol_type = other DNA
                            organism = synthetic construct
                            note = synthetic
SEQUENCE: 179
ggattcacct tcagtgacta ctac                                           24

SEQ ID NO: 180              moltype = AA  length = 8
FEATURE                     Location/Qualifiers
source                      1..8
                            mol_type = protein
                            organism = synthetic construct
                            note = synthetic
SEQUENCE: 180
GFTFSDYY                                                              8

SEQ ID NO: 181              moltype = DNA  length = 24
FEATURE                     Location/Qualifiers
source                      1..24
                            mol_type = other DNA
                            organism = synthetic construct
                            note = synthetic
SEQUENCE: 181
atttggagta ctggtactac cata                                           24

SEQ ID NO: 182              moltype = AA  length = 8
FEATURE                     Location/Qualifiers
source                      1..8
                            mol_type = protein
                            organism = synthetic construct
                            note = synthetic
SEQUENCE: 182
IWSTGTTI                                                              8

SEQ ID NO: 183              moltype = DNA  length = 36
FEATURE                     Location/Qualifiers
source                      1..36
                            mol_type = other DNA
                            organism = synthetic construct
                            note = synthetic
SEQUENCE: 183
gcgagagagg ggataactgg aactctcttt gactac                              36

SEQ ID NO: 184              moltype = AA  length = 12
FEATURE                     Location/Qualifiers
source                      1..12
                            mol_type = protein
                            organism = synthetic construct
                            note = synthetic
SEQUENCE: 184
AREGITGTLF DY                                                        12

SEQ ID NO: 185              moltype = DNA  length = 321
FEATURE                     Location/Qualifiers
source                      1..321
                            mol_type = other DNA
```

```
SEQ ID NO: 185          moltype = DNA  length = 321
FEATURE                 Location/Qualifiers
source                  1..321
                        mol_type = other DNA
                        organism = synthetic construct
                        note = synthetic
SEQUENCE: 185
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtacac ttttggccag   300
gggaccaagc tggagatcaa a                                             321

SEQ ID NO: 186          moltype = AA  length = 107
FEATURE                 Location/Qualifiers
source                  1..107
                        mol_type = protein
                        organism = synthetic construct
                        note = synthetic
SEQUENCE: 186
DIQMTQSPSS LSASVGDRVT ITCRASQGIR NDLGWYQQKP GKAPKRLIYA ASSLQSGVPS    60
RFSGSGSGTE FTLTISSLQP EDFATYYCLQ HNSYPYTFGQ GTKLEIK                 107

SEQ ID NO: 187          moltype = DNA  length = 18
FEATURE                 Location/Qualifiers
source                  1..18
                        mol_type = other DNA
                        organism = synthetic construct
                        note = synthetic
SEQUENCE: 187
cagggcatta gaaatgat                                                  18

SEQ ID NO: 188          moltype = AA  length = 6
FEATURE                 Location/Qualifiers
source                  1..6
                        mol_type = protein
                        organism = synthetic construct
                        note = synthetic
SEQUENCE: 188
QGIRND                                                                6

SEQ ID NO: 189          moltype =   length =
SEQUENCE: 189
000

SEQ ID NO: 190          moltype =   length =
SEQUENCE: 190
000

SEQ ID NO: 191          moltype = DNA  length = 27
FEATURE                 Location/Qualifiers
source                  1..27
                        mol_type = other DNA
                        organism = synthetic construct
                        note = synthetic
SEQUENCE: 191
ctacagcata atagttaccc gtacact                                        27

SEQ ID NO: 192          moltype = AA  length = 9
FEATURE                 Location/Qualifiers
source                  1..9
                        mol_type = protein
                        organism = synthetic construct
                        note = synthetic
SEQUENCE: 192
LQHNSYPYT                                                             9

SEQ ID NO: 193          moltype = DNA  length = 375
FEATURE                 Location/Qualifiers
source                  1..375
                        mol_type = other DNA
                        organism = synthetic construct
                        note = synthetic
SEQUENCE: 193
gaggtgcagc tggtggagtc tgggggaggc ttggtccagc ctgggggGtc cctgagactc    60
tcctgtgcag cctctggatt caccttcagt tactatgctt tgcactgggt ccgccaggct   120
ccagggaagg gactggaata tgtttcagct attagtggta atgggggtag cacatattat   180
gcagactctg tgaagggcag attcaccatc tccagagaca aatccatgag cacggtgtat   240
ctgcaagtgg gcagcctgag ggctgaggac atggctgttt attactgtgc gagatcctat   300
gccagttcgt ccgattacca ctactactac ggtatggacg tctggggcca agggaccacg   360
gtcaccgtct cctca                                                    375
```

```
SEQ ID NO: 194            moltype = AA  length = 125
FEATURE                   Location/Qualifiers
source                    1..125
                          mol_type = protein
                          organism = synthetic construct
                          note = synthetic
SEQUENCE: 194
EVQLVESGGG LVQPGGSLRL SCAASGFTFS YYALHWVRQA PGKGLEYVSA ISGNGGSTYY    60
ADSVKGRFTI SRDKSMSTVY LQVGSLRAED MAVYYCARSY ASSSDYHYYY GMDVWGQGTT   120
VTVSS                                                               125

SEQ ID NO: 195            moltype = DNA  length = 24
FEATURE                   Location/Qualifiers
source                    1..24
                          mol_type = other DNA
                          organism = synthetic construct
                          note = synthetic
SEQUENCE: 195
ctggattcac cttcagttac tatg                                           24

SEQ ID NO: 196            moltype = AA  length = 8
FEATURE                   Location/Qualifiers
source                    1..8
                          mol_type = protein
                          organism = synthetic construct
                          note = synthetic
SEQUENCE: 196
LDSPSVTM                                                              8

SEQ ID NO: 197            moltype = DNA  length = 24
FEATURE                   Location/Qualifiers
source                    1..24
                          mol_type = other DNA
                          organism = synthetic construct
                          note = synthetic
SEQUENCE: 197
agctattagt ggtaatgggg gtag                                           24

SEQ ID NO: 198            moltype = AA  length = 5
FEATURE                   Location/Qualifiers
source                    1..5
                          mol_type = protein
                          organism = synthetic construct
                          note = synthetic
SEQUENCE: 198
SYWWG                                                                 5

SEQ ID NO: 199            moltype = DNA  length = 50
FEATURE                   Location/Qualifiers
source                    1..50
                          mol_type = other DNA
                          organism = synthetic construct
                          note = synthetic
SEQUENCE: 199
attactgtgc gagatcctat gccagttcgt ccgattacca ctactactac               50

SEQ ID NO: 200            moltype = AA  length = 17
FEATURE                   Location/Qualifiers
source                    1..17
                          mol_type = protein
                          organism = synthetic construct
                          note = synthetic
SEQUENCE: 200
ITVRDPMPVR PITTTTT                                                   17

SEQ ID NO: 201            moltype = DNA  length = 324
FEATURE                   Location/Qualifiers
source                    1..324
                          mol_type = other DNA
                          organism = synthetic construct
                          note = synthetic
SEQUENCE: 201
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324
```

```
SEQ ID NO: 202          moltype = AA  length = 108
FEATURE                 Location/Qualifiers
source                  1..108
                        mol_type = protein
                        organism = synthetic construct
                        note = synthetic
SEQUENCE: 202
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 203          moltype = DNA  length = 18
FEATURE                 Location/Qualifiers
source                  1..18
                        mol_type = other DNA
                        organism = synthetic construct
                        note = synthetic
SEQUENCE: 203
cagagcatta gcagctat                                                  18

SEQ ID NO: 204          moltype = AA  length = 6
FEATURE                 Location/Qualifiers
source                  1..6
                        mol_type = protein
                        organism = synthetic construct
                        note = synthetic
SEQUENCE: 204
QSISSY                                                                6

SEQ ID NO: 205          moltype =     length =
SEQUENCE: 205
000

SEQ ID NO: 206          moltype =     length =
SEQUENCE: 206
000

SEQ ID NO: 207          moltype = DNA  length = 30
FEATURE                 Location/Qualifiers
source                  1..30
                        mol_type = other DNA
                        organism = synthetic construct
                        note = synthetic
SEQUENCE: 207
caacagagtt acagtacccc tccgatcacc                                     30

SEQ ID NO: 208          moltype = AA  length = 10
FEATURE                 Location/Qualifiers
source                  1..10
                        mol_type = protein
                        organism = synthetic construct
                        note = synthetic
SEQUENCE: 208
QQSYSTPPIT                                                           10

SEQ ID NO: 209          moltype = DNA  length = 375
FEATURE                 Location/Qualifiers
source                  1..375
                        mol_type = other DNA
                        organism = synthetic construct
                        note = synthetic
SEQUENCE: 209
gaggtgcagc tggtggagtc tgggggaggc ttggtccagc ctgggggtc  cctgagactc    60
tcctgtgcag cctctggatt caccttcagt tactatgctt tgcactgggt ccgccaggct   120
ccagggaagg gactggaata tgtttcagct attagtggta atggggtag  cacatattat   180
gcagactctg tgaagggcag attcaccatc tccagagaca atccatgag  cacggtgtat   240
cttcaagtgg gcagcctgag ggctgaggac atggctgttt attactgtgc gagatcctat   300
gccagttcgt ccgattacca ctactactac ggtatggacg tctggggcca agggaccacg   360
gtcaccgtct cctca                                                    375

SEQ ID NO: 210          moltype = AA  length = 125
FEATURE                 Location/Qualifiers
source                  1..125
                        mol_type = protein
                        organism = synthetic construct
                        note = synthetic
SEQUENCE: 210
EVQLVESGGG LVQPGGSLRL SCAASGFTFS YYALHWVRQA PGKGLEYVSA ISGNGGSTYY    60
ADSVKGRFTI SRDKSMSTVY LQVGSLRAED MAVYYCARSY ASSSDYHYYY GMDWGQGTT    120
VTVSS                                                               125
```

```
SEQ ID NO: 211          moltype = DNA  length = 24
FEATURE                 Location/Qualifiers
source                  1..24
                        mol_type = other DNA
                        organism = synthetic construct
                        note = synthetic
SEQUENCE: 211
ggattcacct tcagttacta tgct                                              24

SEQ ID NO: 212          moltype = AA  length = 8
FEATURE                 Location/Qualifiers
source                  1..8
                        mol_type = protein
                        organism = synthetic construct
                        note = synthetic
SEQUENCE: 212
GFTFSYYA                                                                8

SEQ ID NO: 213          moltype = DNA  length = 24
FEATURE                 Location/Qualifiers
source                  1..24
                        mol_type = other DNA
                        organism = synthetic construct
                        note = synthetic
SEQUENCE: 213
attagtggta atgggggtag caca                                              24

SEQ ID NO: 214          moltype = AA  length = 8
FEATURE                 Location/Qualifiers
source                  1..8
                        mol_type = protein
                        organism = synthetic construct
                        note = synthetic
SEQUENCE: 214
ISGNGGST                                                                8

SEQ ID NO: 215          moltype = DNA  length = 54
FEATURE                 Location/Qualifiers
source                  1..54
                        mol_type = other DNA
                        organism = synthetic construct
                        note = synthetic
SEQUENCE: 215
gcgagatcct atgccagttc gtccgattac cactactact acggtatgga cgtc             54

SEQ ID NO: 216          moltype = AA  length = 18
FEATURE                 Location/Qualifiers
source                  1..18
                        mol_type = protein
                        organism = synthetic construct
                        note = synthetic
SEQUENCE: 216
ARSYASSSDY HYYYGMDV                                                     18

SEQ ID NO: 217          moltype = DNA  length = 357
FEATURE                 Location/Qualifiers
source                  1..357
                        mol_type = other DNA
                        organism = synthetic construct
                        note = synthetic
SEQUENCE: 217
gaggtgcagc tggtggagtc tgggggaggc ttggtacagc ctggggggtc cctgagactc       60
tcctgtgcag cctctggatt cacctttagc acttatgcca tgagttgggt ccgccaggct      120
ccagggatgg ggctggagtg ggtctcaact attagtggtt ttggtggtac cacatactac      180
gcagactccg tgaagggccg gttcaccatc tccagagaca attccaagaa ctcgctgtat      240
ctgcaaatga acagcctgag agccgaagac acggccgtat attactgtac gaaagatgag      300
aactgggaat cccactttga ctactggggc cagggaaccc tggtcaccgt ctcctca         357

SEQ ID NO: 218          moltype = AA  length = 119
FEATURE                 Location/Qualifiers
source                  1..119
                        mol_type = protein
                        organism = synthetic construct
                        note = synthetic
SEQUENCE: 218
EVQLVESGGG LVQPGGSLRL SCAASGFTFS TYAMSWVRQA PGMGLEWVST ISGFGGTTYY       60
ADSVKGRFTI SRDNSKNSLY LQMNSLRAED TAVYYCTKDE NWESHFDYWG QGTLVTVSS       119
```

```
SEQ ID NO: 219          moltype = DNA  length = 24
FEATURE                 Location/Qualifiers
source                  1..24
                        mol_type = other DNA
                        organism = synthetic construct
                        note = synthetic
SEQUENCE: 219
ggattcacct ttagcactta tgcc                                          24

SEQ ID NO: 220          moltype = AA  length = 8
FEATURE                 Location/Qualifiers
source                  1..8
                        mol_type = protein
                        organism = synthetic construct
                        note = synthetic
SEQUENCE: 220
GFTFSTYA                                                            8

SEQ ID NO: 221          moltype = DNA  length = 24
FEATURE                 Location/Qualifiers
source                  1..24
                        mol_type = other DNA
                        organism = synthetic construct
                        note = synthetic
SEQUENCE: 221
attagtggtt ttggtggtac caca                                          24

SEQ ID NO: 222          moltype = AA  length = 8
FEATURE                 Location/Qualifiers
source                  1..8
                        mol_type = protein
                        organism = synthetic construct
                        note = synthetic
SEQUENCE: 222
ISGFGGTT                                                            8

SEQ ID NO: 223          moltype = DNA  length = 36
FEATURE                 Location/Qualifiers
source                  1..36
                        mol_type = other DNA
                        organism = synthetic construct
                        note = synthetic
SEQUENCE: 223
acgaaagatg agaactggga atcccacttt gactac                             36

SEQ ID NO: 224          moltype = AA  length = 12
FEATURE                 Location/Qualifiers
source                  1..12
                        mol_type = protein
                        organism = synthetic construct
                        note = synthetic
SEQUENCE: 224
TKDENWESHF DY                                                       12

SEQ ID NO: 225          moltype = DNA  length = 324
FEATURE                 Location/Qualifiers
source                  1..324
                        mol_type = other DNA
                        organism = synthetic construct
                        note = synthetic
SEQUENCE: 225
gacatccaga tgacccagtc tccatcctcc ctgtctgcat ctgtaggaga cagagtcacc   60
atcacttgcc gggcaagtca gaccattagc agctatttaa attggtatca gcagaaacca  120
gggaaagccc ctaagctcct gatctatgct acatccagtt tacaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 226          moltype = AA  length = 108
FEATURE                 Location/Qualifiers
source                  1..108
                        mol_type = protein
                        organism = synthetic construct
                        note = synthetic
SEQUENCE: 226
DIQMTQSPSS LSASVGDRVT ITCRASQTIS SYLNWYQQKP GKAPKLLIYA TSSLQSGVPS   60
RFSGSGSGTD FTLTISSLQP EDFATYYCQQ SYSTPPITFG QGTRLEIK               108

SEQ ID NO: 227          moltype = DNA  length = 18
```

| | | |
|---|---|---|
| FEATURE | Location/Qualifiers | |
| source | 1..18 | |
| | mol_type = other DNA | |
| | organism = synthetic construct | |
| | note = synthetic | |
| SEQUENCE: 227 | | |
| cagaccatta gcagctat | | 18 |
| | | |
| SEQ ID NO: 228 | moltype = AA  length = 6 | |
| FEATURE | Location/Qualifiers | |
| source | 1..6 | |
| | mol_type = protein | |
| | organism = synthetic construct | |
| | note = synthetic | |
| SEQUENCE: 228 | | |
| QTISSY | | 6 |
| | | |
| SEQ ID NO: 229 | moltype =   length = | |
| SEQUENCE: 229 | | |
| 000 | | |
| | | |
| SEQ ID NO: 230 | moltype =   length = | |
| SEQUENCE: 230 | | |
| 000 | | |
| | | |
| SEQ ID NO: 231 | moltype = DNA  length = 30 | |
| FEATURE | Location/Qualifiers | |
| source | 1..30 | |
| | mol_type = other DNA | |
| | organism = synthetic construct | |
| | note = synthetic | |
| SEQUENCE: 231 | | |
| caacagagtt acagtacccc tccgatcacc | | 30 |
| | | |
| SEQ ID NO: 232 | moltype = AA  length = 10 | |
| FEATURE | Location/Qualifiers | |
| source | 1..10 | |
| | mol_type = protein | |
| | organism = synthetic construct | |
| | note = synthetic | |
| SEQUENCE: 232 | | |
| QQSYSTPPIT | | 10 |
| | | |
| SEQ ID NO: 233 | moltype = DNA  length = 357 | |
| FEATURE | Location/Qualifiers | |
| source | 1..357 | |
| | mol_type = other DNA | |
| | organism = synthetic construct | |
| | note = synthetic | |
| SEQUENCE: 233 | | |
| gaggtgcagc tggtggagtc tgggggaggc ttggtacagc ctggggggtc cctgagactc | | 60 |
| tcctgtgcag cctctggatt cacctttaac acctatgcca tgacctgggt ccgccaggct | | 120 |
| ccagggaagg ggctggagtg ggtctcagaa attagtggtt atggtggtac acatactac | | 180 |
| gcagactccg tgaagggccg gttcaccatc tccagagaca attccaagaa cacgctgtat | | 240 |
| ttgcaaatga acagcctgag agccgaagac acggccgtat attactgtgc gaaagacgaa | | 300 |
| aactggaact cacactttga ctactggggc cagggaaccc tggtcaccgt ctcctca | | 357 |
| | | |
| SEQ ID NO: 234 | moltype = AA  length = 119 | |
| FEATURE | Location/Qualifiers | |
| source | 1..119 | |
| | mol_type = protein | |
| | organism = synthetic construct | |
| | note = synthetic | |
| SEQUENCE: 234 | | |
| EVQLVESGGG LVQPGGSLRL SCAASGFTFN TYAMTWVRQA PGKGLEWVSE ISGYGGTTYY | | 60 |
| ADSVKGRFTI SRDNSKNTLY LQMNSLRAED TAVYYCAKDE NWNSHFDYWG QGTLVTVSS | | 119 |
| | | |
| SEQ ID NO: 235 | moltype = DNA  length = 24 | |
| FEATURE | Location/Qualifiers | |
| source | 1..24 | |
| | mol_type = other DNA | |
| | organism = synthetic construct | |
| | note = synthetic | |
| SEQUENCE: 235 | | |
| ggattcacct ttaacaccta tgcc | | 24 |
| | | |
| SEQ ID NO: 236 | moltype = AA  length = 8 | |
| FEATURE | Location/Qualifiers | |
| source | 1..8 | |

```
                        mol_type = protein
                        organism = synthetic construct
                        note = synthetic
SEQUENCE: 236
GFTFNTYA                                                                     8

SEQ ID NO: 237          moltype = DNA   length = 24
FEATURE                 Location/Qualifiers
source                  1..24
                        mol_type = other DNA
                        organism = synthetic construct
                        note = synthetic
SEQUENCE: 237
attagtggtt atggtggtac caca                                                  24

SEQ ID NO: 238          moltype = AA   length = 8
FEATURE                 Location/Qualifiers
source                  1..8
                        mol_type = protein
                        organism = synthetic construct
                        note = synthetic
SEQUENCE: 238
ISGYGGTT                                                                     8

SEQ ID NO: 239          moltype = DNA   length = 36
FEATURE                 Location/Qualifiers
source                  1..36
                        mol_type = other DNA
                        organism = synthetic construct
                        note = synthetic
SEQUENCE: 239
gcgaaagacg aaaactggaa ctcacacttt gactac                                     36

SEQ ID NO: 240          moltype = AA   length = 12
FEATURE                 Location/Qualifiers
source                  1..12
                        mol_type = protein
                        organism = synthetic construct
                        note = synthetic
SEQUENCE: 240
AKDENWNSHF DY                                                               12

SEQ ID NO: 241          moltype = DNA   length = 327
FEATURE                 Location/Qualifiers
source                  1..327
                        mol_type = other DNA
                        organism = synthetic construct
                        note = synthetic
SEQUENCE: 241
gacatccaga tgacccagtc tccatcctcc ctgtctgcat ctgtaggaga cagagtcacc           60
atcacttgcc gggcaagtca gagcattagc agctatttaa attggtatca gcagaaacca          120
gggaaagccc ctaagctcct gatctatgct gcatccagtt tgcaaagtgg ggtcccatca          180
aggttcagtg gcagtggatc tgggacagat ttcactctca ccatcagcag tctgcaacct          240
gaagattttg caacttacta ctgtcaacag agttacagta cccctccgat caccttcggc          300
caagggacac gactggagat taaacga                                              327

SEQ ID NO: 242          moltype = AA   length = 109
FEATURE                 Location/Qualifiers
source                  1..109
                        mol_type = protein
                        organism = synthetic construct
                        note = synthetic
SEQUENCE: 242
DIQMTQSPSS LSASVGDRVT ITCRASQSIS SYLNWYQQKP GKAPKLLIYA ASSLQSGVPS           60
RFSGSGSGTD FTLTISSLQP EDFATYYCQQ SYSTPPITFG QGTRLEIKR                      109

SEQ ID NO: 243          moltype = DNA   length = 18
FEATURE                 Location/Qualifiers
source                  1..18
                        mol_type = other DNA
                        organism = synthetic construct
                        note = synthetic
SEQUENCE: 243
cagagcatta gcagctat                                                         18

SEQ ID NO: 244          moltype = AA   length = 6
FEATURE                 Location/Qualifiers
source                  1..6
                        mol_type = protein
```

```
SEQUENCE: 244
QSISSY                                                                  6

SEQ ID NO: 245          moltype =    length =
SEQUENCE: 245
000

SEQ ID NO: 246          moltype =    length =
SEQUENCE: 246
000

SEQ ID NO: 247          moltype = DNA   length = 30
FEATURE                 Location/Qualifiers
source                  1..30
                        mol_type = other DNA
                        organism = synthetic construct
                        note = synthetic
SEQUENCE: 247
caacagagtt acagtacccc tccgatcacc                                        30

SEQ ID NO: 248          moltype = AA   length = 10
FEATURE                 Location/Qualifiers
source                  1..10
                        mol_type = protein
                        organism = synthetic construct
                        note = synthetic
SEQUENCE: 248
QQSYSTPPIT                                                              10

SEQ ID NO: 249          moltype = DNA   length = 360
FEATURE                 Location/Qualifiers
source                  1..360
                        mol_type = other DNA
                        organism = synthetic construct
                        note = synthetic
SEQUENCE: 249
caggtgcagc tggtggagtc tgggggaggc ttggtcaagc ctggagggtc cctgagactc        60
tcctgtgcag cctctggatt caccttcagt gacaactaca tgagctggat ccgccaggct       120
ccagggaagg ggctggagtg ggtttcatat attagtagta gtggtagtat catatactac       180
gcagactctg tgaagggccg attcaccatc tccaggaca acgccaagaa ctcactgtat        240
ctgcaaatga acagcctgag agccgaggac acggccatat attactgtgc gagaggcgga       300
tggggatggg actggtactt cgatctctgg ggccgtggca ccctggtcac tgtctcctca       360

SEQ ID NO: 250          moltype = AA   length = 120
FEATURE                 Location/Qualifiers
source                  1..120
                        mol_type = protein
                        organism = synthetic construct
                        note = synthetic
SEQUENCE: 250
QVQLVESGGG LVKPGGSLRL SCAASGFTFS DNYMSWIRQA PGKGLEWVSY ISSSGSIIYY        60
ADSVKGRFTI SRDNAKNSLY LQMNSLRAED TAIYYCARGG WGWDWYFDLW GRGTLVTVSS       120

SEQ ID NO: 251          moltype = DNA   length = 24
FEATURE                 Location/Qualifiers
source                  1..24
                        mol_type = other DNA
                        organism = synthetic construct
                        note = synthetic
SEQUENCE: 251
ggattcacct tcagtgacaa ctac                                              24

SEQ ID NO: 252          moltype = AA   length = 8
FEATURE                 Location/Qualifiers
source                  1..8
                        mol_type = protein
                        organism = synthetic construct
                        note = synthetic
SEQUENCE: 252
GFTFSDNY                                                                8

SEQ ID NO: 253          moltype = DNA   length = 24
FEATURE                 Location/Qualifiers
source                  1..24
                        mol_type = other DNA
                        organism = synthetic construct
                        note = synthetic
```

```
SEQUENCE: 253
attagtagta gtggtagtat cata                                               24

SEQ ID NO: 254          moltype = AA  length = 8
FEATURE                 Location/Qualifiers
source                  1..8
                        mol_type = protein
                        organism = synthetic construct
                        note = synthetic
SEQUENCE: 254
ISSSGSII                                                                  8

SEQ ID NO: 255          moltype = DNA  length = 39
FEATURE                 Location/Qualifiers
source                  1..39
                        mol_type = other DNA
                        organism = synthetic construct
                        note = synthetic
SEQUENCE: 255
gcgagaggcg gatggggatg ggactggtac ttcgatctc                                39

SEQ ID NO: 256          moltype = AA  length = 13
FEATURE                 Location/Qualifiers
source                  1..13
                        mol_type = protein
                        organism = synthetic construct
                        note = synthetic
SEQUENCE: 256
ARGGWGWDWY FDL                                                           13

SEQ ID NO: 257          moltype = DNA  length = 324
FEATURE                 Location/Qualifiers
source                  1..324
                        mol_type = other DNA
                        organism = synthetic construct
                        note = synthetic
SEQUENCE: 257
gacatccaga tgacccagtc tccatcctcc ctgtctgcat ctgtaggaga cagagtcacc         60
atcacttgcc gggcaagtca gagcattagc agctatttaa attggtatca gcagaaacca       120
gggaaagccc ctaagctcct gatctatgct gcatccagtt tgcaaagtgg ggtcccatca       180
aggttcagtg gcagtggatc tgggacagat ttcactctca ccatcagcag tctgcaacct       240
gaagatttg caacttacta ctgtcaacag agttacagta cccctccgat cacccttcggc      300
caagggacca agctggagat caaa                                              324

SEQ ID NO: 258          moltype = AA  length = 108
FEATURE                 Location/Qualifiers
source                  1..108
                        mol_type = protein
                        organism = synthetic construct
                        note = synthetic
SEQUENCE: 258
DIQMTQSPSS LSASVGDRVT ITCRASQSIS SYLNWYQQKP GKAPKLLIYA ASSLQSGVPS         60
RFSGSGSGTD FTLTISSLQP EDFATYYCQQ SYSTPPITFG QGTKLEIK                    108

SEQ ID NO: 259          moltype = DNA  length = 18
FEATURE                 Location/Qualifiers
source                  1..18
                        mol_type = other DNA
                        organism = synthetic construct
                        note = synthetic
SEQUENCE: 259
cagagcatta gcagctat                                                      18

SEQ ID NO: 260          moltype = AA  length = 6
FEATURE                 Location/Qualifiers
source                  1..6
                        mol_type = protein
                        organism = synthetic construct
                        note = synthetic
SEQUENCE: 260
QSISSY                                                                    6

SEQ ID NO: 261          moltype =    length =
SEQUENCE: 261
000

SEQ ID NO: 262          moltype =    length =
SEQUENCE: 262
000
```

```
SEQ ID NO: 263           moltype = DNA   length = 30
FEATURE                  Location/Qualifiers
source                   1..30
                         mol_type = other DNA
                         organism = synthetic construct
                         note = synthetic
SEQUENCE: 263
caacagagtt acagtacccc tccgatcacc                                        30

SEQ ID NO: 264           moltype = AA    length = 10
FEATURE                  Location/Qualifiers
source                   1..10
                         mol_type = protein
                         organism = synthetic construct
                         note = synthetic
SEQUENCE: 264
QQSYSTPPIT                                                              10

SEQ ID NO: 265           moltype = DNA   length = 372
FEATURE                  Location/Qualifiers
source                   1..372
                         mol_type = other DNA
                         organism = synthetic construct
                         note = synthetic
SEQUENCE: 265
gaggtgcagc tggtggagtc tgggggaaat gtggtacggc ctggggggtc cctgagactc        60
tcctgtgcag cctctggatt caccttgat gattatggca tgagctgggt ccgccaagct       120
ccagggaagg ggctggagtg ggtctctggt attaattgga atggtgatag cacaaattat       180
gcagactctg tgaagggccg attcaccatc tccagagaca acgccaagaa ctccctgtat       240
ctgcaaatga acagtctgag agccgaggac acggccttgt atcactgtgc gagagcgggg       300
attgtagtag actggaatta cgcgggctgg ttcgacccct ggggccaggg aaccctggtc       360
accgtctcct ca                                                          372

SEQ ID NO: 266           moltype = AA    length = 124
FEATURE                  Location/Qualifiers
source                   1..124
                         mol_type = protein
                         organism = synthetic construct
                         note = synthetic
SEQUENCE: 266
EVQLVESGGN VVRPGGSLRL SCAASGFTFD DYGMSWVRQA PGKGLEWVSG INWNGDSTNY        60
ADSVKGRFTI SRDNAKNSLY LQMNSLRAED TALYHCARAG IVVDWNYAGW FDPWGQGTLV       120
TVSS                                                                   124

SEQ ID NO: 267           moltype = DNA   length = 24
FEATURE                  Location/Qualifiers
source                   1..24
                         mol_type = other DNA
                         organism = synthetic construct
                         note = synthetic
SEQUENCE: 267
ggattcacct ttgatgatta tggc                                              24

SEQ ID NO: 268           moltype = AA    length = 8
FEATURE                  Location/Qualifiers
source                   1..8
                         mol_type = protein
                         organism = synthetic construct
                         note = synthetic
SEQUENCE: 268
GFTFDDYG                                                                 8

SEQ ID NO: 269           moltype = DNA   length = 24
FEATURE                  Location/Qualifiers
source                   1..24
                         mol_type = other DNA
                         organism = synthetic construct
                         note = synthetic
SEQUENCE: 269
attaattgga atggtgatag caca                                              24

SEQ ID NO: 270           moltype = AA    length = 8
FEATURE                  Location/Qualifiers
source                   1..8
                         mol_type = protein
                         organism = synthetic construct
                         note = synthetic
SEQUENCE: 270
```

INWNGDST 8

SEQ ID NO: 271    moltype = DNA  length = 51
FEATURE           Location/Qualifiers
source            1..51
                  mol_type = other DNA
                  organism = synthetic construct
                  note = synthetic
SEQUENCE: 271
gcgagagcgg ggattgtagt agactggaat tacgcgggct ggttcgaccc c    51

SEQ ID NO: 272    moltype = AA  length = 17
FEATURE           Location/Qualifiers
source            1..17
                  mol_type = protein
                  organism = synthetic construct
                  note = synthetic
SEQUENCE: 272
ARAGIVVDWN YAGWFDP    17

SEQ ID NO: 273    moltype = DNA  length = 324
FEATURE           Location/Qualifiers
source            1..324
                  mol_type = other DNA
                  organism = synthetic construct
                  note = synthetic
SEQUENCE: 273
gacatccaga tgacccagtc tccatcctcc ctgtctgcat ctgtaggaga cagagtcacc    60
atcacttgcc gggcaagtca gagcattagc agctatttaa attggtatca gcaggaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacca gctggagat caaa   324

SEQ ID NO: 274    moltype = AA  length = 108
FEATURE           Location/Qualifiers
source            1..108
                  mol_type = protein
                  organism = synthetic construct
                  note = synthetic
SEQUENCE: 274
DIQMTQSPSS LSASVGDRVT ITCRASQSIS SYLNWYQQEP GKAPKLLIYA ASSLQSGVPS    60
RFSGSGSGTD FTLTISSLQP EDFATYYCQQ SYSTPPITFG QGTKLEIK   108

SEQ ID NO: 275    moltype = DNA  length = 18
FEATURE           Location/Qualifiers
source            1..18
                  mol_type = other DNA
                  organism = synthetic construct
                  note = synthetic
SEQUENCE: 275
cagagcatta gcagctat    18

SEQ ID NO: 276    moltype = AA  length = 6
FEATURE           Location/Qualifiers
source            1..6
                  mol_type = protein
                  organism = synthetic construct
                  note = synthetic
SEQUENCE: 276
QSISSY    6

SEQ ID NO: 277    moltype =   length =
SEQUENCE: 277
000

SEQ ID NO: 278    moltype =   length =
SEQUENCE: 278
000

SEQ ID NO: 279    moltype = DNA  length = 30
FEATURE           Location/Qualifiers
source            1..30
                  mol_type = other DNA
                  organism = synthetic construct
                  note = synthetic
SEQUENCE: 279
caacagagtt acagtacccc tccgatcacc    30

-continued

| | | |
|---|---|---|
| SEQ ID NO: 280 | moltype = AA length = 10 | |
| FEATURE | Location/Qualifiers | |
| source | 1..10 | |
| | mol_type = protein | |
| | organism = synthetic construct | |
| | note = synthetic | |
| SEQUENCE: 280 | | |
| QQSYSTPPIT | | 10 |

| | | |
|---|---|---|
| SEQ ID NO: 281 | moltype = DNA length = 375 | |
| FEATURE | Location/Qualifiers | |
| source | 1..375 | |
| | mol_type = other DNA | |
| | organism = synthetic construct | |
| | note = synthetic | |

SEQUENCE: 281
```
gaggtgcagc tggtggagtc tgggggaggc ttggtccagc ctggggggtc cctgagactc    60
tcctgtgcag cctctggatt cacctttcact ttctatgcta tgcactgggt ccgccaggct   120
ccagggaagg gactgaata tgtttcaggt attagcagta atgggggaag cacaaaatat    180
gcagactctg tgaagggcag attcaccatt tccagagaca attccaagaa cacgctgtat   240
cttcaaatgg gcagcctgag agctgaggac ttggctgtgt attactgtgc gagatcgtat   300
gccagctcgt cggattacca ctactactac ggtatggacg tctggggcca agggaccacg   360
gtcaccgtct cctca                                                    375
```

| | | |
|---|---|---|
| SEQ ID NO: 282 | moltype = AA length = 125 | |
| FEATURE | Location/Qualifiers | |
| source | 1..125 | |
| | mol_type = protein | |
| | organism = synthetic construct | |
| | note = synthetic | |

SEQUENCE: 282
```
EVQLVESGGG LVQPGGSLRL SCAASGFTFT FYAMHWVRQA PGKGLEYVSG ISSNGGSTKY    60
ADSVKGRFTI SRDNSKNTLY LQMGSLRAED LAVYYCARSY ASSSDYHYYY GMDVWGQGTT   120
VTVSS                                                               125
```

| | | |
|---|---|---|
| SEQ ID NO: 283 | moltype = DNA length = 24 | |
| FEATURE | Location/Qualifiers | |
| source | 1..24 | |
| | mol_type = other DNA | |
| | organism = synthetic construct | |
| | note = synthetic | |
| SEQUENCE: 283 | | |
| ggattcacct tcactttcta tgct | | 24 |

| | | |
|---|---|---|
| SEQ ID NO: 284 | moltype = AA length = 8 | |
| FEATURE | Location/Qualifiers | |
| source | 1..8 | |
| | mol_type = protein | |
| | organism = synthetic construct | |
| | note = synthetic | |
| SEQUENCE: 284 | | |
| GFTFTFYA | | 8 |

| | | |
|---|---|---|
| SEQ ID NO: 285 | moltype = DNA length = 24 | |
| FEATURE | Location/Qualifiers | |
| source | 1..24 | |
| | mol_type = other DNA | |
| | organism = synthetic construct | |
| | note = synthetic | |
| SEQUENCE: 285 | | |
| attagcagta atgggggaag caca | | 24 |

| | | |
|---|---|---|
| SEQ ID NO: 286 | moltype = AA length = 8 | |
| FEATURE | Location/Qualifiers | |
| source | 1..8 | |
| | mol_type = protein | |
| | organism = synthetic construct | |
| | note = synthetic | |
| SEQUENCE: 286 | | |
| ISSNGGST | | 8 |

| | | |
|---|---|---|
| SEQ ID NO: 287 | moltype = DNA length = 54 | |
| FEATURE | Location/Qualifiers | |
| source | 1..54 | |
| | mol_type = other DNA | |
| | organism = synthetic construct | |
| | note = synthetic | |
| SEQUENCE: 287 | | |
| gcgagatcgt atgccagctc gtcggattac cactactact acggtatgga cgtc | | 54 |

```
SEQ ID NO: 288          moltype = AA  length = 18
FEATURE                 Location/Qualifiers
source                  1..18
                        mol_type = protein
                        organism = synthetic construct
                        note = synthetic
SEQUENCE: 288
ARSYASSSDY HYYYGMDV                                                  18

SEQ ID NO: 289          moltype = DNA  length = 324
FEATURE                 Location/Qualifiers
source                  1..324
                        mol_type = other DNA
                        organism = synthetic construct
                        note = synthetic
SEQUENCE: 289
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

SEQ ID NO: 290          moltype = AA  length = 108
FEATURE                 Location/Qualifiers
source                  1..108
                        mol_type = protein
                        organism = synthetic construct
                        note = synthetic
SEQUENCE: 290
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 291          moltype = DNA  length = 18
FEATURE                 Location/Qualifiers
source                  1..18
                        mol_type = other DNA
                        organism = synthetic construct
                        note = synthetic
SEQUENCE: 291
cagagcatta gcagctat                                                  18

SEQ ID NO: 292          moltype = AA  length = 6
FEATURE                 Location/Qualifiers
source                  1..6
                        mol_type = protein
                        organism = synthetic construct
                        note = synthetic
SEQUENCE: 292
QSISSY                                                                6

SEQ ID NO: 293          moltype =     length =
SEQUENCE: 293
000

SEQ ID NO: 294          moltype =     length =
SEQUENCE: 294
000

SEQ ID NO: 295          moltype = DNA  length = 30
FEATURE                 Location/Qualifiers
source                  1..30
                        mol_type = other DNA
                        organism = synthetic construct
                        note = synthetic
SEQUENCE: 295
caacagagtt acagtacccc tccgatcacc                                     30

SEQ ID NO: 296          moltype = AA  length = 10
FEATURE                 Location/Qualifiers
source                  1..10
                        mol_type = protein
                        organism = synthetic construct
                        note = synthetic
SEQUENCE: 296
QQSYSTPPIT                                                           10

SEQ ID NO: 297          moltype = DNA  length = 357
```

```
FEATURE              Location/Qualifiers
source               1..357
                     mol_type = other DNA
                     organism = synthetic construct
                     note = synthetic
SEQUENCE: 297
gaagtgcagc tggtggagtc tgggggaggc gtggtacagc ctgggggtc  cctgagactc   60
tcctgtgcag cctctggact cacctttgat gattatgtca tgcactgggt ccgccaagct  120
ccagggaagg gtctggagtg ggtctctctt ataagtggga atggaggtaa cacagactat  180
gtagactctg tgaaggccg  attcaccatc tccagagaca acagcaaaaa ctccctgtat  240
ctgcaaatga acagtctgag aactgaggac accgccttgt attactgtgc aaaagatatc  300
ggctgggctg atgcttttga tatctgggc  caagggacaa tggtcaccgt ctcttca    357

SEQ ID NO: 298       moltype = AA  length = 119
FEATURE              Location/Qualifiers
source               1..119
                     mol_type = protein
                     organism = synthetic construct
                     note = synthetic
SEQUENCE: 298
EVQLVESGGG VVQPGGSLRL SCAASGLTFD DYVMHWVRQA PGKGLEWVSL ISGNGGNTDY   60
VDSVKGRFTI SRDNSKNSLY LQMNSLRTED TALYYCAKDI GWADAFDIWG QGTMVTVSS   119

SEQ ID NO: 299       moltype = DNA  length = 24
FEATURE              Location/Qualifiers
source               1..24
                     mol_type = other DNA
                     organism = synthetic construct
                     note = synthetic
SEQUENCE: 299
ggactcacct ttgatgatta tgtc                                          24

SEQ ID NO: 300       moltype = AA  length = 8
FEATURE              Location/Qualifiers
source               1..8
                     mol_type = protein
                     organism = synthetic construct
                     note = synthetic
SEQUENCE: 300
GLTFDDYV                                                             8

SEQ ID NO: 301       moltype = DNA  length = 24
FEATURE              Location/Qualifiers
source               1..24
                     mol_type = other DNA
                     organism = synthetic construct
                     note = synthetic
SEQUENCE: 301
ataagtggga atggaggtaa caca                                          24

SEQ ID NO: 302       moltype = AA  length = 8
FEATURE              Location/Qualifiers
source               1..8
                     mol_type = protein
                     organism = synthetic construct
                     note = synthetic
SEQUENCE: 302
ISGNGGNT                                                             8

SEQ ID NO: 303       moltype = DNA  length = 36
FEATURE              Location/Qualifiers
source               1..36
                     mol_type = other DNA
                     organism = synthetic construct
                     note = synthetic
SEQUENCE: 303
gcaaaagata tcggctgggc tgatgctttt gatatc                             36

SEQ ID NO: 304       moltype = AA  length = 12
FEATURE              Location/Qualifiers
source               1..12
                     mol_type = protein
                     organism = synthetic construct
                     note = synthetic
SEQUENCE: 304
AKDIGWADAF DI                                                       12

SEQ ID NO: 305       moltype = DNA  length = 321
FEATURE              Location/Qualifiers
```

| source | 1..321
mol_type = other DNA
organism = synthetic construct
note = synthetic |
|---|---|

SEQUENCE: 305

```
gacatccaga tgacccagtc tccatcctcc ctgtctgcat ctgtaggaga cagagtcacc    60
atcacttgcc gggcaagtca gagcgttagc ccctatttaa attggtatca gcagaaccca   120
gggaaagccc ctaagttcct gatctttgct gcatccaatt tgcaaagtgg ggtcccatca   180
aggttcagtg gcagtggatc tgggacagat ttcactctca ccatcagctc tctgcaacct   240
gaagattttg caacttacta ctgtcaacag agttacacca ccccgtacac ttttggccag   300
gggaccaagc tggagatcaa a                                             321
```

| SEQ ID NO: 306
FEATURE
source | moltype = AA  length = 107
Location/Qualifiers
1..107
mol_type = protein
organism = synthetic construct
note = synthetic |
|---|---|

SEQUENCE: 306

```
DIQMTQSPSS LSASVGDRVT ITCRASQSVS PYLNWYQQNP GKAPKFLIFA ASNLQSGVPS    60
RFSGSGSGTD FTLTISSLQP EDFATYYCQQ SYTTPYTFGQ GTKLEIK                 107
```

| SEQ ID NO: 307
FEATURE
source | moltype = DNA  length = 18
Location/Qualifiers
1..18
mol_type = other DNA
organism = synthetic construct
note = synthetic |
|---|---|

SEQUENCE: 307

```
cagagcgtta gcccctat                                                  18
```

| SEQ ID NO: 308
FEATURE
source | moltype = AA  length = 6
Location/Qualifiers
1..6
mol_type = protein
organism = synthetic construct
note = synthetic |
|---|---|

SEQUENCE: 308

```
QSVSPY                                                                6
```

| SEQ ID NO: 309
SEQUENCE: 309
000 | moltype =    length = |
|---|---|

| SEQ ID NO: 310
SEQUENCE: 310
000 | moltype =    length = |
|---|---|

| SEQ ID NO: 311
FEATURE
source | moltype = DNA  length = 27
Location/Qualifiers
1..27
mol_type = other DNA
organism = synthetic construct
note = synthetic |
|---|---|

SEQUENCE: 311

```
caacagagtt acaccacccc gtacact                                        27
```

| SEQ ID NO: 312
FEATURE
source | moltype = AA  length = 9
Location/Qualifiers
1..9
mol_type = protein
organism = synthetic construct
note = synthetic |
|---|---|

SEQUENCE: 312

```
QQSYTTPYT                                                             9
```

| SEQ ID NO: 313
FEATURE
source | moltype = DNA  length = 360
Location/Qualifiers
1..360
mol_type = other DNA
organism = synthetic construct
note = synthetic |
|---|---|

SEQUENCE: 313

```
gaggtgcagc tggtggagtc tgggggaggc gtggtacagc ctggggggtc cctgagactc    60
tcctgtgcag cctctggatt cacctttagt aactatggca tgcactgggt ccgccaggct   120
ccagggaagg gactggagtg ggtctcagtt attagtggta atggtggtaa cacaaactat   180
gtagactccg tgaagggccg attcaccatc tccagagaca attccaagaa ctccctgtat   240
ctgcaaatga acagcctgag agccgaggac acggccgtgt attactgtgc gaaaggtatt   300
agtggctggg ctgatgcttt tgatatctgg ggccaaggga caatggtcac cgtctcttca   360
```

```
SEQ ID NO: 314          moltype = AA  length = 120
FEATURE                 Location/Qualifiers
source                  1..120
                        mol_type = protein
                        organism = synthetic construct
                        note = synthetic
SEQUENCE: 314
EVQLVESGGG VVQPGGSLRL SCAASGFTFS NYGMHWVRQA PGKGLEWVSV ISGNGGNTNY   60
VDSVEGRFTI SRDNSKNSLY LQMNSLRAED TAVYYCAKGI SGWADAFDIW GQGTMVTVSS  120

SEQ ID NO: 315          moltype = DNA  length = 24
FEATURE                 Location/Qualifiers
source                  1..24
                        mol_type = other DNA
                        organism = synthetic construct
                        note = synthetic
SEQUENCE: 315
ggattcacct ttagtaacta tggc                                         24

SEQ ID NO: 316          moltype = AA  length = 8
FEATURE                 Location/Qualifiers
source                  1..8
                        mol_type = protein
                        organism = synthetic construct
                        note = synthetic
SEQUENCE: 316
GFTFSNYG                                                            8

SEQ ID NO: 317          moltype = DNA  length = 24
FEATURE                 Location/Qualifiers
source                  1..24
                        mol_type = other DNA
                        organism = synthetic construct
                        note = synthetic
SEQUENCE: 317
attagtggta atggtggtaa caca                                         24

SEQ ID NO: 318          moltype = AA  length = 8
FEATURE                 Location/Qualifiers
source                  1..8
                        mol_type = protein
                        organism = synthetic construct
                        note = synthetic
SEQUENCE: 318
ISGNGGNT                                                            8

SEQ ID NO: 319          moltype = DNA  length = 39
FEATURE                 Location/Qualifiers
source                  1..39
                        mol_type = other DNA
                        organism = synthetic construct
                        note = synthetic
SEQUENCE: 319
gcgaaaggta ttagtggctg ggctgatgct tttgatatc                         39

SEQ ID NO: 320          moltype = AA  length = 13
FEATURE                 Location/Qualifiers
source                  1..13
                        mol_type = protein
                        organism = synthetic construct
                        note = synthetic
SEQUENCE: 320
AKGISGWADA FDI                                                     13

SEQ ID NO: 321          moltype = DNA  length = 321
FEATURE                 Location/Qualifiers
source                  1..321
                        mol_type = other DNA
                        organism = synthetic construct
                        note = synthetic
SEQUENCE: 321
gacatccaga tgacccagtc tccatcctcc ctgtctgcat ctgtaggaga cagagtcacc   60
atcacttgcc gggcaagtca gagcgttagc ccctatttaa attggtatca gcagaaacca  120
gggaaagccc ctaaattcct gatctttgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta ccccgtacac ttttggccag  300
gggaccaagc tggagatcaa a                                            321
```

```
SEQ ID NO: 322            moltype = AA   length = 107
FEATURE                   Location/Qualifiers
source                    1..107
                          mol_type = protein
                          organism = synthetic construct
                          note = synthetic
SEQUENCE: 322
DIQMTQSPSS LSASVGDRVT ITCRASQSVS PYLNWYQQKP GKAPKFLIFA ASSLQSGVPS    60
RFSGSGSGTD FTLTISSLQP EDFATYYCQQ SYSTPYTFGQ GTKLEIK                  107

SEQ ID NO: 323            moltype = DNA   length = 18
FEATURE                   Location/Qualifiers
source                    1..18
                          mol_type = other DNA
                          organism = synthetic construct
                          note = synthetic
SEQUENCE: 323
cagagcgtta gcccctat                                                  18

SEQ ID NO: 324            moltype = AA   length = 6
FEATURE                   Location/Qualifiers
source                    1..6
                          mol_type = protein
                          organism = synthetic construct
                          note = synthetic
SEQUENCE: 324
QSVSPY                                                               6

SEQ ID NO: 325            moltype =    length =
SEQUENCE: 325
000

SEQ ID NO: 326            moltype =    length =
SEQUENCE: 326
000

SEQ ID NO: 327            moltype = DNA   length = 27
FEATURE                   Location/Qualifiers
source                    1..27
                          mol_type = other DNA
                          organism = synthetic construct
                          note = synthetic
SEQUENCE: 327
caacagagtt acagtacccc gtacact                                        27

SEQ ID NO: 328            moltype = AA   length = 9
FEATURE                   Location/Qualifiers
source                    1..9
                          mol_type = protein
                          organism = synthetic construct
                          note = synthetic
SEQUENCE: 328
QQSYSTPYT                                                            9

SEQ ID NO: 329            moltype = DNA   length = 363
FEATURE                   Location/Qualifiers
source                    1..363
                          mol_type = other DNA
                          organism = synthetic construct
                          note = synthetic
SEQUENCE: 329
gaggtgcagc tggtggagtc tgggggaggc ttggtaaagc ctgggggtc ccttagactc     60
tcctgtgcag cctctggatt cactttcagt aacgcctgga tgagctgggt ccgccaggct   120
ccagggaagg ggctggaatg ggttggccgt attaaaacca gagctgatgg tgggacaaca   180
gactacgctg cacccgtgaa aggcagattc accatctcaa gagatgattc aaaaaacacg   240
ctgtatctgc aactgaacag cctgaaaacc gaggacacag ccgtgtatta ctgtacctct   300
cataactgga actacgaaga ctttgactac tggggccagg gaaccctggt cactgtctcc   360
tca                                                                 363

SEQ ID NO: 330            moltype = AA   length = 121
FEATURE                   Location/Qualifiers
source                    1..121
                          mol_type = protein
                          organism = synthetic construct
                          note = synthetic
SEQUENCE: 330
EVQLVESGGG LVKPGGSLRL SCAASGFTFS NAWMSWVRQA PGKGLEWVGR IKTRADGGTT    60
DYAAPVKGRF TISRDDSKNT LYLQLNSLKT EDTAVYYCTS HNWNYEDFDY WGQGTLVTVS   120
S                                                                   121
```

```
SEQ ID NO: 331          moltype = DNA  length = 24
FEATURE                 Location/Qualifiers
source                  1..24
                        mol_type = other DNA
                        organism = synthetic construct
                        note = synthetic
SEQUENCE: 331
ggattcactt tcagtaacgc ctgg                                              24

SEQ ID NO: 332          moltype = AA  length = 8
FEATURE                 Location/Qualifiers
source                  1..8
                        mol_type = protein
                        organism = synthetic construct
                        note = synthetic
SEQUENCE: 332
GFTFSNAW                                                                8

SEQ ID NO: 333          moltype = DNA  length = 30
FEATURE                 Location/Qualifiers
source                  1..30
                        mol_type = other DNA
                        organism = synthetic construct
                        note = synthetic
SEQUENCE: 333
attaaaacca gagctgatgg tgggacaaca                                        30

SEQ ID NO: 334          moltype = AA  length = 10
FEATURE                 Location/Qualifiers
source                  1..10
                        mol_type = protein
                        organism = synthetic construct
                        note = synthetic
SEQUENCE: 334
IKTRADGGTT                                                              10

SEQ ID NO: 335          moltype = DNA  length = 36
FEATURE                 Location/Qualifiers
source                  1..36
                        mol_type = other DNA
                        organism = synthetic construct
                        note = synthetic
SEQUENCE: 335
acctctcata actggaacta cgaagacttt gactac                                 36

SEQ ID NO: 336          moltype = AA  length = 12
FEATURE                 Location/Qualifiers
source                  1..12
                        mol_type = protein
                        organism = synthetic construct
                        note = synthetic
SEQUENCE: 336
TSHNWNYEDF DY                                                           12

SEQ ID NO: 337          moltype = DNA  length = 321
FEATURE                 Location/Qualifiers
source                  1..321
                        mol_type = other DNA
                        organism = synthetic construct
                        note = synthetic
SEQUENCE: 337
gacatccaga tgacccagtc tccatcctcc ctgtctgcat ctgtaggaga cagagtcacc       60
atcacttgcc gggcaagtca gagcattagc aactatttaa attggtatca gcagaaacca      120
gggaaagccc ctaaactcct gatctatgct gcatccagtt tgcaaagtgg ggtcccatca      180
aggttcagtg gcagtggatc tgggacagac ttcactctca ccatcagcag tctgcaacct      240
gaagagtttg caacttacta ctgtcaacag agttacagta cccgtacac ttttggccag       300
gggaccaagc tggagatcaa a                                                321

SEQ ID NO: 338          moltype = AA  length = 107
FEATURE                 Location/Qualifiers
source                  1..107
                        mol_type = protein
                        organism = synthetic construct
                        note = synthetic
SEQUENCE: 338
DIQMTQSPSS LSASVGDRVT ITCRASQSIS NYLNWYQQKP GKAPKLLIYA ASSLQSGVPS       60
RFSGSGSGTD FTLTISSLQP EEFATYYCQQ SYSIPYTFGQ GTKLEIK                    107
```

```
SEQ ID NO: 339          moltype = DNA  length = 24
FEATURE                 Location/Qualifiers
source                  1..24
                        mol_type = other DNA
                        organism = synthetic construct
                        note = synthetic
SEQUENCE: 339
gcaagtcaga gcattagcaa ctat                                          24

SEQ ID NO: 340          moltype = AA  length = 8
FEATURE                 Location/Qualifiers
source                  1..8
                        mol_type = protein
                        organism = synthetic construct
                        note = synthetic
SEQUENCE: 340
ASQSISNY                                                            8

SEQ ID NO: 341          moltype = DNA  length = 30
FEATURE                 Location/Qualifiers
source                  1..30
                        mol_type = other DNA
                        organism = synthetic construct
                        note = synthetic
SEQUENCE: 341
gctgcatcca gtttgcaaag tggggtccca                                    30

SEQ ID NO: 342          moltype = AA  length = 10
FEATURE                 Location/Qualifiers
source                  1..10
                        mol_type = protein
                        organism = synthetic construct
                        note = synthetic
SEQUENCE: 342
AASSLQSGVP                                                          10

SEQ ID NO: 343          moltype = DNA  length = 12
FEATURE                 Location/Qualifiers
source                  1..12
                        mol_type = other DNA
                        organism = synthetic construct
                        note = synthetic
SEQUENCE: 343
atcccgtaca ct                                                       12

SEQ ID NO: 344          moltype = AA  length = 4
FEATURE                 Location/Qualifiers
source                  1..4
                        mol_type = protein
                        organism = synthetic construct
                        note = synthetic
SEQUENCE: 344
IPYT                                                                4

SEQ ID NO: 345          moltype = DNA  length = 369
FEATURE                 Location/Qualifiers
source                  1..369
                        mol_type = other DNA
                        organism = synthetic construct
                        note = synthetic
SEQUENCE: 345
gaggtgcagc tggtggagtc tggggggaggc ttggtacagc ctgggggtc cctgagactc   60
tcctgtgcag cctctggatt cacctttagc agctatgcca tgagctgggt ccgccaggct  120
ccagggaagg ggctggagtg gtctcaggt attagtggta gtggtggtac aacatacgac  180
gcagactccg tgaagggccg gttcaccatc tccagagaca attccaagaa cacgctgtat  240
ctgcaaatgc acagtctgag agccgaggac acggccgcat attactgtgc gaaagactgg  300
aactacgggc ctattactac cttcggtatg gacgtctggg gccaagggac cacggtcacc  360
gtctcctca                                                          369

SEQ ID NO: 346          moltype = AA  length = 123
FEATURE                 Location/Qualifiers
source                  1..123
                        mol_type = protein
                        organism = synthetic construct
                        note = synthetic
SEQUENCE: 346
EVQLVESGGG LVQPGGSLRL SCAASGFTFS SYAMSWVRQA PGKGLEWVSG ISGSGGTTYD   60
ADSVKGRFTI SRDNSKNTLY LQMHSLRAED TAAYYCAKDW NYGPYYFGM DVWGQGTTVT   120
VSS                                                                123
```

| SEQ ID NO: 347 | moltype = DNA length = 24 |
| --- | --- |
| FEATURE | Location/Qualifiers |
| source | 1..24 |
| | mol_type = other DNA |
| | organism = synthetic construct |
| | note = synthetic |

SEQUENCE: 347
ggattcacct ttagcagcta tgcc                                              24

| SEQ ID NO: 348 | moltype = AA length = 8 |
| --- | --- |
| FEATURE | Location/Qualifiers |
| source | 1..8 |
| | mol_type = protein |
| | organism = synthetic construct |
| | note = synthetic |

SEQUENCE: 348
GFTFSSYA                                                                 8

| SEQ ID NO: 349 | moltype = DNA length = 24 |
| --- | --- |
| FEATURE | Location/Qualifiers |
| source | 1..24 |
| | mol_type = other DNA |
| | organism = synthetic construct |
| | note = synthetic |

SEQUENCE: 349
attagtggta gtggtggtac aaca                                              24

| SEQ ID NO: 350 | moltype = AA length = 8 |
| --- | --- |
| FEATURE | Location/Qualifiers |
| source | 1..8 |
| | mol_type = protein |
| | organism = synthetic construct |
| | note = synthetic |

SEQUENCE: 350
ISGSGGTT                                                                 8

| SEQ ID NO: 351 | moltype = DNA length = 48 |
| --- | --- |
| FEATURE | Location/Qualifiers |
| source | 1..48 |
| | mol_type = other DNA |
| | organism = synthetic construct |
| | note = synthetic |

SEQUENCE: 351
gcgaaagact ggaactacgg gccctattac tacttcggta tggacgtc                    48

| SEQ ID NO: 352 | moltype = AA length = 16 |
| --- | --- |
| FEATURE | Location/Qualifiers |
| source | 1..16 |
| | mol_type = protein |
| | organism = synthetic construct |
| | note = synthetic |

SEQUENCE: 352
AKDWNYGPYY YFGMDV                                                       16

| SEQ ID NO: 353 | moltype = DNA length = 336 |
| --- | --- |
| FEATURE | Location/Qualifiers |
| source | 1..336 |
| | mol_type = other DNA |
| | organism = synthetic construct |
| | note = synthetic |

SEQUENCE: 353
gatattgtga tgactcagtc tccactctcc ctgcccgtca cccctggaga gccggcctcc        60
atctcctgca ggtctagtca gagcctcctg catagtaatg aatacaacta tttggattgg       120
tacctgcaga agccaggcca gtctccacac ctcctgatct atttgggttc taatcgggcc       180
tccgggggtcc ctgacaggtt cagtggcagt ggatcaggca cagattttac attgaaaatc      240
agcagagtgg aggctgagga tgttggggtt tattactgca tgcaagctct acaaactcct       300
ccgacgttcg gccaagggac caaggtggaa atcaaa                                 336

| SEQ ID NO: 354 | moltype = AA length = 112 |
| --- | --- |
| FEATURE | Location/Qualifiers |
| source | 1..112 |
| | mol_type = protein |
| | organism = synthetic construct |
| | note = synthetic |

SEQUENCE: 354
DIVMTQSPLS LPVTPGEPAS ISCRSSQSLL HSNEYNYLDW YLQKPGQSPQ LLIYLGSNRA        60
SGVPDRFSGS GSGTDFTLKI SRVEAEDVGV YYCMQALQTP PTFGQGTKVE IK               112

```
SEQ ID NO: 355         moltype = DNA  length = 33
FEATURE                Location/Qualifiers
source                 1..33
                       mol_type = other DNA
                       organism = synthetic construct
                       note = synthetic
SEQUENCE: 355
cagagcctcc tgcatagtaa tgaatacaac tat                                    33

SEQ ID NO: 356         moltype = AA  length = 11
FEATURE                Location/Qualifiers
source                 1..11
                       mol_type = protein
                       organism = synthetic construct
                       note = synthetic
SEQUENCE: 356
QSLLHSNEYN Y                                                            11

SEQ ID NO: 357         moltype =   length =
SEQUENCE: 357
000

SEQ ID NO: 358         moltype =   length =
SEQUENCE: 358
000

SEQ ID NO: 359         moltype = DNA  length = 27
FEATURE                Location/Qualifiers
source                 1..27
                       mol_type = other DNA
                       organism = synthetic construct
                       note = synthetic
SEQUENCE: 359
atgcaagctc tacaaactcc tccgacg                                           27

SEQ ID NO: 360         moltype = AA  length = 9
FEATURE                Location/Qualifiers
source                 1..9
                       mol_type = protein
                       organism = synthetic construct
                       note = synthetic
SEQUENCE: 360
MQALQTPPT                                                                9

SEQ ID NO: 361         moltype = DNA  length = 366
FEATURE                Location/Qualifiers
source                 1..366
                       mol_type = other DNA
                       organism = synthetic construct
                       note = synthetic
SEQUENCE: 361
gaggtgcagc tggtggagtc tgggggaggc ttggtacagc ctggggggtc cctgagactc        60
tcctgtgcag cctctggatt cacctttagc agctatgcca tgagctgggt ccgccaggct       120
ccagggcagg ggctggaatg ggtctcagct attagtggta gcggtgatgg cacatactac       180
gcagactccg tgaagggccg gttcaccatc tccagagaca tttccaagaa cacgctgtat       240
ctgcaaatga acagcctgaa aaccgaggac acggccgtat attactgtgc gagagatgcc       300
tataactgga actactactg gtatttcgat ctctggggcc gtggcaccct ggtcaccgtc       360
tcctca                                                                 366

SEQ ID NO: 362         moltype = AA  length = 122
FEATURE                Location/Qualifiers
source                 1..122
                       mol_type = protein
                       organism = synthetic construct
                       note = synthetic
SEQUENCE: 362
EVQLVESGGG LVQPGGSLRL SCAASGFTFS SYAMSWVRQA PGQGLEWVSA ISGSGDGTYY        60
ADSVKGRFTI SRDISKNTLY LQMNSLKTED TAVYYCARDA YNWNYYWYFD LWGRGTLVTV       120
SS                                                                     122

SEQ ID NO: 363         moltype = DNA  length = 24
FEATURE                Location/Qualifiers
source                 1..24
                       mol_type = other DNA
                       organism = synthetic construct
                       note = synthetic
SEQUENCE: 363
ggattcacct ttagcagcta tgcc                                              24
```

-continued

```
SEQ ID NO: 364          moltype = AA   length = 8
FEATURE                 Location/Qualifiers
source                  1..8
                        mol_type = protein
                        organism = synthetic construct
                        note = synthetic
SEQUENCE: 364
GFTFSSYA                                                                8

SEQ ID NO: 365          moltype = DNA   length = 24
FEATURE                 Location/Qualifiers
source                  1..24
                        mol_type = other DNA
                        organism = synthetic construct
                        note = synthetic
SEQUENCE: 365
attagtggta gcggtgatgg caca                                              24

SEQ ID NO: 366          moltype = AA   length = 8
FEATURE                 Location/Qualifiers
source                  1..8
                        mol_type = protein
                        organism = synthetic construct
                        note = synthetic
SEQUENCE: 366
ISGSGDGT                                                                8

SEQ ID NO: 367          moltype = DNA   length = 45
FEATURE                 Location/Qualifiers
source                  1..45
                        mol_type = other DNA
                        organism = synthetic construct
                        note = synthetic
SEQUENCE: 367
gcgagagatg cctataactg gaactactac tggtatttcg atctc                       45

SEQ ID NO: 368          moltype = AA   length = 15
FEATURE                 Location/Qualifiers
source                  1..15
                        mol_type = protein
                        organism = synthetic construct
                        note = synthetic
SEQUENCE: 368
ARDAYNWNYY WYFDL                                                        15

SEQ ID NO: 369          moltype = DNA   length = 321
FEATURE                 Location/Qualifiers
source                  1..321
                        mol_type = other DNA
                        organism = synthetic construct
                        note = synthetic
SEQUENCE: 369
gaaatagtga tgacgcagtc tccagccacc ctgtctgtgt ctccaggaga cagagccacc       60
ctctcctgta gggccagtca gactgttagt agcagcttag tttggtacca gcagaaacct      120
ggccaggctc ccaggctcct catctatggt gcatccacca gggccactgg tatcccagcc      180
aggttcagtg gcagtgggtc tgggactgag ttcactctca ccatcagcag cctgcagtct      240
gaagatttg cagtttatta ctgtcagcag tttaataatt ggccgatcac cttcggccaa       300
gggacacgac tggagattaa a                                                321

SEQ ID NO: 370          moltype = AA   length = 107
FEATURE                 Location/Qualifiers
source                  1..107
                        mol_type = protein
                        organism = synthetic construct
                        note = synthetic
SEQUENCE: 370
EIVMTQSPAT LSVSPGDRAT LSCRASQTVS SSLVWYQQKP GQAPRLLIYG ASTRATGIPA       60
RFSGSGSGTE FTLTISSLQS EDFAVYYCQQ FNNWPITFGQ GTRLEIK                    107

SEQ ID NO: 371          moltype = DNA   length = 18
FEATURE                 Location/Qualifiers
source                  1..18
                        mol_type = other DNA
                        organism = synthetic construct
                        note = synthetic
SEQUENCE: 371
cagactgtta gtagcagc                                                     18

SEQ ID NO: 372          moltype = AA   length = 6
```

```
FEATURE                 Location/Qualifiers
source                  1..6
                        mol_type = protein
                        organism = synthetic construct
                        note = synthetic
SEQUENCE: 372
QTVSSS                                                                    6

SEQ ID NO: 373          moltype =    length =
SEQUENCE: 373
000

SEQ ID NO: 374          moltype =    length =
SEQUENCE: 374
000

SEQ ID NO: 375          moltype = DNA   length = 27
FEATURE                 Location/Qualifiers
source                  1..27
                        mol_type = other DNA
                        organism = synthetic construct
                        note = synthetic
SEQUENCE: 375
cagcagttta ataattggcc gatcacc                                            27

SEQ ID NO: 376          moltype = AA   length = 9
FEATURE                 Location/Qualifiers
source                  1..9
                        mol_type = protein
                        organism = synthetic construct
                        note = synthetic
SEQUENCE: 376
QQFNNWPIT                                                                 9

SEQ ID NO: 377          moltype = DNA   length = 378
FEATURE                 Location/Qualifiers
source                  1..378
                        mol_type = other DNA
                        organism = synthetic construct
                        note = synthetic
SEQUENCE: 377
caggtgcagc tggtggagtc tgggggaggc gtggtccagc cagggaggtc cctgagactc         60
tcctgtgcaa cgtctggatt cacctttagt aactatggca tgcactgggt ccgccaggct        120
caaggcaagg gactggagtg ggtggcagtt atatggtttg atggaagtga taaatactat        180
gcagactccg tgaagggccg attcaccatc tccagagaca attccaagaa cacgctgtat        240
ctgcaaatga acagcctgag agccgaggac acggctgtgt attactgtgc gagagaggct        300
attgtggagg tgattactac ccagggctac tacggtatgg acgtctgggg ccaagggacc        360
acggtcaccg tctcctca                                                     378

SEQ ID NO: 378          moltype = AA   length = 126
FEATURE                 Location/Qualifiers
source                  1..126
                        mol_type = protein
                        organism = synthetic construct
                        note = synthetic
SEQUENCE: 378
QVQLVESGGG VVQPGRSLRL SCATSGFTFS NYGMHWVRQA QGKGLEWVAV IWFDGSDKYY         60
ADSVKGRFTI SRDNSKNTLY LQMNSLRAED TAVYYCAREA IVEVITTQGY YGMDVWGQGT        120
TVTVSS                                                                  126

SEQ ID NO: 379          moltype = DNA   length = 24
FEATURE                 Location/Qualifiers
source                  1..24
                        mol_type = other DNA
                        organism = synthetic construct
                        note = synthetic
SEQUENCE: 379
ggattcacct ttagtaacta tggc                                               24

SEQ ID NO: 380          moltype = AA   length = 8
FEATURE                 Location/Qualifiers
source                  1..8
                        mol_type = protein
                        organism = synthetic construct
                        note = synthetic
SEQUENCE: 380
GFTFSNYG                                                                  8

SEQ ID NO: 381          moltype = DNA   length = 24
```

```
FEATURE                 Location/Qualifiers
source                  1..24
                        mol_type = other DNA
                        organism = synthetic construct
                        note = synthetic
SEQUENCE: 381
atatggtttg atggaagtga taaa                                          24

SEQ ID NO: 382          moltype = AA  length = 8
FEATURE                 Location/Qualifiers
source                  1..8
                        mol_type = protein
                        organism = synthetic construct
                        note = synthetic
SEQUENCE: 382
IWFDGSDK                                                             8

SEQ ID NO: 383          moltype = DNA  length = 57
FEATURE                 Location/Qualifiers
source                  1..57
                        mol_type = other DNA
                        organism = synthetic construct
                        note = synthetic
SEQUENCE: 383
gcgagagagg ctattgtgga ggtgattact acccagggct actacggtat ggacgtc      57

SEQ ID NO: 384          moltype = AA  length = 19
FEATURE                 Location/Qualifiers
source                  1..19
                        mol_type = protein
                        organism = synthetic construct
                        note = synthetic
SEQUENCE: 384
AREAIVEVIT TQGYYGMDV                                                19

SEQ ID NO: 385          moltype = DNA  length = 339
FEATURE                 Location/Qualifiers
source                  1..339
                        mol_type = other DNA
                        organism = synthetic construct
                        note = synthetic
SEQUENCE: 385
gacatcgtga tgacccagtc tccagactcc ctggctgtgt ctctgggcga gagggccacc    60
atcaactgca agtccagcca gactatttta tacagctcca acaataagaa ctacttagct   120
tggtaccagc agaaaccagg acagcctcct aagctgctca tttactggtc atcttcccgg   180
gaatccgggg tccctgaccg attcagtggc agcgggtctg ggacagattt cactctcacc   240
atcagcagcc tgcaggctga agatgtggca gtttattact gtcaacaata ttatactact   300
ccgatcacct tcggccaggg gacacgactg gagattaaa                          339

SEQ ID NO: 386          moltype = AA  length = 113
FEATURE                 Location/Qualifiers
source                  1..113
                        mol_type = protein
                        organism = synthetic construct
                        note = synthetic
SEQUENCE: 386
DIVMTQSPDS LAVSLGERAT INCKSSQTIL YSSNNKNYLA WYQQKPGQPP KLLIYWSSSR    60
ESGVPDRFSG SGSGTDFTLT ISSLQAEDVA VYYCQQYYTT PITFGQGTRL EIK          113

SEQ ID NO: 387          moltype = DNA  length = 36
FEATURE                 Location/Qualifiers
source                  1..36
                        mol_type = other DNA
                        organism = synthetic construct
                        note = synthetic
SEQUENCE: 387
cagactattt tatacagctc caacaataag aactac                             36

SEQ ID NO: 388          moltype = AA  length = 12
FEATURE                 Location/Qualifiers
source                  1..12
                        mol_type = protein
                        organism = synthetic construct
                        note = synthetic
SEQUENCE: 388
QTILYSSNNK NY                                                       12

SEQ ID NO: 389          moltype =     length =
SEQUENCE: 389
```

```
000

SEQ ID NO: 390         moltype =    length =
SEQUENCE: 390
000

SEQ ID NO: 391         moltype = DNA   length = 27
FEATURE                Location/Qualifiers
source                 1..27
                       mol_type = other DNA
                       organism = synthetic construct
                       note = synthetic
SEQUENCE: 391
caacaatatt atactactcc gatcacc                                           27

SEQ ID NO: 392         moltype = AA    length = 9
FEATURE                Location/Qualifiers
source                 1..9
                       mol_type = protein
                       organism = synthetic construct
                       note = synthetic
SEQUENCE: 392
QQYYTTPIT                                                               9

SEQ ID NO: 393         moltype = DNA   length = 366
FEATURE                Location/Qualifiers
source                 1..366
                       mol_type = other DNA
                       organism = synthetic construct
                       note = synthetic
SEQUENCE: 393
gaggtgcagc tggtggagtc tgggggaggc ttggtacagc ctggggggtc cctgagactc       60
tcctgtgcag cctccggact catatttagc aactatgtca tgagctgggt ccgccaggct      120
ccagggaagg ggctggagtg ggtctcaggt atcagtggtg atggtgataa cacatactac      180
gcagattccg tgaagggccg gttcaccatt tccagagaca attccaagaa cactctgtat      240
ctgcaaatga acagcctgag agccgagggc acggccatat attactgtgc gaaagatcac      300
cataactgga atcccgtccc ttatttttgac tactggggcc agggaaccct ggtcaccgtc      360
tcctca                                                                 366

SEQ ID NO: 394         moltype = AA    length = 122
FEATURE                Location/Qualifiers
source                 1..122
                       mol_type = protein
                       organism = synthetic construct
                       note = synthetic
SEQUENCE: 394
EVQLVESGGG LVQPGGSLRL SCAASGLIFS NYVMSWVRQA PGKGLEWVSG ISGDGDNTYY       60
ADSVKGRFTI SRDNSKNTLY LQMNSLRAEG TAIYYCAKDH HNWNPVPYFD YWGQGTLVTV      120
SS                                                                    122

SEQ ID NO: 395         moltype = DNA   length = 24
FEATURE                Location/Qualifiers
source                 1..24
                       mol_type = other DNA
                       organism = synthetic construct
                       note = synthetic
SEQUENCE: 395
ggactcatat ttagcaacta tgtc                                              24

SEQ ID NO: 396         moltype = AA    length = 8
FEATURE                Location/Qualifiers
source                 1..8
                       mol_type = protein
                       organism = synthetic construct
                       note = synthetic
SEQUENCE: 396
GLIFSNYV                                                                8

SEQ ID NO: 397         moltype = DNA   length = 24
FEATURE                Location/Qualifiers
source                 1..24
                       mol_type = other DNA
                       organism = synthetic construct
                       note = synthetic
SEQUENCE: 397
atcagtggtg atggtgataa caca                                              24

SEQ ID NO: 398         moltype = AA    length = 8
FEATURE                Location/Qualifiers
```

```
source                  1..8
                        mol_type = protein
                        organism = synthetic construct
                        note = synthetic
SEQUENCE: 398
ISGDGDNT                                                                    8

SEQ ID NO: 399          moltype = DNA  length = 45
FEATURE                 Location/Qualifiers
source                  1..45
                        mol_type = other DNA
                        organism = synthetic construct
                        note = synthetic
SEQUENCE: 399
gcgaaagatc accataactg gaatcccgtc ccttattttg actac                          45

SEQ ID NO: 400          moltype = AA  length = 15
FEATURE                 Location/Qualifiers
source                  1..15
                        mol_type = protein
                        organism = synthetic construct
                        note = synthetic
SEQUENCE: 400
AKDHHNWNPV PYFDY                                                           15

SEQ ID NO: 401          moltype = DNA  length = 321
FEATURE                 Location/Qualifiers
source                  1..321
                        mol_type = other DNA
                        organism = synthetic construct
                        note = synthetic
SEQUENCE: 401
gaaattgtga tgacgcagtc tccagccacc ctgtctgtgt ctctagggga aagagacacc          60
ctctcctgta gggccagtca gagtgttagc agcaacttag cagagaaacct                   120
ggccaggctc ccaggctcct catctatggt gtatccacca gggccactgg tatcccagcc        180
aggttcagtg gcagtgggtc tgggacagag ttcagtctca ccatcagtag cctgcagtct        240
gaagattttg cagtttatta ctgtcagcag tataataact ggccgctcac tttcggcgga        300
gggaccaagg tggagatcaa a                                                  321

SEQ ID NO: 402          moltype = AA  length = 107
FEATURE                 Location/Qualifiers
source                  1..107
                        mol_type = protein
                        organism = synthetic construct
                        note = synthetic
SEQUENCE: 402
EIVMTQSPAT LSVSLGERDT LSCRASQSVS SNLAWYQQKP GQAPRLLIYG VSTRATGIPA          60
RFSGSGSGTE FSLTISSLQS EDFAVYYCQQ YNNWPLTFGG GTKVEIK                      107

SEQ ID NO: 403          moltype = DNA  length = 18
FEATURE                 Location/Qualifiers
source                  1..18
                        mol_type = other DNA
                        organism = synthetic construct
                        note = synthetic
SEQUENCE: 403
cagagtgtta gcagcaac                                                        18

SEQ ID NO: 404          moltype = AA  length = 6
FEATURE                 Location/Qualifiers
source                  1..6
                        mol_type = protein
                        organism = synthetic construct
                        note = synthetic
SEQUENCE: 404
QSVSSN                                                                      6

SEQ ID NO: 405          moltype =      length =
SEQUENCE: 405
000

SEQ ID NO: 406          moltype =      length =
SEQUENCE: 406
000

SEQ ID NO: 407          moltype = DNA  length = 27
FEATURE                 Location/Qualifiers
source                  1..27
                        mol_type = other DNA
```

```
                               organism = synthetic construct
                               note = synthetic
SEQUENCE: 407
cagcagtata ataactggcc gctcact                                           27

SEQ ID NO: 408          moltype = AA   length = 9
FEATURE                 Location/Qualifiers
source                  1..9
                        mol_type = protein
                        organism = synthetic construct
                        note = synthetic
SEQUENCE: 408
QQYNNWPLT                                                                9

SEQ ID NO: 409          moltype = DNA   length = 375
FEATURE                 Location/Qualifiers
source                  1..375
                        mol_type = other DNA
                        organism = synthetic construct
                        note = synthetic
SEQUENCE: 409
gaggtgcagc tggtggagtc tgggggaggc ttggtaaagc cggggggtc ccttagactt        60
tcctgtgcag cctctggatt cacttcact aacgcctgga tgacctgggt ccgccaggct       120
ccagggaagg ggctgagtg ggttggccgt attaaaagta aaactgatgg tgggacaaca       180
gactacgcag cacccgtgaa aggcagattc accatctcaa gagatgattc aaaaaccacg      240
ctgtatctac aaatgaacag cctgagaacc gaggacacag ccgtgtatta ctgttccata      300
gatccgtta gcagtgtctg gtacttctac gctttggacg tctggggcca agggaccacg      360
gtcaccgtct cctca                                                      375

SEQ ID NO: 410          moltype = AA   length = 125
FEATURE                 Location/Qualifiers
source                  1..125
                        mol_type = protein
                        organism = synthetic construct
                        note = synthetic
SEQUENCE: 410
EVQLVESGGG LVKPGGSLRL SCAASGFTFT NAWMTWVRQA PGKGLEWVGR IKSKTDGGTT       60
DYAAPVKGRF TISRDDSKTT LYLQMNSLRT EDTAVYYCSI DPFSSVWYFY ALDVWGQGTT      120
VTVSS                                                                 125

SEQ ID NO: 411          moltype = DNA   length = 24
FEATURE                 Location/Qualifiers
source                  1..24
                        mol_type = other DNA
                        organism = synthetic construct
                        note = synthetic
SEQUENCE: 411
ggattcactt tcactaacgc ctgg                                              24

SEQ ID NO: 412          moltype = AA   length = 8
FEATURE                 Location/Qualifiers
source                  1..8
                        mol_type = protein
                        organism = synthetic construct
                        note = synthetic
SEQUENCE: 412
GFTFTNAW                                                                 8

SEQ ID NO: 413          moltype = DNA   length = 30
FEATURE                 Location/Qualifiers
source                  1..30
                        mol_type = other DNA
                        organism = synthetic construct
                        note = synthetic
SEQUENCE: 413
attaaaagta aaactgatgg tgggacaaca                                        30

SEQ ID NO: 414          moltype = AA   length = 10
FEATURE                 Location/Qualifiers
source                  1..10
                        mol_type = protein
                        organism = synthetic construct
                        note = synthetic
SEQUENCE: 414
IKSKTDGGTT                                                              10

SEQ ID NO: 415          moltype = DNA   length = 48
FEATURE                 Location/Qualifiers
source                  1..48
```

```
                        mol_type = other DNA
                        organism = synthetic construct
                        note = synthetic
SEQUENCE: 415
tccatagatc cgtttagcag tgtctggtac ttctacgctt tggacgtc               48

SEQ ID NO: 416          moltype = AA   length = 16
FEATURE                 Location/Qualifiers
source                  1..16
                        mol_type = protein
                        organism = synthetic construct
                        note = synthetic
SEQUENCE: 416
SIDPFSSVWY FYALDV                                                  16

SEQ ID NO: 417          moltype = DNA  length = 321
FEATURE                 Location/Qualifiers
source                  1..321
                        mol_type = other DNA
                        organism = synthetic construct
                        note = synthetic
SEQUENCE: 417
gacatccaga tgacccagtc tccatcctcc ctgtctgcat ctgtaggaga cagagtcacc   60
atcacttgcc gggcaagtca gggcattaga aatgatttag gctggtatca gcagaaacca  120
gggaaagccc ctaagcgcct gatctatgct gcatccagtt tgcaaagtgg ggtcccatca  180
aggttcagcg gcagtggatc tgggacagaa ttcactctca caatcagcag cctgcagcct  240
gaagattttg caacttatta ctgtctacag catgatagtt ttcctcccac tttcggcgga  300
gggaccaagg tggagatcaa a                                            321

SEQ ID NO: 418          moltype = AA   length = 107
FEATURE                 Location/Qualifiers
source                  1..107
                        mol_type = protein
                        organism = synthetic construct
                        note = synthetic
SEQUENCE: 418
DIQMTQSPSS LSASVGDRVT ITCRASQGIR NDLGWYQQKP GKAPKRLIYA ASSLQSGVPS   60
RFSGSGSGTE FTLTISSLQP EDFATYYCLQ HDSFPPTFGG GTKVEIK                107

SEQ ID NO: 419          moltype = DNA  length = 18
FEATURE                 Location/Qualifiers
source                  1..18
                        mol_type = other DNA
                        organism = synthetic construct
                        note = synthetic
SEQUENCE: 419
cagggcatta gaaatgat                                                18

SEQ ID NO: 420          moltype = AA   length = 6
FEATURE                 Location/Qualifiers
source                  1..6
                        mol_type = protein
                        organism = synthetic construct
                        note = synthetic
SEQUENCE: 420
QGIRND                                                             6

SEQ ID NO: 421          moltype =      length =
SEQUENCE: 421
000

SEQ ID NO: 422          moltype =      length =
SEQUENCE: 422
000

SEQ ID NO: 423          moltype = DNA  length = 27
FEATURE                 Location/Qualifiers
source                  1..27
                        mol_type = other DNA
                        organism = synthetic construct
                        note = synthetic
SEQUENCE: 423
ctacagcatg atagttttcc tcccact                                      27

SEQ ID NO: 424          moltype = AA   length = 9
FEATURE                 Location/Qualifiers
source                  1..9
                        mol_type = protein
                        organism = synthetic construct
```

```
                        note = synthetic
SEQUENCE: 424
LQHDSFPPT                                                                9

SEQ ID NO: 425          moltype = DNA  length = 375
FEATURE                 Location/Qualifiers
source                  1..375
                        mol_type = other DNA
                        organism = synthetic construct
                        note = synthetic
SEQUENCE: 425
caggtgcagc tggtggagtc tgggggaggc gtggtccagc ctggggaggtc cctgaaactc    60
tcttgtgcag cgtctggatt caccttcagt aactatggca tgcactgggt ccgccaggct   120
ccaggcaagg ggctggagtg ggtgtcagtt atattatttg atggaagtga taaatactat   180
gcagactccg tgaagggccg attcaccatc tccagagaca attccaagaa cacgctgtat   240
ctgcaaatga acagcctgag agccgaggac acggctgtgt attactgtgc gagagatacc   300
ggcgggcgat ttttggagtg gttatccgat gcttttgata tctggggcca agggacaatg   360
gtcaccgtct cttca                                                    375

SEQ ID NO: 426          moltype = AA  length = 125
FEATURE                 Location/Qualifiers
source                  1..125
                        mol_type = protein
                        organism = synthetic construct
                        note = synthetic
SEQUENCE: 426
QVQLVESGGG VVQPGRSLKL SCAASGFTFS NYGMHWVRQA PGKGLEWVSV ILFDGSDKYY     60
ADSVKGRFTI SRDNSKNTLY LQMNSLRAED TAVYYCARDT GGRFLEWLSD AFDIWGQGTM    120
VTVSS                                                                125

SEQ ID NO: 427          moltype = DNA  length = 24
FEATURE                 Location/Qualifiers
source                  1..24
                        mol_type = other DNA
                        organism = synthetic construct
                        note = synthetic
SEQUENCE: 427
ggattcacct tcagtaacta tggc                                            24

SEQ ID NO: 428          moltype = AA  length = 8
FEATURE                 Location/Qualifiers
source                  1..8
                        mol_type = protein
                        organism = synthetic construct
                        note = synthetic
SEQUENCE: 428
GFTFSNYG                                                               8

SEQ ID NO: 429          moltype = DNA  length = 24
FEATURE                 Location/Qualifiers
source                  1..24
                        mol_type = other DNA
                        organism = synthetic construct
                        note = synthetic
SEQUENCE: 429
atattatttg atggaagtga taaa                                            24

SEQ ID NO: 430          moltype = AA  length = 8
FEATURE                 Location/Qualifiers
source                  1..8
                        mol_type = protein
                        organism = synthetic construct
                        note = synthetic
SEQUENCE: 430
ILFDGSDK                                                               8

SEQ ID NO: 431          moltype = DNA  length = 54
FEATURE                 Location/Qualifiers
source                  1..54
                        mol_type = other DNA
                        organism = synthetic construct
                        note = synthetic
SEQUENCE: 431
gcgagagata ccggcgggcg attttggag tggttatccg atgcttttga tatc            54

SEQ ID NO: 432          moltype = AA  length = 18
FEATURE                 Location/Qualifiers
source                  1..18
                        mol_type = protein
```

```
                              -continued

SEQUENCE: 432
ARDTGGRFLE WLSDAFDI                                              18

SEQ ID NO: 433           moltype = DNA  length = 321
FEATURE                  Location/Qualifiers
source                   1..321
                         mol_type = other DNA
                         organism = synthetic construct
                         note = synthetic
SEQUENCE: 433
gccatccaga tgacccagtc tccatcctcc ctgtctacat ctgtaggaga cagagtcacc    60
atcacttgcc gggcgagtca ggacattaga aatgattag gctggtatca gcagaaacca   120
gggaaagccc ctaagctcct gatctatgct gcatccaatt tacaaagtgg ggtcccatca   180
agtttcagcg gcagtggatc tggcacagat ttcactctca ccatcagcag cctgcagcct   240
gaagattttg caacttatta ctgtctgcaa aattacaatt acccgtacac ttttggccag   300
gggaccaagc tggagatcaa a                                            321

SEQ ID NO: 434           moltype = AA  length = 107
FEATURE                  Location/Qualifiers
source                   1..107
                         mol_type = protein
                         organism = synthetic construct
                         note = synthetic
SEQUENCE: 434
AIQMTQSPSS LSTSVGDRVT ITCRASQDIR NDLGWYQQKP GKAPKLLIYA ASNLQSGVPS    60
SFSGSGSGTD FTLTISSLQP EDFATYYCLQ NYNYPYTFGQ GTKLEIK                107

SEQ ID NO: 435           moltype = DNA  length = 18
FEATURE                  Location/Qualifiers
source                   1..18
                         mol_type = other DNA
                         organism = synthetic construct
                         note = synthetic
SEQUENCE: 435
caggacatta gaaatgat                                                 18

SEQ ID NO: 436           moltype = AA  length = 6
FEATURE                  Location/Qualifiers
source                   1..6
                         mol_type = protein
                         organism = synthetic construct
                         note = synthetic
SEQUENCE: 436
QDIRND                                                               6

SEQ ID NO: 437           moltype =      length =
SEQUENCE: 437
000

SEQ ID NO: 438           moltype =      length =
SEQUENCE: 438
000

SEQ ID NO: 439           moltype = DNA  length = 27
FEATURE                  Location/Qualifiers
source                   1..27
                         mol_type = other DNA
                         organism = synthetic construct
                         note = synthetic
SEQUENCE: 439
ctgcaaaatt acaattaccc gtacact                                       27

SEQ ID NO: 440           moltype = AA  length = 9
FEATURE                  Location/Qualifiers
source                   1..9
                         mol_type = protein
                         organism = synthetic construct
                         note = synthetic
SEQUENCE: 440
LQNYNYPYT                                                            9

SEQ ID NO: 441           moltype = DNA  length = 381
FEATURE                  Location/Qualifiers
source                   1..381
                         mol_type = other DNA
                         organism = synthetic construct
                         note = synthetic
```

```
SEQUENCE: 441
gaagtgcagc tggtggagtc tggcggaggc ttggtgcagc ctggcaggtc cctgagactc     60
tcctgtgcag cctctggatt cacctttgat gcttttacca tgcactgggt ccggcacgtt    120
ccagggaagg gcctggagtg ggtctcaggt attagttgga atagtgatag tatagcctat    180
gcggactctg tgaagggccg attcaccatg tccagagaca acgccaagaa ctcccctgtat   240
ctgcaaatga acagtctgag aggtgaggac acggccttct attactgtgc aaaagatctg    300
acgtatgtct ggaaccggga ctaccactac tatttcggta tggacgtctg gggccaaggg    360
accacggtca ccgtctcctc a                                              381

SEQ ID NO: 442         moltype = AA   length = 127
FEATURE                Location/Qualifiers
source                 1..127
                       mol_type = protein
                       organism = synthetic construct
                       note = synthetic
SEQUENCE: 442
EVQLVESGGG LVQPGRSLRL SCAASGFTFD AFTMHWVRHV PGKGLEWVSG ISWNSDSIAY     60
ADSVKGRFTM SRDNAKNSLY LQMNSLRGED TAFYYCAKDL TYVWNRDYHY YFGMDVWGQG    120
TTVTVSS                                                              127

SEQ ID NO: 443         moltype = DNA   length = 24
FEATURE                Location/Qualifiers
source                 1..24
                       mol_type = other DNA
                       organism = synthetic construct
                       note = synthetic
SEQUENCE: 443
ggattcacct ttgatgcttt tacc                                            24

SEQ ID NO: 444         moltype = AA   length = 8
FEATURE                Location/Qualifiers
source                 1..8
                       mol_type = protein
                       organism = synthetic construct
                       note = synthetic
SEQUENCE: 444
GFTFDAFT                                                               8

SEQ ID NO: 445         moltype = DNA   length = 24
FEATURE                Location/Qualifiers
source                 1..24
                       mol_type = other DNA
                       organism = synthetic construct
                       note = synthetic
SEQUENCE: 445
attagttgga atagtgatag tata                                            24

SEQ ID NO: 446         moltype = AA   length = 8
FEATURE                Location/Qualifiers
source                 1..8
                       mol_type = protein
                       organism = synthetic construct
                       note = synthetic
SEQUENCE: 446
ISWNSDSI                                                               8

SEQ ID NO: 447         moltype = DNA   length = 60
FEATURE                Location/Qualifiers
source                 1..60
                       mol_type = other DNA
                       organism = synthetic construct
                       note = synthetic
SEQUENCE: 447
gcaaaagatc tgacgtatgt ctggaaccgg gactaccact actatttcgg tatggacgtc     60

SEQ ID NO: 448         moltype = AA   length = 20
FEATURE                Location/Qualifiers
source                 1..20
                       mol_type = protein
                       organism = synthetic construct
                       note = synthetic
SEQUENCE: 448
AKDLTYVWNR DYHYYFGMDV                                                 20

SEQ ID NO: 449         moltype = DNA   length = 321
FEATURE                Location/Qualifiers
source                 1..321
                       mol_type = other DNA
                       organism = synthetic construct
```

```
                            note = synthetic
SEQUENCE: 449
gacatccaga tgacccagtc tccatcctcc ctgtctgcat ctgtaggaga cagagtcacc    60
atcacttgcc ggacaagtca gagcattagt aactatttaa attggtatca gcagaaacca   120
gggaaagccc ctaaactcct gatctatact gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgatcac cttcggccaa   300
gggacacgac tggagattaa a                                             321

SEQ ID NO: 450          moltype = AA  length = 107
FEATURE                 Location/Qualifiers
source                  1..107
                        mol_type = protein
                        organism = synthetic construct
                        note = synthetic
SEQUENCE: 450
DIQMTQSPSS LSASVGDRVT ITCRTSQSIS NYLNWYQQKP GKAPKLLIYT ASSLQSGVPS    60
RFSGSGSGTD FTLTISSLQP EDFATYYCQQ SYSTPITFGQ GTRLEIK                 107

SEQ ID NO: 451          moltype = DNA  length = 18
FEATURE                 Location/Qualifiers
source                  1..18
                        mol_type = other DNA
                        organism = synthetic construct
                        note = synthetic
SEQUENCE: 451
cagagcatta gtaactat                                                  18

SEQ ID NO: 452          moltype = AA  length = 6
FEATURE                 Location/Qualifiers
source                  1..6
                        mol_type = protein
                        organism = synthetic construct
                        note = synthetic
SEQUENCE: 452
QSISNY                                                                6

SEQ ID NO: 453          moltype =     length =
SEQUENCE: 453
000

SEQ ID NO: 454          moltype =     length =
SEQUENCE: 454
000

SEQ ID NO: 455          moltype = DNA  length = 27
FEATURE                 Location/Qualifiers
source                  1..27
                        mol_type = other DNA
                        organism = synthetic construct
                        note = synthetic
SEQUENCE: 455
caacagagtt acagtacccc gatcacc                                        27

SEQ ID NO: 456          moltype = AA  length = 9
FEATURE                 Location/Qualifiers
source                  1..9
                        mol_type = protein
                        organism = synthetic construct
                        note = synthetic
SEQUENCE: 456
QQSYSTPIT                                                             9

SEQ ID NO: 457          moltype = DNA  length = 375
FEATURE                 Location/Qualifiers
source                  1..375
                        mol_type = other DNA
                        organism = synthetic construct
                        note = synthetic
SEQUENCE: 457
gaagtgcagc tggtggagtc tgggggaggc ttggtacagc ctggcaggtc cctgagactc    60
tcctgtgtag cctctggatt caccttttgat gattacgcca tgcactgggt ccggcaagtt   120
ccagggaagg gcctggagtg ggtctcaggg attacttgga atagtggtaa gttagactat   180
gcggactctg tgaagggccg attcaccatc tccagagaca acgccaagaa ctccctcttt   240
ctgcaaatga acagtctgag agctgaggac acggccttgt attactgtgc aaaagatatg   300
gagggatggt ataactggaa ctattttttt ggttttcata tatggggcca agggacaatg   360
gtcaccgtct cttca                                                    375

SEQ ID NO: 458          moltype = AA  length = 125
```

| FEATURE | Location/Qualifiers |
|---|---|
| source | 1..125<br>mol_type = protein<br>organism = synthetic construct<br>note = synthetic |

SEQUENCE: 458
```
EVQLVESGGG LVQPGRSLRL SCVASGFTFD DYAMHWVRQV PGKGLEWVSG ITWNSGKLDY   60
ADSVKGRFTI SRDNAKNSLF LQMNSLRAED TALYYCAKDM EGWYNWNYFF GFHIWGQGTM  120
VTVSS                                                              125
```

| SEQ ID NO: 459 | moltype = DNA  length = 24 |
|---|---|
| FEATURE | Location/Qualifiers |
| source | 1..24<br>mol_type = other DNA<br>organism = synthetic construct<br>note = synthetic |

SEQUENCE: 459
```
ggattcacct ttgatgatta cgcc                                          24
```

| SEQ ID NO: 460 | moltype = AA  length = 8 |
|---|---|
| FEATURE | Location/Qualifiers |
| source | 1..8<br>mol_type = protein<br>organism = synthetic construct<br>note = synthetic |

SEQUENCE: 460
```
GFTFDDYA                                                            8
```

| SEQ ID NO: 461 | moltype = DNA  length = 24 |
|---|---|
| FEATURE | Location/Qualifiers |
| source | 1..24<br>mol_type = other DNA<br>organism = synthetic construct<br>note = synthetic |

SEQUENCE: 461
```
attacttgga atagtggtaa gtta                                          24
```

| SEQ ID NO: 462 | moltype = AA  length = 8 |
|---|---|
| FEATURE | Location/Qualifiers |
| source | 1..8<br>mol_type = protein<br>organism = synthetic construct<br>note = synthetic |

SEQUENCE: 462
```
ITWNSGKL                                                            8
```

| SEQ ID NO: 463 | moltype = DNA  length = 54 |
|---|---|
| FEATURE | Location/Qualifiers |
| source | 1..54<br>mol_type = other DNA<br>organism = synthetic construct<br>note = synthetic |

SEQUENCE: 463
```
gcaaaagata tggagggatg gtataactgg aactatttttt tggttttca tata         54
```

| SEQ ID NO: 464 | moltype = AA  length = 18 |
|---|---|
| FEATURE | Location/Qualifiers |
| source | 1..18<br>mol_type = protein<br>organism = synthetic construct<br>note = synthetic |

SEQUENCE: 464
```
AKDMEGWYNW NYFFGFHI                                                 18
```

| SEQ ID NO: 465 | moltype = DNA  length = 324 |
|---|---|
| FEATURE | Location/Qualifiers |
| source | 1..324<br>mol_type = other DNA<br>organism = synthetic construct<br>note = synthetic |

SEQUENCE: 465
```
gacatccaga tgacccagtc tccatcctcc ctgtctgcat ctgtaggaga cagagtcacc   60
atcacttgcc gggcaagtcg gaacataggc agcttttttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca tcatcagcag tctgcaacct  240
gaagattttg caacttacta ctgtcaacag agttacagta tacctccgat caccttcggc  300
caagggacac gactggagat taaa                                         324
```

| SEQ ID NO: 466 | moltype = AA  length = 108 |
|---|---|

| | | |
|---|---|---|
| FEATURE | Location/Qualifiers | |
| source | 1..108 | |
| | mol_type = protein | |
| | organism = synthetic construct | |
| | note = synthetic | |
| SEQUENCE: 466 | | |
| DIQMTQSPSS LSASVGDRVT ITCRASRNIG SFLNWYQQKP GKAPKLLIYA ASSLQSGVPS | | 60 |
| RFSGSGSGTD FTLIISSLQP EDFATYYCQQ SYSIPPITFG QGTRLEIK | | 108 |
| | | |
| SEQ ID NO: 467 | moltype = DNA length = 18 | |
| FEATURE | Location/Qualifiers | |
| source | 1..18 | |
| | mol_type = other DNA | |
| | organism = synthetic construct | |
| | note = synthetic | |
| SEQUENCE: 467 | | |
| cggaacatag gcagcttt | | 18 |
| | | |
| SEQ ID NO: 468 | moltype = AA length = 6 | |
| FEATURE | Location/Qualifiers | |
| source | 1..6 | |
| | mol_type = protein | |
| | organism = synthetic construct | |
| | note = synthetic | |
| SEQUENCE: 468 | | |
| RNIGSF | | 6 |
| | | |
| SEQ ID NO: 469 | moltype = length = | |
| SEQUENCE: 469 | | |
| 000 | | |
| | | |
| SEQ ID NO: 470 | moltype = length = | |
| SEQUENCE: 470 | | |
| 000 | | |
| | | |
| SEQ ID NO: 471 | moltype = DNA length = 30 | |
| FEATURE | Location/Qualifiers | |
| source | 1..30 | |
| | mol_type = other DNA | |
| | organism = synthetic construct | |
| | note = synthetic | |
| SEQUENCE: 471 | | |
| caacagagtt acagtatacc tccgatcacc | | 30 |
| | | |
| SEQ ID NO: 472 | moltype = AA length = 10 | |
| FEATURE | Location/Qualifiers | |
| source | 1..10 | |
| | mol_type = protein | |
| | organism = synthetic construct | |
| | note = synthetic | |
| SEQUENCE: 472 | | |
| QQSYSIPPIT | | 10 |
| | | |
| SEQ ID NO: 473 | moltype = DNA length = 375 | |
| FEATURE | Location/Qualifiers | |
| source | 1..375 | |
| | mol_type = other DNA | |
| | organism = synthetic construct | |
| | note = synthetic | |
| SEQUENCE: 473 | | |
| gaggtgcagc tggtggagtc tggggagac ttggtaaagc cggggggtc ccttggactc | | 60 |
| tcctgtgcag cctctggatt cactttcagt gacgcctgga tgaactgggt ccgccaggct | | 120 |
| ccagggaagg ggctggagtg ggttggccgt attaaaagca aaactgatga tgggacaaca | | 180 |
| gacttcgctg cacccgtaaa aggcagattc accatctcaa gagatgattc aaaaaacacg | | 240 |
| ctgtatctgc aaatgaacag cctgaaaacc gacgacacag ccatgtatta ctgtaccaca | | 300 |
| gatttcttcc actataactg ggactactct tttttgact actggggccg ggaaccctg | | 360 |
| gtcaccgtct cctca | | 375 |
| | | |
| SEQ ID NO: 474 | moltype = AA length = 125 | |
| FEATURE | Location/Qualifiers | |
| source | 1..125 | |
| | mol_type = protein | |
| | organism = synthetic construct | |
| | note = synthetic | |
| SEQUENCE: 474 | | |
| EVQLVESGGD LVKPGGSLGL SCAASGFTFS DAWMNWVRQA PGKGLEWVGR IKSKTDDGTT | | 60 |
| DFAAPVKGRF TISRDDSKNT LYLQMNSLKT DDTAMYYCTT DFFHYNWDYS FFDYWGRGTL | | 120 |
| VTVSS | | 125 |

```
SEQ ID NO: 475          moltype = DNA  length = 24
FEATURE                 Location/Qualifiers
source                  1..24
                        mol_type = other DNA
                        organism = synthetic construct
                        note = synthetic
SEQUENCE: 475
ggattcactt tcagtgacgc ctgg                                          24

SEQ ID NO: 476          moltype = AA  length = 8
FEATURE                 Location/Qualifiers
source                  1..8
                        mol_type = protein
                        organism = synthetic construct
                        note = synthetic
SEQUENCE: 476
GFTFSDAW                                                            8

SEQ ID NO: 477          moltype = DNA  length = 30
FEATURE                 Location/Qualifiers
source                  1..30
                        mol_type = other DNA
                        organism = synthetic construct
                        note = synthetic
SEQUENCE: 477
attaaaagca aaactgatga tgggacaaca                                    30

SEQ ID NO: 478          moltype = AA  length = 10
FEATURE                 Location/Qualifiers
source                  1..10
                        mol_type = protein
                        organism = synthetic construct
                        note = synthetic
SEQUENCE: 478
IKSKTDDGTT                                                          10

SEQ ID NO: 479          moltype = DNA  length = 48
FEATURE                 Location/Qualifiers
source                  1..48
                        mol_type = other DNA
                        organism = synthetic construct
                        note = synthetic
SEQUENCE: 479
accacagatt tcttccacta taactgggac tactctttt ttgactac                 48

SEQ ID NO: 480          moltype = AA  length = 16
FEATURE                 Location/Qualifiers
source                  1..16
                        mol_type = protein
                        organism = synthetic construct
                        note = synthetic
SEQUENCE: 480
TTDFFHYNWD YSFFDY                                                   16

SEQ ID NO: 481          moltype = DNA  length = 324
FEATURE                 Location/Qualifiers
source                  1..324
                        mol_type = other DNA
                        organism = synthetic construct
                        note = synthetic
SEQUENCE: 481
gacatccaga tgacccagtc tccatcctcc ctgtctgcat ctgtaggaga cagagtcacc   60
atcacttgcc gggcaagtca gagcattagc tactatttaa attggtatca gcagaaacca  120
gggaaagccc ctaaactcct gatctatgct gcatccactt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                         324

SEQ ID NO: 482          moltype = AA  length = 108
FEATURE                 Location/Qualifiers
source                  1..108
                        mol_type = protein
                        organism = synthetic construct
                        note = synthetic
SEQUENCE: 482
DIQMTQSPSS LSASVGDRVT ITCRASQSIS YYLNWYQQKP GKAPKLLIYA ASTLQSGVPS   60
RFSGSGSGTD FTLTISSLQP EDFATYYCQQ SYSTPPITFG QGTRLEIK               108

SEQ ID NO: 483          moltype = DNA  length = 18
```

| FEATURE | Location/Qualifiers |
|---|---|
| source | 1..18 |
| | mol_type = other DNA |
| | organism = synthetic construct |
| | note = synthetic |

SEQUENCE: 483
cagagcatta gctactat                                                    18

| SEQ ID NO: 484 | moltype = AA   length = 6 |
|---|---|
| FEATURE | Location/Qualifiers |
| source | 1..6 |
| | mol_type = protein |
| | organism = synthetic construct |
| | note = synthetic |

SEQUENCE: 484
QSISYY                                                                  6

| SEQ ID NO: 485 | moltype =   length = |
|---|---|

SEQUENCE: 485
000

| SEQ ID NO: 486 | moltype =   length = |
|---|---|

SEQUENCE: 486
000

| SEQ ID NO: 487 | moltype = DNA   length = 30 |
|---|---|
| FEATURE | Location/Qualifiers |
| source | 1..30 |
| | mol_type = other DNA |
| | organism = synthetic construct |
| | note = synthetic |

SEQUENCE: 487
caacagagtt acagtacccc tccgatcacc                                        30

| SEQ ID NO: 488 | moltype = AA   length = 10 |
|---|---|
| FEATURE | Location/Qualifiers |
| source | 1..10 |
| | mol_type = protein |
| | organism = synthetic construct |
| | note = synthetic |

SEQUENCE: 488
QQSYSTPPIT                                                             10

| SEQ ID NO: 489 | moltype = DNA   length = 378 |
|---|---|
| FEATURE | Location/Qualifiers |
| source | 1..378 |
| | mol_type = other DNA |
| | organism = synthetic construct |
| | note = synthetic |

SEQUENCE: 489
caggtgcagc tggtggagtc tgggggaggc ttggtcaagc ctggagggtc cctgagactc        60
tcctgtacag cctctggatt cacccttcagt gactactaca tgagctggat ccgccaggct      120
ccagggaagg gactgagtg ggtttcatac attagtagta gtggaaatac catatactac        180
gcagactctg tgaagggccg attcaccatc tccaggaca cgccaagaa ctcactgtat         240
ctgcaaatga acagcctgag agccgaggac acggccgtgt attactgtgc gagacttggg      300
atattcctat ggttcgggga gttattcctt gatgcttttg atatctgggg ccaagggaca      360
atggtcaccg tctcttca                                                    378

| SEQ ID NO: 490 | moltype = AA   length = 126 |
|---|---|
| FEATURE | Location/Qualifiers |
| source | 1..126 |
| | mol_type = protein |
| | organism = synthetic construct |
| | note = synthetic |

SEQUENCE: 490
QVQLVESGGG LVKPGGSLRL SCTASGFTFS DYYMSWIRQA PGKGLEWVSY ISSSGNTIYY        60
ADSVKGRFTI SRDNAKNSLY LQMNSLRAED TAVYYCARLG IFLWFGELFL DAFDIWGQGT      120
MVTVSS                                                                126

| SEQ ID NO: 491 | moltype = DNA   length = 24 |
|---|---|
| FEATURE | Location/Qualifiers |
| source | 1..24 |
| | mol_type = other DNA |
| | organism = synthetic construct |
| | note = synthetic |

SEQUENCE: 491
ggattcacct tcagtgacta ctac                                              24

| SEQ ID NO: 492 | moltype = AA   length = 8 |
|---|---|

```
FEATURE                 Location/Qualifiers
source                  1..8
                        mol_type = protein
                        organism = synthetic construct
                        note = synthetic
SEQUENCE: 492
GFTFSDYY                                                                  8

SEQ ID NO: 493          moltype = DNA  length = 24
FEATURE                 Location/Qualifiers
source                  1..24
                        mol_type = other DNA
                        organism = synthetic construct
                        note = synthetic
SEQUENCE: 493
attagtagta gtggaaatac cata                                               24

SEQ ID NO: 494          moltype = AA  length = 8
FEATURE                 Location/Qualifiers
source                  1..8
                        mol_type = protein
                        organism = synthetic construct
                        note = synthetic
SEQUENCE: 494
ISSSGNTI                                                                  8

SEQ ID NO: 495          moltype = DNA  length = 57
FEATURE                 Location/Qualifiers
source                  1..57
                        mol_type = other DNA
                        organism = synthetic construct
                        note = synthetic
SEQUENCE: 495
gcgagacttg ggatattcct atggttcggg gagttattcc ttgatgcttt tgatatc           57

SEQ ID NO: 496          moltype = AA  length = 19
FEATURE                 Location/Qualifiers
source                  1..19
                        mol_type = protein
                        organism = synthetic construct
                        note = synthetic
SEQUENCE: 496
ARLGIFLWFG ELFLDAFDI                                                     19

SEQ ID NO: 497          moltype = DNA  length = 324
FEATURE                 Location/Qualifiers
source                  1..324
                        mol_type = other DNA
                        organism = synthetic construct
                        note = synthetic
SEQUENCE: 497
gacatccaga tgacccagtc tccatcctcc ctgtctgcat ctgtaggaga cagagtcacc        60
atcacttgcc gggcaagtca gatcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                              324

SEQ ID NO: 498          moltype = AA  length = 108
FEATURE                 Location/Qualifiers
source                  1..108
                        mol_type = protein
                        organism = synthetic construct
                        note = synthetic
SEQUENCE: 498
DIQMTQSPSS LSASVGDRVT ITCRASQIIS SYLNWYQQKP GKAPKLLIYA ASSLQSGVPS        60
RFSGSGSGTD FTLTISSLQP EDFATYYCQQ SYSIPPITFG QGTRLEIK                    108

SEQ ID NO: 499          moltype = DNA  length = 18
FEATURE                 Location/Qualifiers
source                  1..18
                        mol_type = other DNA
                        organism = synthetic construct
                        note = synthetic
SEQUENCE: 499
cagatcatta gcagctat                                                      18

SEQ ID NO: 500          moltype = AA  length = 6
FEATURE                 Location/Qualifiers
```

```
source                  1..6
                        mol_type = protein
                        organism = synthetic construct
                        note = synthetic
SEQUENCE: 500
QIISSY                                                                      6

SEQ ID NO: 501          moltype =    length =
SEQUENCE: 501
000

SEQ ID NO: 502          moltype =    length =
SEQUENCE: 502
000

SEQ ID NO: 503          moltype = DNA   length = 30
FEATURE                 Location/Qualifiers
source                  1..30
                        mol_type = other DNA
                        organism = synthetic construct
                        note = synthetic
SEQUENCE: 503
caacagagtt acagtatccc tccgatcacc                                           30

SEQ ID NO: 504          moltype = AA   length = 10
FEATURE                 Location/Qualifiers
source                  1..10
                        mol_type = protein
                        organism = synthetic construct
                        note = synthetic
SEQUENCE: 504
QQSYSIPPIT                                                                 10

SEQ ID NO: 505          moltype = DNA   length = 381
FEATURE                 Location/Qualifiers
source                  1..381
                        mol_type = other DNA
                        organism = synthetic construct
                        note = synthetic
SEQUENCE: 505
gaggtgcagc tgttggagtc tggggaggc ttggtacaac ctgggggtc cctgagactc            60
tcctgtgcag cctctggatt caccttagc agttatgcca tgacctgggt ccgccaggct          120
ccagggatgg gactggagtg ggtctcagtt attagtggta gtggtagtga aacatactac         180
gcagactccg tgaagggccg gttcaccatc tccagagaca attccaaaaa cacactgtat         240
ctgcaaatga acagcctgag agccgaagac acggccgtat attactgtgt gaaagattct         300
tcgtatagga gctcgtcgag ggcctactac tactacggaa tggacgtctg gggcctaggg         360
accacggtca ccgtctcctc a                                                   381

SEQ ID NO: 506          moltype = AA   length = 127
FEATURE                 Location/Qualifiers
source                  1..127
                        mol_type = protein
                        organism = synthetic construct
                        note = synthetic
SEQUENCE: 506
EVQLLESGGG LVQPGGSLRL SCAASGFTFS SYAMTWVRQA PGMGLEWVSV ISGSGSETYY          60
ADSVKGRFTI SRDNSKNTLY LQMNSLRAED TAVYYCVKDS SYRSSSRAYY YYGMDVWGLG         120
TTVTVSS                                                                   127

SEQ ID NO: 507          moltype = DNA   length = 24
FEATURE                 Location/Qualifiers
source                  1..24
                        mol_type = other DNA
                        organism = synthetic construct
                        note = synthetic
SEQUENCE: 507
ggattcacct ttagcagtta tgcc                                                 24

SEQ ID NO: 508          moltype = AA   length = 8
FEATURE                 Location/Qualifiers
source                  1..8
                        mol_type = protein
                        organism = synthetic construct
                        note = synthetic
SEQUENCE: 508
GFTFSSYA                                                                    8

SEQ ID NO: 509          moltype = DNA   length = 24
FEATURE                 Location/Qualifiers
```

```
source                  1..24
                        mol_type = other DNA
                        organism = synthetic construct
                        note = synthetic
SEQUENCE: 509
attagtggta gtggtagtga aaca                                              24

SEQ ID NO: 510          moltype = AA  length = 8
FEATURE                 Location/Qualifiers
source                  1..8
                        mol_type = protein
                        organism = synthetic construct
                        note = synthetic
SEQUENCE: 510
ISGSGSET                                                                 8

SEQ ID NO: 511          moltype = DNA  length = 60
FEATURE                 Location/Qualifiers
source                  1..60
                        mol_type = other DNA
                        organism = synthetic construct
                        note = synthetic
SEQUENCE: 511
gtgaaagatt cttcgtatag gagctcgtcg agggcctact actactacgg aatggacgtc       60

SEQ ID NO: 512          moltype = AA  length = 20
FEATURE                 Location/Qualifiers
source                  1..20
                        mol_type = protein
                        organism = synthetic construct
                        note = synthetic
SEQUENCE: 512
VKDSSYRSSS RAYYYYGMDV                                                   20

SEQ ID NO: 513          moltype = DNA  length = 324
FEATURE                 Location/Qualifiers
source                  1..324
                        mol_type = other DNA
                        organism = synthetic construct
                        note = synthetic
SEQUENCE: 513
gacatccaga tgacccagtc tccatcctcc ctgtctgcat ctgtaggaga cagagtcacc       60
atcacttgcc gggcaagtca gagcattagc agctatttaa attggtatca acagaaacca     120
gggaaagccc ctaagctcct gatctatgct gtttccattt tgcaaagtgg ggtcccatca     180
aggttcagtg gcagtggatc tgggacagat ttcactctca ccatcaactc tctgcaacct     240
gaagattttg caacttactc ctgtcaacag acttacagta cccctccgat caccttcggc     300
caagggacac gactggagat taaa                                             324

SEQ ID NO: 514          moltype = AA  length = 108
FEATURE                 Location/Qualifiers
source                  1..108
                        mol_type = protein
                        organism = synthetic construct
                        note = synthetic
SEQUENCE: 514
DIQMTQSPSS LSASVGDRVT ITCRASQSIS SYLNWYQQKP GKAPKLLIYA VSILQSGVPS       60
RFSGSGSGTD FTLTINSLQP EDFATYSCQQ TYSTPPITFG QGTRLEIK                   108

SEQ ID NO: 515          moltype = DNA  length = 18
FEATURE                 Location/Qualifiers
source                  1..18
                        mol_type = other DNA
                        organism = synthetic construct
                        note = synthetic
SEQUENCE: 515
cagagcatta gcagctat                                                     18

SEQ ID NO: 516          moltype = AA  length = 6
FEATURE                 Location/Qualifiers
source                  1..6
                        mol_type = protein
                        organism = synthetic construct
                        note = synthetic
SEQUENCE: 516
QSISSY                                                                   6

SEQ ID NO: 517          moltype =     length =
SEQUENCE: 517
000
```

```
SEQ ID NO: 518         moltype =     length =
SEQUENCE: 518
000

SEQ ID NO: 519         moltype = DNA   length = 30
FEATURE                Location/Qualifiers
source                 1..30
                       mol_type = other DNA
                       organism = synthetic construct
                       note = synthetic
SEQUENCE: 519
caacagactt acagtacccc tccgatcacc                                      30

SEQ ID NO: 520         moltype = AA    length = 10
FEATURE                Location/Qualifiers
source                 1..10
                       mol_type = protein
                       organism = synthetic construct
                       note = synthetic
SEQUENCE: 520
QQTYSTPPIT                                                            10

SEQ ID NO: 521         moltype = DNA   length = 381
FEATURE                Location/Qualifiers
source                 1..381
                       mol_type = other DNA
                       organism = synthetic construct
                       note = synthetic
SEQUENCE: 521
gaggtgcagc tattggagtc agggggaggc ttggtacagc cggggggggtc cctgagactc    60
tcctgtgcag cctctggatt cacctttagt ggctatgccg tgagctgggt ccgccaggct   120
ccagggaagg ggctggagtg ggtctcaact attagtggaa gtggtactat cacacattac   180
gtagactccg tgaagggccg gttcaccatc tcccgagaca attccaagaa cacgctgtat   240
ctgcaaatga gcagcctgag agccgaggac acggccatat attactgtgc gagagacccg   300
tattacgatg ttttgactgg ttattataag gaggactact tgactactg gggccaggga   360
accctggtca ccgtctcctc a                                              381

SEQ ID NO: 522         moltype = AA    length = 127
FEATURE                Location/Qualifiers
source                 1..127
                       mol_type = protein
                       organism = synthetic construct
                       note = synthetic
SEQUENCE: 522
EVQLLESGGG LVQPGGSLRL SCAASGFTFS GYAVSWVRQA PGKGLEWVST ISGSGTITHY    60
VDSVKGRFTI SRDNSKNTLY LQMSSLRAED TAIYYCARDP YYDVLTGYYK EDYFDYWGQG   120
TLVTVSS                                                              127

SEQ ID NO: 523         moltype = DNA   length = 24
FEATURE                Location/Qualifiers
source                 1..24
                       mol_type = other DNA
                       organism = synthetic construct
                       note = synthetic
SEQUENCE: 523
ggattcacct ttagtggcta tgcc                                            24

SEQ ID NO: 524         moltype = AA    length = 8
FEATURE                Location/Qualifiers
source                 1..8
                       mol_type = protein
                       organism = synthetic construct
                       note = synthetic
SEQUENCE: 524
GFTFSGYA                                                               8

SEQ ID NO: 525         moltype = DNA   length = 24
FEATURE                Location/Qualifiers
source                 1..24
                       mol_type = other DNA
                       organism = synthetic construct
                       note = synthetic
SEQUENCE: 525
attagtggaa gtggtactat caca                                            24

SEQ ID NO: 526         moltype = AA    length = 8
FEATURE                Location/Qualifiers
source                 1..8
```

```
                        mol_type = protein
                        organism = synthetic construct
                        note = synthetic
SEQUENCE: 526
ISGSGTIT                                                              8

SEQ ID NO: 527          moltype = DNA   length = 60
FEATURE                 Location/Qualifiers
source                  1..60
                        mol_type = other DNA
                        organism = synthetic construct
                        note = synthetic
SEQUENCE: 527
gcgagagacc cgtattacga tgtttttgact ggttattata aggaggacta ctttgactac    60

SEQ ID NO: 528          moltype = AA    length = 20
FEATURE                 Location/Qualifiers
source                  1..20
                        mol_type = protein
                        organism = synthetic construct
                        note = synthetic
SEQUENCE: 528
ARDPYYDVLT GYYKEDYFDY                                                 20

SEQ ID NO: 529          moltype = DNA   length = 324
FEATURE                 Location/Qualifiers
source                  1..324
                        mol_type = other DNA
                        organism = synthetic construct
                        note = synthetic
SEQUENCE: 529
gacatccaga tgacccagtc tccatcctcc ctgtctgcat ctgtaggaga cagagtcacc     60
atcacttgcc gggcaagtca gagcattagc aactatttaa attggtatca gcagaaacca   120
gggaaagccc ctaagctcct gatctatgct gcattcagct tgcaaactgg ggtcccatca   180
aggttcagtg gcagtggatc tgggacagat ttcactctca ccatcagcag tctgcaacct   240
gaagattttg caacttacta ctgtcaacag agttacagta ccccctccga tcaccttcggc  300
caagggacac gactggagat taaa                                          324

SEQ ID NO: 530          moltype = AA    length = 108
FEATURE                 Location/Qualifiers
source                  1..108
                        mol_type = protein
                        organism = synthetic construct
                        note = synthetic
SEQUENCE: 530
DIQMTQSPSS LSASVGDRVT ITCRASQSIS NYLNWYQQKP GKAPKLLIYA AFSLQTGVPS     60
RFSGSGSGTD FTLTISSLQP EDFATYYCQQ SYSTPPITFG QGTRLEIK                 108

SEQ ID NO: 531          moltype = DNA   length = 18
FEATURE                 Location/Qualifiers
source                  1..18
                        mol_type = other DNA
                        organism = synthetic construct
                        note = synthetic
SEQUENCE: 531
cagagcatta gcaactat                                                   18

SEQ ID NO: 532          moltype = AA    length = 6
FEATURE                 Location/Qualifiers
source                  1..6
                        mol_type = protein
                        organism = synthetic construct
                        note = synthetic
SEQUENCE: 532
QSISNY                                                                 6

SEQ ID NO: 533          moltype =       length =
SEQUENCE: 533
000

SEQ ID NO: 534          moltype =       length =
SEQUENCE: 534
000

SEQ ID NO: 535          moltype = DNA   length = 30
FEATURE                 Location/Qualifiers
source                  1..30
                        mol_type = other DNA
                        organism = synthetic construct
```

```
                                note = synthetic
SEQUENCE: 535
caacagagtt acagtacccc tccgatcacc                                    30

SEQ ID NO: 536              moltype = AA   length = 10
FEATURE                     Location/Qualifiers
source                      1..10
                            mol_type = protein
                            organism = synthetic construct
                            note = synthetic
SEQUENCE: 536
QQSYSTPPIT                                                          10

SEQ ID NO: 537              moltype = AA   length = 98
FEATURE                     Location/Qualifiers
source                      1..98
                            mol_type = protein
                            organism = synthetic construct
                            note = GenBank Ac. No: NP_041326.1
SEQUENCE: 537
MHGDTPTLHE YMLDLQPETT DLYCYEQLND SSEEEDEIDG PAGQAEPDRA HYNIVTFCCK    60
CDSTLRLCVQ STHVDIRTLE DLLMGTLGIV CPICSQKP                           98

SEQ ID NO: 538              moltype = AA   length = 9
FEATURE                     Location/Qualifiers
source                      1..9
                            mol_type = protein
                            organism = synthetic construct
                            note = HPV16E7:11-19
SEQUENCE: 538
YMLDLQPET                                                            9

SEQ ID NO: 539              moltype = AA   length = 9
FEATURE                     Location/Qualifiers
source                      1..9
                            mol_type = protein
                            organism = synthetic construct
                            note = HPV16E7:82-90
SEQUENCE: 539
LLMGTLGIV                                                            9

SEQ ID NO: 540              moltype = AA   length = 478
FEATURE                     Location/Qualifiers
source                      1..478
                            mol_type = protein
                            organism = synthetic construct
                            note = 17364N CAR
SEQUENCE: 540
DIQMTQSPSS LSASVGDRVT ITCRASQSIS SYLNWYQQKP GKAPKLLIYA VSILQSGVPS    60
RFSGSGSGTD FTLTISSLQP EDFATYSCQQ TYSTPPITFG QGTRLEIKGG GGSGGGGSGG   120
GGSEVQLLES GGGLVQPGGS LRLSCAASGF TFSSYAMTWV RQAPGKGLEW VSVISGSGSE   180
TYYADSVKGR FTISRDNSKN TLYLQMNSLR AEDTAVYYCV KDSSYRSSSR AYYYYGMDVW   240
GLGTTVTVSS GGGGSTTTPA PRPPTPAPTI ASQPLSLRPE ACRPAAGGAV HTRGLDFACD   300
IYIWAPLAGT CGVLLLSLVI TLYCKRGRKK LLYIFKQPFM RPVQTTQEED GCSCRFPEEE   360
EGGCELRVKF SRSADAPAYK QGQNQLYNEL NLGRREEYDV LDKRRGRDPE MGGKPRRKNP   420
QEGLYNELQK DKMAEAYSEI GMKGERRRGK GHDGLYQGLS TATKDTYDAL HMQALPPR    478

SEQ ID NO: 541              moltype = AA   length = 476
FEATURE                     Location/Qualifiers
source                      1..476
                            mol_type = protein
                            organism = synthetic construct
                            note = 17670P CAR
SEQUENCE: 541
DIQMTQSPSS LSASVGDRVT ITCRASQSIS SYLNWYQQKP GKAPKLLIYA ASNLQSGVPS    60
RFSGSGSGTD FTLTISSLQP EDFATYYCQQ SYSGPPITFG QGTRLEIKGG GGSGGGGSGG   120
GGSEVQLVES GGDLVQPGTS LRLSCEASGF TLSFYAMYWV RQAPGKELEL VSGISGNGES   180
MFYGNSVKGR FSISRDNSKN TLYLQMGSVR AEDMAVYYCA RAYASGNSYF FYYGMDVWGQ   240
GTTVTVSSGG GGSTTTPAPR PPTPAPTIAS QPLSLRPEAC RPAAGGAVHT RGLDFACDIY   300
IWAPLAGTCG VLLLSLVITL YCKRGRKKLL YIFKQPFMRP VQTTQEEDGC SCRFPEEEEG   360
GCELRVKFSR SADAPAYKQG QNQLYNELNL GRREEYDVLD KRRGRDPEMG GKPRRKNPQE   420
GLYNELQKDK MAEAYSEIGM KGERRRGKGH DGLYQGLSTA TKDTYDALHM QALPPR      476

SEQ ID NO: 542              moltype = AA   length = 476
FEATURE                     Location/Qualifiers
source                      1..476
                            mol_type = protein
                            organism = synthetic construct
                            note = 17675P CAR
```

```
SEQUENCE: 542
DIQMTQSPSS LSASVGDRIT ITCRASQSIS SYLNWYQQKP GKAPNLLIYA ASNLQSGVPS    60
RFSGSGSGTD FTLTISSLQP EDFATYYCQQ SYSTPPITFG QGTRLEIKGG GGSGGGGSGG   120
GGSEVQLVES GGGLVQPGAS LRLSCEASGF TLSFYAMHWV RQAPGKELEY VSGISGNGNS   180
IYYRDSVKGR FTISRDNSKN TLYLQMSVG  AEDMAVYYCA RSYSSGNSYY YYYGMDVWGQ   240
GTTVTVSSGG GGSTTTPAPR PPTPAPTIAS QPLSLRPEAC RPAAGGAVHT RGLDFACDIY   300
IWAPLAGTCG VLLLSLVITL YCKRGRKKLL YIFKQPFMRP VQTTEEDGC  SCRFPEEEEG   360
GCELRVKFSR SADAPAYKQG QNQLYNELNL GRREEYDVLD KRRGRDPEMG GKPRRKNPQE   420
GLYNELQKDK MAEAYSEIGM KGERRRGKGH DGLYQGLSTA TKDTYDALHM QALPPR       476

SEQ ID NO: 543          moltype = AA  length = 476
FEATURE                 Location/Qualifiers
source                  1..476
                        mol_type = protein
                        organism = synthetic construct
                        note = 17930N2 CAR
SEQUENCE: 543
DIQMTQSPSS LSASVGDRVT ITCRASQSIS SYLNWYQQKP GKAPKLLIYA ASSLQSGVPS    60
RFSGSGSGTD FTLTISSLHP EDFATYYCQQ SYSTPPITFG QGTRLEIKGG GGSGGGGSGG   120
GGSEVQLVES GGGLVQPGGS LRLSCAASGF TFSYYALHWV RQAPGKGLEY VSAISGNGGS   180
TYYADSVKGR FTISRDKSMS TVYLQVGSLR AEDMAVYYCA RSYASSSDYH YYYGMDVWGQ   240
GTTVTVSSGG GGSTTTPAPR PPTPAPTIAS QPLSLRPEAC RPAAGGAVHT RGLDFACDIY   300
IWAPLAGTCG VLLLSLVITL YCKRGRKKLL YIFKQPFMRP VQTTEEDGC  SCRFPEEEEG   360
GCELRVKFSR SADAPAYKQG QNQLYNELNL GRREEYDVLD KRRGRDPEMG GKPRRKNPQE   420
GLYNELQKDK MAEAYSEIGM KGERRRGKGH DGLYQGLSTA TKDTYDALHM QALPPR       476

SEQ ID NO: 544          moltype = AA  length = 476
FEATURE                 Location/Qualifiers
source                  1..476
                        mol_type = protein
                        organism = synthetic construct
                        note = 21064P CAR
SEQUENCE: 544
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIKGG GGSGGGGSGG   120
GGSEVQLVES GGGLVQPGGS LRLSCAASGF TFTFYAMHWV RQAPGKGLEY VSGISSNGGS   180
TKYADSVKGR FTISRDNSKN TLYLQMGSLR AEDLAVYYCA RSYASSSDYH YYYGMDVWGQ   240
GTTVTVSSGG GGSTTTPAPR PPTPAPTIAS QPLSLRPEAC RPAAGGAVHT RGLDFACDIY   300
IWAPLAGTCG VLLLSLVITL YCKRGRKKLL YIFKQPFMRP VQTTEEDGC  SCRFPEEEEG   360
GCELRVKFSR SADAPAYKQG QNQLYNELNL GRREEYDVLD KRRGRDPEMG GKPRRKNPQE   420
GLYNELQKDK MAEAYSEIGM KGERRRGKGH DGLYQGLSTA TKDTYDALHM QALPPR       476

SEQ ID NO: 545          moltype = AA  length = 478
FEATURE                 Location/Qualifiers
source                  1..478
                        mol_type = protein
                        organism = synthetic construct
                        note = 17363N CAR
SEQUENCE: 545
DIQMTQSPSS LSASVGDRVT ITCRASQSIS SYLNWYQQKP GKAPKLLIYA VSILQSGVPS    60
RFSGSGSGTD FTLTINSLQP EDFATYSCQQ TYSTPPITFG QGTRLEIKGG GGSGGGGSGG   120
GGSEVQLLES GGGLVQPGGS LRLSCAASGF TFSSYAMTWV RQAPGMGLEW VSVISGSGSE   180
TYYADSVKGR FTISRDNSKN TLYLQMNSLR AEDTAVYYCV KDSSYRSSSR AYYYYGMDVW   240
GLGTTVTVSS GGGGSTTTPA PRPPTPAPTI ASQPLSLRPE ACRPAAGGAV HTRGLDFACD   300
IYIWAPLAGT CGVLLLSLVI TLYCKRGRKK LLYIFKQPFM RPVQTTQEED GCSCRFPEEE   360
EGGCELRVKF SRSADAPAYK QGQNQLYNEL NLGRREEYDV LDKRRGRDPE MGGKPRRKNP   420
QEGLYNELQK DKMAEAYSEI GMKGERRRGK GHDGLYQGLS TATKDTYDAL HMQALPPR     478

SEQ ID NO: 546          moltype = AA  length = 9
FEATURE                 Location/Qualifiers
source                  1..9
                        mol_type = protein
                        organism = synthetic construct
                        note = SH3GLB1:244-252
SEQUENCE: 546
YMLDLQKQL                                                            9

SEQ ID NO: 547          moltype = AA  length = 9
FEATURE                 Location/Qualifiers
source                  1..9
                        mol_type = protein
                        organism = synthetic construct
                        note = CAMKK1:388-396
SEQUENCE: 547
KMLDKNPET                                                            9

SEQ ID NO: 548          moltype = AA  length = 9
FEATURE                 Location/Qualifiers
source                  1..9
```

```
                        mol_type = protein
                        organism = synthetic construct
                        note = USP47:691-699
SEQUENCE: 548
YMFDLLLET                                                                9

SEQ ID NO: 549          moltype = AA   length = 9
FEATURE                 Location/Qualifiers
source                  1..9
                        mol_type = protein
                        organism = synthetic construct
                        note = CHPF:463:471
SEQUENCE: 549
YTLDLQLEA                                                                9

SEQ ID NO: 550          moltype = AA   length = 9
FEATURE                 Location/Qualifiers
source                  1..9
                        mol_type = protein
                        organism = synthetic construct
                        note = PKD1:2694-2702
SEQUENCE: 550
MMLILQAET                                                                9

SEQ ID NO: 551          moltype = AA   length = 9
FEATURE                 Location/Qualifiers
source                  1..9
                        mol_type = protein
                        organism = synthetic construct
                        note = NBR1:357-365
SEQUENCE: 551
LMLPLQPCT                                                                9

SEQ ID NO: 552          moltype = AA   length = 9
FEATURE                 Location/Qualifiers
source                  1..9
                        mol_type = protein
                        organism = synthetic construct
                        note = CBL:83-91
SEQUENCE: 552
YILDLLPDT                                                                9

SEQ ID NO: 553          moltype = AA   length = 9
FEATURE                 Location/Qualifiers
source                  1..9
                        mol_type = protein
                        organism = synthetic construct
                        note = PPP4R4:20-28
SEQUENCE: 553
YMEDLQELT                                                                9

SEQ ID NO: 554          moltype = AA   length = 9
FEATURE                 Location/Qualifiers
source                  1..9
                        mol_type = protein
                        organism = synthetic construct
                        note = SBK3:285-293
SEQUENCE: 554
GLLDLDPET                                                                9

SEQ ID NO: 555          moltype = AA   length = 9
FEATURE                 Location/Qualifiers
source                  1..9
                        mol_type = protein
                        organism = synthetic construct
                        note = FNDC3B:921-929
SEQUENCE: 555
VMKDLLPET                                                                9

SEQ ID NO: 556          moltype = AA   length = 9
FEATURE                 Location/Qualifiers
source                  1..9
                        mol_type = protein
                        organism = synthetic construct
                        note = VPREB3:9-17
SEQUENCE: 556
LLMGTFLSV                                                                9

SEQ ID NO: 557          moltype = AA   length = 9
```

```
FEATURE              Location/Qualifiers
source               1..9
                     mol_type = protein
                     organism = synthetic construct
                     note = B4GALT2:4-12
SEQUENCE: 557
LLGGTLERV                                                                        9

SEQ ID NO: 558       moltype = AA  length = 9
FEATURE              Location/Qualifiers
source               1..9
                     mol_type = protein
                     organism = synthetic construct
                     note = GCAT:312-320
SEQUENCE: 558
LLMGSNTIV                                                                        9

SEQ ID NO: 559       moltype = AA  length = 9
FEATURE              Location/Qualifiers
source               1..9
                     mol_type = protein
                     organism = synthetic construct
                     note = CYP39A1:246-254
SEQUENCE: 559
LLQATLDIV                                                                        9

SEQ ID NO: 560       moltype = AA  length = 9
FEATURE              Location/Qualifiers
source               1..9
                     mol_type = protein
                     organism = synthetic construct
                     note = ALDH3A2:467-475
SEQUENCE: 560
LLLTFLGIV                                                                        9

SEQ ID NO: 561       moltype = AA  length = 9
FEATURE              Location/Qualifiers
source               1..9
                     mol_type = protein
                     organism = synthetic construct
                     note = CLCN4:79-87
SEQUENCE: 561
LLAGTLAGV                                                                        9

SEQ ID NO: 562       moltype = AA  length = 9
FEATURE              Location/Qualifiers
source               1..9
                     mol_type = protein
                     organism = synthetic construct
                     note = ZHX2:234-242
SEQUENCE: 562
LLQDTLGHV                                                                        9

SEQ ID NO: 563       moltype = AA  length = 9
FEATURE              Location/Qualifiers
source               1..9
                     mol_type = protein
                     organism = synthetic construct
                     note = GRM6:590-598
SEQUENCE: 563
LLLAVLGIV                                                                        9

SEQ ID NO: 564       moltype = AA  length = 9
FEATURE              Location/Qualifiers
source               1..9
                     mol_type = protein
                     organism = synthetic construct
                     note = IPO9:582-590
SEQUENCE: 564
LVMETLCIV                                                                        9

SEQ ID NO: 565       moltype = AA  length = 9
FEATURE              Location/Qualifiers
source               1..9
                     mol_type = protein
                     organism = synthetic construct
                     note = IPO4:163-171
SEQUENCE: 565
LLNETLGEV                                                                        9
```

| | | |
|---|---|---|
| SEQ ID NO: 566<br>FEATURE<br>source | moltype = AA   length = 9<br>Location/Qualifiers<br>1..9<br>mol_type = protein<br>organism = synthetic construct<br>note = SF3B1:969-977 | |
| SEQUENCE: 566<br>KLMGHLGVV | | 9 |
| SEQ ID NO: 567<br>FEATURE<br>source | moltype = AA   length = 9<br>Location/Qualifiers<br>1..9<br>mol_type = protein<br>organism = synthetic construct<br>note = DOCK11:1282-1290 | |
| SEQUENCE: 567<br>LLMCYLYIV | | 9 |
| SEQ ID NO: 568<br>FEATURE<br>source | moltype = AA   length = 9<br>Location/Qualifiers<br>1..9<br>mol_type = protein<br>organism = synthetic construct<br>note = hCNOT1:1962-1970 | |
| SEQUENCE: 568<br>LLNKVLGIV | | 9 |
| SEQ ID NO: 569<br>FEATURE<br>source | moltype = AA   length = 9<br>Location/Qualifiers<br>1..9<br>mol_type = protein<br>organism = synthetic construct<br>note = synthetic | |
| SEQUENCE: 569<br>AMLDLQPET | | 9 |
| SEQ ID NO: 570<br>FEATURE<br>source | moltype = AA   length = 9<br>Location/Qualifiers<br>1..9<br>mol_type = protein<br>organism = synthetic construct<br>note = synthetic | |
| SEQUENCE: 570<br>YALDLQPET | | 9 |
| SEQ ID NO: 571<br>FEATURE<br>source | moltype = AA   length = 9<br>Location/Qualifiers<br>1..9<br>mol_type = protein<br>organism = synthetic construct<br>note = synthetic | |
| SEQUENCE: 571<br>YMADLQPET | | 9 |
| SEQ ID NO: 572<br>FEATURE<br>source | moltype = AA   length = 9<br>Location/Qualifiers<br>1..9<br>mol_type = protein<br>organism = synthetic construct<br>note = synthetic | |
| SEQUENCE: 572<br>YMLALQPET | | 9 |
| SEQ ID NO: 573<br>FEATURE<br>source | moltype = AA   length = 9<br>Location/Qualifiers<br>1..9<br>mol_type = protein<br>organism = synthetic construct<br>note = synthetic | |
| SEQUENCE: 573<br>YMLDAQPET | | 9 |
| SEQ ID NO: 574<br>FEATURE<br>source | moltype = AA   length = 9<br>Location/Qualifiers<br>1..9<br>mol_type = protein<br>organism = synthetic construct<br>note = synthetic | |

```
SEQUENCE: 574
YMLDLAPET                                                                    9

SEQ ID NO: 575          moltype = AA  length = 9
FEATURE                 Location/Qualifiers
source                  1..9
                        mol_type = protein
                        organism = synthetic construct
                        note = synthetic
SEQUENCE: 575
YMLDLQAET                                                                    9

SEQ ID NO: 576          moltype = AA  length = 9
FEATURE                 Location/Qualifiers
source                  1..9
                        mol_type = protein
                        organism = synthetic construct
                        note = synthetic
SEQUENCE: 576
YMLDLQPAT                                                                    9

SEQ ID NO: 577          moltype = AA  length = 9
FEATURE                 Location/Qualifiers
source                  1..9
                        mol_type = protein
                        organism = synthetic construct
                        note = synthetic
SEQUENCE: 577
YMLDLQPEA                                                                    9

SEQ ID NO: 578          moltype = AA  length = 453
FEATURE                 Location/Qualifiers
source                  1..453
                        mol_type = protein
                        organism = synthetic construct
                        note = HC 17363N
SEQUENCE: 578
EVQLLESGGG LVQPGGSLRL SCAASGFTFS SYAMTWVRQA PGMGLEWVSV ISGSGSETYY      60
ADSVKGRFTI SRDNSKNTLY LQMNSLRAED TAVYYCVKDS SYRSSSRAYY YYGMDVWGLG     120
TTVTVSSAST KGPSVFPLAP CSRSTSESTA ALGCLVKDYF PEPVTVSWNS GALTSGVHTF     180
PAVLQSSGLY SLSSVVTVPS SSLGTKTYTC NVDHKPSNTK VDKRVESKYG PPCPPCPAPP     240
VAGPSVFLFP PKPKDTLMIS RTPEVTCVVV DVSQEDPEVQ FNWYVDGVEV HNAKTKPREE     300
QFNSTYRVVS VLTVLHQDWL NGKEYKCKVS NKGLPSSIEK TISKAKGQPR EPQVYTLPPS     360
QEEMTKNQVS LTCLVKGFYP SDIAVEWESN GQPENNYKTT PPVLDSDGSF FLYSRLTVDK     420
SRWQEGNVFS CSVMHEALHN HYTQKSLSLS LGK                                  453

SEQ ID NO: 579          moltype = AA  length = 215
FEATURE                 Location/Qualifiers
source                  1..215
                        mol_type = protein
                        organism = synthetic construct
                        note = LC 17363N
SEQUENCE: 579
DIQMTQSPSS LSASVGDRVT ITCRASQSIS SYLNWYQQKP GKAPKLLIYA VSILQSGVPS      60
RFSGSGSGTD FTLTINSLQP EDFATYSCQQ TYSTPPITFG QGTRLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 580          moltype = AA  length = 453
FEATURE                 Location/Qualifiers
source                  1..453
                        mol_type = protein
                        organism = synthetic construct
                        note = HC 17364N
SEQUENCE: 580
EVQLLESGGG LVQPGGSLRL SCAASGFTFS SYAMTWVRQA PGKGLEWVSV ISGSGSETYY      60
ADSVKGRFTI SRDNSKNTLY LQMNSLRAED TAVYYCVKDS SYRSSSRAYY YYGMDVWGLG     120
TTVTVSSAST KGPSVFPLAP CSRSTSESTA ALGCLVKDYF PEPVTVSWNS GALTSGVHTF     180
PAVLQSSGLY SLSSVVTVPS SSLGTKTYTC NVDHKPSNTK VDKRVESKYG PPCPPCPAPP     240
VAGPSVFLFP PKPKDTLMIS RTPEVTCVVV DVSQEDPEVQ FNWYVDGVEV HNAKTKPREE     300
QFNSTYRVVS VLTVLHQDWL NGKEYKCKVS NKGLPSSIEK TISKAKGQPR EPQVYTLPPS     360
QEEMTKNQVS LTCLVKGFYP SDIAVEWESN GQPENNYKTT PPVLDSDGSF FLYSRLTVDK     420
SRWQEGNVFS CSVMHEALHN HYTQKSLSLS LGK                                  453

SEQ ID NO: 581          moltype = AA  length = 215
FEATURE                 Location/Qualifiers
source                  1..215
                        mol_type = protein
                        organism = synthetic construct
```

```
                        note = LC 17364N
SEQUENCE: 581
DIQMTQSPSS LSASVGDRVT ITCRASQSIS SYLNWYQQKP GKAPKLLIYA VSILQSGVPS   60
RFSGSGSGTD FTLTISSLQP EDFATYSCQQ TYSTPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 582          moltype = AA  length = 451
FEATURE                 Location/Qualifiers
source                  1..451
                        mol_type = protein
                        organism = synthetic construct
                        note = HC 17670P
SEQUENCE: 582
EVQLVESGGD LVQPGTSLRL SCEASGFTLS FYAMYWVRQA PGKELELVSG ISGNGESMFY   60
GNSVKGRFSI SRDNSKNTLY LQMGSVRAED MAVYYCARAY ASGNSYFFYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPPVA  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPSQE  360
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG K                                 451

SEQ ID NO: 583          moltype = AA  length = 215
FEATURE                 Location/Qualifiers
source                  1..215
                        mol_type = protein
                        organism = synthetic construct
                        note = LC 17670P
SEQUENCE: 583
DIQMTQSPSS LSASVGDRVT ITCRASQSIS SYLNWYQQKP GKAPKLLIYA ASNLQSGVPS   60
RFSGSGSGTD FTLTISSLQP EDFATYYCQQ SYSGPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 584          moltype = AA  length = 451
FEATURE                 Location/Qualifiers
source                  1..451
                        mol_type = protein
                        organism = synthetic construct
                        note = HC 17675P
SEQUENCE: 584
EVQLVESGGG LVQPGASLRL SCEASGFTLS FYAMHWVRQA PGKELEYVSG ISGNGNSIYY   60
RDSVKGRFTI SRDNSKNTLY LQMGSVGAED MAVYYCARSY SSGNSYYYYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPPVA  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPSQE  360
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG K                                 451

SEQ ID NO: 585          moltype = AA  length = 215
FEATURE                 Location/Qualifiers
source                  1..215
                        mol_type = protein
                        organism = synthetic construct
                        note = LC 17675P
SEQUENCE: 585
DIQMTQSPSS LSASVGDRIT ITCRASQSIS SYLNWYQQKP GKAPNLLIYA ASNLQSGVPS   60
RFSGSGSGTD FTLTISSLQP EDFATYYCQQ SYSTPPITFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 586          moltype = AA  length = 451
FEATURE                 Location/Qualifiers
source                  1..451
                        mol_type = protein
                        organism = synthetic construct
                        note = HC 17930N2
SEQUENCE: 586
EVQLVESGGG LVQPGGSLRL SCAASGFTFS YYALHWVRQA PGKGLEYVSA ISGNGGSTYY   60
ADSVKGRFTI SRDKSMSTVY LQVGSLRAED MAVYYCARSY ASSSDYHYYY GMDVWGQGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPPVA  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPSQE  360
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG K                                 451
```

```
SEQ ID NO: 587           moltype = AA  length = 214
FEATURE                  Location/Qualifiers
source                   1..214
                         mol_type = protein
                         organism = synthetic construct
                         note = LC 17930N2
SEQUENCE: 587
DIQMTQSPSS LSASVGDRVT ITCRASQSIS SYLNWYQQKP GKAPKLLIYA ASSLQSGVPS      60
RFSGSGSGTD FTLTISSLQP EDFATYYCQQ SYSTPPITFG QGTRLEIKTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 588           moltype = AA  length = 450
FEATURE                  Location/Qualifiers
source                   1..450
                         mol_type = protein
                         organism = synthetic construct
                         note = HC 21058P
SEQUENCE: 588
EVQLVESGGN VVRPGGSLRL SCAASGFTFD DYGMSWVRQA PGKGLEWVSG INWNGDSTNY      60
ADSVKGRFTI SRDNAKNSLY LQMNSLRAED TALYHCARAG IVVDWNYAGW FDPWGQGTLV     120
TVSSASTKGP SVFPLAPCSR STSESTAALG CLVKDYFPEP VTVSWNSGAL TSGVHTFPAV     180
LQSSGLYSLS SVVTVPSSSL GTKTYTCNVD HKPSNTKVDK RVESKYGPPC PPCPAPPVAG     240
PSVFLFPPKP KDTLMISRTP EVTCVVVDVS QEDPEVQFNW YVDGVEVHNA KTKPREEQFN     300
STYRVVSVLT VLHQDWLNGK EYKCKVSNKG LPSSIEKTIS KAKGQPREPQ VYTLPPSQEE     360
MTKNQVSLTC LVKGFYPSDI AVEWESNGQP ENNYKTTPPV LDSDGSFFLY SRLTVDKSRW     420
QEGNVFSCSV MHEALHNHYT QKSLSLSLGK                                      450

SEQ ID NO: 589           moltype = AA  length = 215
FEATURE                  Location/Qualifiers
source                   1..215
                         mol_type = protein
                         organism = synthetic construct
                         note = LC 21058P
SEQUENCE: 589
DIQMTQSPSS LSASVGDRVT ITCRASQSIS SYLNWYQQEP GKAPKLLIYA ASSLQSGVPS      60
RFSGSGSGTD FTLTISSLQP EDFATYYCQQ SYSTPPITFG QGTKLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 590           moltype = AA  length = 451
FEATURE                  Location/Qualifiers
source                   1..451
                         mol_type = protein
                         organism = synthetic construct
                         note = HC 21064P
SEQUENCE: 590
EVQLVESGGG LVQPGGSLRL SCAASGFTFT FYAMHWVRQA PGKGLEYVSG ISSNGGSTKY      60
ADSVKGRFTI SRDNSKNTLY LQMGSLRAED LAVYYCARSY ASSSDYHYYY GMDVWGQGTT     120
VTVSSASTKG PSVFPLAPCS RSTSESTAAL GCLVKDYFPE PVTVSWNSGA LTSGVHTFPA     180
VLQSSGLYSL SSVVTVPSSS LGTKTYTCNV DHKPSNTKVD KRVESKYGPP CPPCPAPPVA     240
GPSVFLFPPK PKDTLMISRT PEVTCVVVDV SQEDPEVQFN WYVDGVEVHN AKTKPREEQF     300
NSTYRVVSVL TVLHQDWLNG KEYKCKVSNK GLPSSIEKTI SKAKGQPREP QVYTLPPSQE     360
EMTKNQVSLT CLVKGFYPSD IAVEWESNGQ PENNYKTTPP VLDSDGSFFL YSRLTVDKSR     420
WQEGNVFSCS VMHEALHNHY TQKSLSLSLG K                                    451

SEQ ID NO: 591           moltype = AA  length = 214
FEATURE                  Location/Qualifiers
source                   1..214
                         mol_type = protein
                         organism = synthetic construct
                         note = LC 21064P
SEQUENCE: 591
DIQMTQSPSS LSASVGDRVT ITCRASQSIS SYLNWYQQKP GKAPKLLIYA ASSLQSGVPS      60
RFSGSGSGTD FTLTISSLQP EDFATYYCQQ SYSTPPITFG QGTRLEIKTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 592           moltype = AA  length = 452
FEATURE                  Location/Qualifiers
source                   1..452
                         mol_type = protein
                         organism = synthetic construct
                         note = HC 21104P
SEQUENCE: 592
QVQLVESGGG LVKPGGSLRL SCTASGFTFS DYYMSWIRQA PGKGLEWVSY ISSSGNTIYY      60
ADSVKGRFTI SRDNAKNSLY LQMNSLRAED TAVYYCARLG IFLWFGELFL DAFDIWGQGT     120
MVTVSSASTK GPSVFPLAPC SRSTSESTAA LGCLVKDYFP EPVTVSWNSG ALTSGVHTFP     180
AVLQSSGLYS LSSVVTVPSS SLGTKTYTCN VDHKPSNTKV DKRVESKYGP PCPPCPAPPV     240
```

```
AGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL GK                                452

SEQ ID NO: 593         moltype = AA  length = 215
FEATURE                Location/Qualifiers
source                 1..215
                       mol_type = protein
                       organism = synthetic construct
                       note = LC 21104P
SEQUENCE: 593
DIQMTQSPSS LSASVGDRVT ITCRASQIIS SYLNWYQQKP GKAPKLLIYA ASSLQSGVPS   60
RFSGSGSGTD FTLTISSLQP EDFATYYCQQ SYSIPPITFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                             215

SEQ ID NO: 594         moltype = AA  length = 6
FEATURE                Location/Qualifiers
source                 1..6
                       mol_type = protein
                       organism = synthetic construct
SEQUENCE: 594
HHHHHH                                                             6
```

What is claimed is:

1. An isolated nucleic acid molecule encoding a chimeric antigen receptor (CAR),
wherein the CAR comprises an extracellular binding domain that specifically binds to a conformational epitope of an HLA-A2 presented human papillomavirus (HPV) 16 E7 peptide (HPV16E7 peptide), a transmembrane domain, and an intracellular signaling domain,
wherein the extracellular binding domain is a human monoclonal anti-HLA-A2:HPV16E7 antibody, or antigen-binding fragment thereof, comprising three heavy chain complementarity determining regions (CDRs) (HCDR1, HCDR2 and HCDR3); and three light chain CDRs (LCDR1, LCDR2 and LCDR3),
wherein the HCDR1, HCDR2 HCDR3, LCDR1, LCDR2 and LCDR3 comprise the amino acid sequence set having at least 90% amino acid sequence identity to the entire amino acid sequence of SEQ ID NOs: 508, 510, 512, 516, 518, and 520, respectively.

2. A vector comprising the isolated nucleic acid molecule of claim 1.

3. An isolated immune effector cell comprising the vector of claim 2.

4. The isolated nucleic acid molecule of claim 1, wherein the HCDR1, HCDR2 HCDR3, LCDR1, LCDR2 and LCDR3 comprise the amino acid sequence set having at least 95% amino acid sequence identity to the entire amino acid sequence of SEQ ID NOs: 508, 510, 512, 516, 518, and 520, respectively.

5. The isolated nucleic acid molecule of claim 4, wherein the HCDR1, HCDR2 HCDR3, LCDR1, LCDR2 and LCDR3 comprise the amino acid sequence set having at least 98% amino acid sequence identity to the entire amino acid sequence of SEQ ID NOs: 508, 510, 512, 516, 518, and 520, respectively.

6. The isolated nucleic acid molecule of claim 5, wherein the HCDR1, HCDR2 HCDR3, LCDR1, LCDR2 and LCDR3 comprise the amino acid sequence set of SEQ ID NOs: 508, 510, 512, 516, 518, and 520, respectively.

7. The isolated nucleic acid molecule of claim 6, comprising a heavy chain variable region (HCVR)/light chain variable region (LCVR) (HCVR/LCVR) amino acid sequence pair, wherein the amino acid sequence of the HCVR and the amino acid sequence of the LCVR of each HCVR/LCVR pair are each independently at least 90% identical to the amino acid sequences of an HCVR/LCVR amino acid sequence pair of SEQ ID NOs: 506/514.

8. The isolated nucleic acid molecule of claim 7, wherein the amino acid sequence of the HCVR and the amino acid sequence of the LCVR of each HCVR/LCVR pair are each independently at least 95% identical to the amino acid sequences of an HCVR/LCVR amino acid sequence pair of SEQ ID NOs: 506/514.

9. The isolated nucleic acid molecule of claim 8, wherein the amino acid sequence of the HCVR and the amino acid sequence of the LCVR of each HCVR/LCVR pair are each independently at least 98% identical to the amino acid sequences of an HCVR/LCVR amino acid sequence pair of SEQ ID NOs: 506/514.

10. The isolated nucleic acid molecule of claim 8, wherein the amino acid sequence of the HCVR and the amino acid sequence of the LCVR of the HCVR/LCVR pair are 506/514.

11. The isolated nucleic acid molecule of claim 6, comprising a heavy chain variable region (HCVR)/light chain variable region (LCVR) (HCVR/LCVR) amino acid sequence pair, wherein the amino acid sequence of the HCVR and the amino acid sequence of the LCVR of each HCVR/LCVR pair are each independently at least 90% identical to the amino acid sequences of an HCVR/LCVR amino acid sequence pair of SEQ ID NOs: 2/10.

12. The isolated nucleic acid molecule of claim 11, wherein the amino acid sequence of the HCVR and the amino acid sequence of the LCVR of each HCVR/LCVR pair are each independently at least 95% identical to the amino acid sequences of an HCVR/LCVR amino acid sequence pair of SEQ ID NOs: 2/10.

13. The isolated nucleic acid molecule of claim 12, wherein the amino acid sequence of the HCVR and the amino acid sequence of the LCVR of each HCVR/LCVR pair are each independently at least 98% identical to the amino acid sequences of an HCVR/LCVR amino acid sequence pair of SEQ ID NOs: 2/10.

14. The isolated nucleic acid molecule of claim 13, wherein the amino acid sequence of the HCVR and the amino acid sequence of the LCVR of the HCVR/LCVR pair are 2/10.

15. The isolated nucleic acid molecule of claim 10, comprising SEQ ID NO: 540.

16. The isolated nucleic acid molecule of claim 14, comprising SEQ ID NO:545.

17. The isolated antigen-binding protein of claim 1, wherein the human monoclonal anti-HLA-A2:HPV16E7 antibody, or antigen-binding fragment thereof, is a single chain Fv (scFv).

18. The isolated antigen-binding protein of claim 1, wherein the HPV16E7 peptide comprises the amino acid sequence of YMLDLQPET (SEQ ID NO: 538).

19. The isolated immune effector cell of claim 3, which is a T-body.

* * * * *